US012736547B2

(12) United States Patent
Van Meter

(10) Patent No.: US 12,736,547 B2
(45) **Date of Patent: *Sep. 15, 2026**

(54) PROTEIN BIOMARKER INDICATORS OF NEUROLOGICAL INJURY AND/OR DISEASE AND METHODS OF USE THEREOF

(71) Applicant: BRAINBOX SOLUTIONS, INC., Richmond, VA (US)

(72) Inventor: Timothy E. Van Meter, Richmond, VA (US)

(73) Assignee: BRAINBOX SOLUTIONS, INC., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/645,977

(22) Filed: Apr. 25, 2024

(65) Prior Publication Data

US 2025/0044303 A1 Feb. 6, 2025

Related U.S. Application Data

(62) Division of application No. 16/763,794, filed as application No. PCT/US2018/061372 on Nov. 15, 2018, now Pat. No. 11,988,676.

(60) Provisional application No. 62/587,272, filed on Nov. 16, 2017.

(51) Int. Cl.

*G01N 33/68* (2006.01)
*C07K 16/28* (2006.01)
*C07K 16/36* (2006.01)

(52) U.S. Cl.

CPC ..... *G01N 33/6896* (2013.01); *C07K 16/2803* (2013.01); *C07K 16/36* (2013.01); *G01N 33/6848* (2013.01); *G01N 2333/705* (2013.01); *G01N 2333/755* (2013.01); *G01N 2333/825* (2013.01)

(58) Field of Classification Search

CPC ........... G01N 33/6896; G01N 33/6848; G01N 2333/705; G01N 2333/755; G01N 2333/825; G01N 33/564; C07K 16/2803; C07K 16/36

See application file for complete search history.

(56) References Cited

U.S. PATENT DOCUMENTS

2017/0145506 A1 5/2017 Merchant-Borna et al.

FOREIGN PATENT DOCUMENTS

WO 2016/205828 A2 12/2016

OTHER PUBLICATIONS

International Search Report and Written Opinion in International Application No. PCT/US2018/061372, dated Mar. 26, 2019.

International Preliminary Report on Patentability in International Application No. PCT/US2018/061372, dated May 28, 2020.

*Primary Examiner* — Kimberly Ballard
*Assistant Examiner* — Stacey N MacFarlane
(74) *Attorney, Agent, or Firm* — Raphael Bellum PLLC

(57) ABSTRACT

Methods, compositions and kits useful in the detection, assessment, diagnosis, prognosis and/or treatment of neurological injury or disease or brain injury, such as traumatic brain injury (TBI), are provided in which certain newly discovered protein biomarkers are detected in a biological sample of a subject undergoing testing or evaluation. The methods allow for detection of changes in levels, amounts, or concentrations of the protein biomarkers in a subject compared with those of controls. Detection of the protein biomarkers, and/or levels thereof, provides an indication of biological and biochemical events, e.g., at a cellular level, that are occurring in the subject who is undergoing testing or analysis for the neurological injury or brain injury.

10 Claims, 20 Drawing Sheets

Specification includes a Sequence Listing.

TABLE 1

| No. | Protein name (Gene name) | Amino acid sequence for detected protein | Accession number | MW (kDa) | Function | Tissue/Cell Specificity | Cell location | Role in brain repair process |
|---|---|---|---|---|---|---|---|---|
| 1 | 14-3-3 protein sigma (SFN) | SEQ ID NO 1 | NP_006133.1 14-3-3 protein sigma [Homo sapiens] | 28 kDa | structural | Ubiquitous | Nuclear | Unknown |
| 2 | 1-phosphatidylinositol 4,5-bisphosphate phosphodiesterase eta-1 (PLCH1) | SEQ ID NO 2 | NP_001336180.1 1-phosphatidyl inositol 4,5bisphosphate phosphodiesterase eta-1 isoform d [Homo sapiens] | 189 kDa | Cell signaling | Ubiquitous | Cell membrane | Membrane repair |
| 3 | ATP Binding Cassette sub-family A member 2 (ABCA2) | SEQ ID NO 3 | NP_001597.2 ATP-binding cassette sub-family A member 2 isoform a [Homo sapiens] | 47 kDa | Proteolysis | Ubiquitous | extracellular | Inflammation |
| 4 | Alpha-1-antitrypsin (SERPINA1) | SEQ ID NO 4 | NP_001121179.1 alpha-1-antitrypsin precursor [Homo sapiens] | 47 kDa | Metabolic enzyme | Ubiquitous | cytoplasm | Neurodegeneration |
| 5 | Ankyrin repeat domain-containing protein 20A4 (ANKRD20A4) | SEQ ID NO 5 | NP_001092275.1 ankyrin repeat domain-containing protein 20A4 [Homo sapiens] | 94 kDa | Unknown | Unknown | Nucleus | Unknown |
| 6 | Annexin A2 (ANXA2) | SEQ ID NO 6 | NP_001002858.1 annexin A2 isoform 1 [Homo sapiens] | 39 kDa | Cell adhesion | Ubiquitous | Cell membrane | Synaptogenesis |
| 7 | AP-3 complex subunit beta-2 (AP3B2) | SEQ ID NO 7 | NP_001265441.1 AP-3 complex subunit beta-2 isoform 1 [Homo sapiens] | 119 kDa | Gene regulation | Neurons, brain specific | cytoplasm nucleus | Synaptogenesis |
| 8 | Apolipoprotein A-I (APOA1) | SEQ ID NO 8 | NP_001304947.1 apolipoprotein A-I isoform 1 preproprotein [Homo sapiens] | 31 kDa | Lipid binding | Blood | extracellular | Inflammation |

FIG. 1A

TABLE 1

| No. | Protein name (Gene name) | Amino acid sequence for detected protein | Accession number | MW (kDa) | Function | Tissue/Cell Specificity | Cell location | Role in brain repair process |
|---|---|---|---|---|---|---|---|---|
| 9 | Apolipoprotein B-100 (APOB) | SEQ ID NO 9 | NP_000375.2 apolipoprotein B-100 | 516 kDa | Lipid binding | Blood | extracellular | Inflammation |
| 10 | Apolipoprotein E (APOE) | SEQ ID NO 10 | NP_001289617.1 apolipoprotein E isoform a precursor [Homo sapiens] | 36 kDa | Lipid binding | Blood | extracellular | Neurodegeneration |
| 11 | Arginase-1 (ARG1) | SEQ ID NO 11 | XP_011534103.1 PREDICTED: arginase-1 isoform X1 [Homo sapiens] | 35 kDa | Metabolic enzyme | Ubiquitous | extracellular | Metabolism |
| 12 | Astrotactin-2 (ASTN2) | SEQ ID NO 12 | NP_054729.3 astrotactin-2 isoform a precursor [Homo sapiens] | 148 kDa | Cell adhesion | Neuron/glia | Cell membrane | Synaptogenesis |
| 13 | Bile acid receptor (NR1H4) | SEQ ID NO 13 | NP_001193906.1 bile acid receptor isoform 1 [Homo sapiens] | 270 kDa | Involved in microtubule trafficking | Interneurons, muscle | Cell membrane | Synaptogenesis |
| 14 | Biorientation of chromosomes in cell division protein 1-like 1 (BOD1L1) | SEQ ID NO 14 | NP_683692.2 biorientation of chromosomes in cell division protein 1-like 1 [Homo sapiens] | 56 kDa | Metabolic enzyme | Blood, heart, liver | Nucleus | Metabolism |
| 15 | Calcium-activated potassium channel subunit alpha-1 (KCNMA1) | SEQ ID NO 15 | AAI44497.1 KCNMA1 protein [Homo sapiens] | 330 kDa | Gene regulation | Blood, liver, heart | Nucleus | Metabolism |
| 16 | Calmodulin (CALM1) | SEQ ID NO 16 | NP_008819.1 calmodulin-1 [Homo sapiens] | 329 kDa | Cell adhesion | Neuron-specific | Cell membrane | Synaptogenesis |

FIG. 1B

TABLE 1

| No. | Protein name (Gene name) | Amino acid sequence for detected protein | Accession number | MW (kDa) | Function | Tissue/Cell Specificity | Cell location | Role in brain repair process |
|---|---|---|---|---|---|---|---|---|
| 17 | Calmodulin-like protein 3 (CALML3) | SEQ ID NO 17 | NP_005176.1 calmodulin-like protein 3 [Homo sapiens] | 138 kDa | Synapse | Neuron/glia | Membrane | Synaptogenesis |
| 18 | Calmodulin-like protein 5 (CALML5) | SEQ ID NO 18 | NP_059118.2 calmodulin-like protein 5 [Homo sapiens] | 17 kDa | Synapse | Neuron/glia | cytoplasm | Synaptogenesis |
| 19 | Carbonic anhydrase 1 (CAH1) | SEQ ID NO 19 | NP_001122301.1 carbonic anhydrase 1 isoform a [Homo sapiens] | 17 kDa | Synapse | Neuron/glia | cytoplasm | Synaptogenesis |
| 20 | Caspase-14 (CASP14) | SEQ ID NO 20 | NP_036246.1 caspase-14 precursor [Homo sapiens] | 16 kDa | Synapse | Skin, blood | Blood | Synaptogenesis |
| 21 | Catenin alpha-1 (CTNNA1) | SEQ ID NO 21 | NP_001310912.1 catenin alpha-1 isoform 1 [Homo sapiens] | 29 kDa | Metabolic enzyme | Metabolic enzyme | Cytoplasm | Inflammation |
| 22 | Cathepsin D (CTSD) | SEQ ID NO 22 | NP_001900.1 cathepsin D preproprotein [Homo sapiens] | 28 kDa | Proteolysis | Cell death | extracellular | Apoptosis |
| 23 | Cadherin EGF LAG seven-pass G-type receptor 1 (CELSR1) | SEQ ID NO 23 | NP_055061.1 cadherin EGF LAG seven-pass G-type receptor 1 precursor [Homo sapiens] | 100 kDa | Cell signaling | Brain | Cytoplasm | Synaptogenesis |

FIG. 1C

| 24 | Clusterin (CLU) | SEQ ID NO 24 | NP_001822.3 clusterin preproprotein [Homo sapiens] | | Proteolysis | Ubiquitous | Lysosome, extracellular | Necrosis |
|---|---|---|---|---|---|---|---|---|
| 25 | Coagulation factor XII (F12) | SEQ ID NO 25 | AAA70225.1 coagulation factorXII precursor, partial [Homo sapiens] | 52 kDa | Cell adhesion | Blood | extracellular | Neurodegeneration |
| 26 | Complement C4-A (C4A) | SEQ ID NO 26 | NP_009224.2 complement C4-A isoform 1 preproprotein [Homo sapiens] | 68 kDa | Inflammation | Blood | extracellular | Vascular repair |

FIG. 1C CONTINUED

TABLE 1

| No. | Protein name (Gene name) | Amino acid sequence for detected protein | Accession number | MW (kDa) | Function | Tissue/Cell Specificity | Cell location | Role in brain repair process |
|---|---|---|---|---|---|---|---|---|
| 27 | Complement component C9 (C9) | SEQ ID NO 27 | NP_001728.1 complement component C9 preproprotein [Homo sapiens] | 193 kDa | Inflammation | Blood | extracellular | Innate immunity |
| 28 | Complement factor H (CFH) | SEQ ID NO 28 | AAI42700.1 Complement factor H [Homo sapiens] | 63 kDa | Inflammation | Blood | extracellular | Innate immunity |
| 29 | Complement factor H-related protein 1 (CFHR1) | SEQ ID NO 29 | NP_002104.2 complement factor H-related protein 1 precursor [Homo sapiens] | 139 kDa | Inflammation | Blood | extracellular | Innate immunity |
| 30 | Cullin 7 (CUL7) | SEQ ID NO 30 | NP_001161842.1 cullin-7 isoform 1 | 38 kDa | Inflammation | Blood | extracellular | Innate immunity |
| 31 | Desmocollin-1 (DSC1) | SEQ ID NO 31 | NP_077739.1 desmocollin-1 isoform Dsc1a preproprotein [Homo sapiens] | 191 kDa | Gene expression | Neurons/Epithelia | Nucleus | Vascular repair |
| 32 | Disintegrin and metallopr-oteinase domain-contain-ing protein 8 (ADAM8) | SEQ ID NO 32 | NP_001100.3 disintegrin and met-alloproteinase domain-containing protein 8 isoform 1 precursor [Homo sapiens] | 100 kDa | Cell adhesion | Neurons/Epithelia | Cell membrane | Synaptogenesis |

FIG. 1D

| 33 | Dispatched Homolog 2 (DISP2) | SEQ ID NO 33 | NP_277045.1 protein dispatched homolog 2 [Homo sapiens] | 89 kDa | Proteolysis | Ubiquitous | extracellular | Apoptosis |
|---|---|---|---|---|---|---|---|---|
| 34 | Enolase 1 (ENO1) | SEQ ID NO 34 | NP_001419.1 alpha-enolase isoform 1 [Homo sapiens] | 15 kDa | Lipid binding | Blood | extracellular | Inflammation |
| 35 | Fatty acid-binding prot-ein,epidermal (FABP5) | SEQ ID NO 35 | NP_001435.1 fatty acid-bindingpr otein, epidermal [Homo sapiens] | 144 kDa | Cell signaling | Neuron, other | Dendrite morphology | Synaptogenesis |

FIG. 1D CONTINUED

TABLE 1

| No. | Protein name (Gene name) | Amino acid sequence for detected protein | Accession number | MW (kDa) | Function | Tissue/Cell Specificity | Cell location | Role in brain repair process |
|---|---|---|---|---|---|---|---|---|
| 36 | FERM and PDZ domain-containing protein 4 (FRMPD4) | SEQ ID NO 36 | NP_055543.2 FERM and PDZ domain-containing protein 4 [Homo sapiens] | 42 kDa | Inflammation /Proteolysis | Ubiquitous | extracellular | Inflammation |
| 37 | Fetuin-B (FETUB) | SEQ ID NO 37 | NP_055190.2 fetuin-B isoform 1 precursor [Homo sapiens] | 312 kDa | Extracellular matrix, glucose regulation | | extracellular | Metabolism |
| 38 | Fibrillin-1 (FBN1) | SEQ ID NO 38 | NP_000129.3 fibrillin-1 prepro-protein [Homo sapiens] | 15 kDa | Cell adhesion | Neurons/Epithelia | Cell-cell adhesion | Synaptogenesis |
| 39 | Galectin-7 (LGALS7) | SEQ ID NO 39 | NP_002298.1 galectin-7 [Homo sapiens] | 21 kDa | Metabolic enzyme | Ubiquitous | Intra/extrac-ellular | Metabolism |
| 40 | Gamma-glutamylcyclot-ransferase (GGCT) | SEQ ID NO 40 | NP_076956.1 gamma-glutamylcy clotransferase isoform 1 [Homo sapiens] | 26 kDa | Metabolic enzyme | Ubiquitous | Plasma | Metabolism |
| 41 | Glutathione peroxidase 3 (GPX3) | SEQ ID NO 41 | NP_002075.2 glutathione peroxidase 3 | 21 kDa | Metabolic enzyme | Ubiquitous | Cell membrane | Membrane repair |
| 42 | Group XIIA secretory phospholipase A2 (PLA2G12A) | SEQ ID NO 42 | NP_110448.2 group XIIA secret-ory phospholipase A2 precursor [Homo sapiens] | 45 kDa | Protein binding | Ubiquitous | extracellular | Unknown |

FIG. 1E

| | | | | | | | | |
|---|---|---|---|---|---|---|---|---|
| 43 | Haptoglobin (HP) | SEQ ID NO 43 | NP_005134.1 haptoglobin isoform 1 preproprotein [Homo sapiens] | 60 kDa | Clotting/ Inflammation | Ubiquitous | extracellular | Inflammation |
| 44 | Histidine-rich glycoprotein (HRG) | SEQ ID NO 44 | NP_000403.1 histidine-rich glycoprotein precursor [Homo sapiens] | 432 kDa | Gene regulation | Ubiquitous | Nucleus | Neurogenesis |

FIG. 1E
CONTINUED

TABLE 1

| No. | Protein name (Gene name) | Amino acid sequence for detected protein | Accession number | MW (kDa) | Function | Tissue/Cell Specificity | Cell location | Role in brain repair process |
|---|---|---|---|---|---|---|---|---|
| 45 | Histone-lysine N-methylt-ransferase 2A (KMT2A) | SEQ ID NO 45 | NP_001184033.1 histone-lysine N-methyltransferase 2A isoform 1 precursor [Homo sapiens] | 367 kDa | Cell adhesion | Neuroepithelial cells | Cell Membrane | Synaptogenesis |
| 46 | Kallikrein-plasma (KLKB1) | SEQ ID NO 46 | NP_000883.2 plasma kallikrein isoform 1 preproprotein [Homo sapiens] | 38 kDa | Gene regulation | Ubiquitous | Extracellular | Unknown |
| 47 | Laminin subunit alpha-3 (LAMA3) | SEQ ID NO 47 | NP_937762.2 laminin subunit alpha-3 isoform 1 precursor [Homo sapiens] | 522 kDa | Cell adhesion | Ubiquitous | Cell membrane | Synaptogenesis |
| 48 | Leucine-rich alpha-2 -glycoprotein (LRG1) | SEQ ID NO 48 | NP_443204.1 leucine-rich alpha-2-glycoprotein precursor [Homo sapiens] | 6 kDa | Cell toxicity | Brain | Nuclear, extracellular | Metabolism |
| 49 | Low-density lipoprotein receptor-related protein 2 (LRP2) | SEQ ID NO 49 | NP_004516.2 low-density lipop-rotein receptor-related protein 2 precursor [Homo sapiens] | 122 kDa | Cell adhesion/ Cell death | Astrocytes, macrophages | Cell membrane | Necrosis |
| 50 | Metallothionein-1X (MT1X) | SEQ ID NO 50 | NP_005943.1 metallothionein-1X [Homo sapiens] | 62 kDa | Metabolic enzyme | Ubiquitous | Cytoplasm | Metabolism |

FIG. 1F

| 51 | Multiple epidermal growth factor-like domains prote in 10 (MEGF10) | SEQ ID NO 51 | NP_001243474.1 multiple epide-rmal growth factor-like domains protein 10 isoform a precursor [Homo sapiens] | 256 kDa | Cell adhesion | Neurons | Axon/synapse | Synaptogenesis |
|---|---|---|---|---|---|---|---|---|
| 52 | Neuronal Navigator 3 (NAV3) | SEQ ID NO 52 | NP_001019554.1 neuron navi-gator 3 isoform 1 [Homo sapiens] | 71 kDa | Proteolysis | Ubiquitous | extracellular | Necrosis |

FIG. 1F
CONTINUED

TABLE 1

| No. | Protein name (Gene name) | Amino acid sequence for detected protein | Accession number | MW (kDa) | Function | Tissue/Cell Specificity | Cell location | Role in brain repair process |
|---|---|---|---|---|---|---|---|---|
| 53 | N-acetylmuramoyl-L-alanine amidase (PGLYRP2) | SEQ ID NO 53 | NP_443122.3 N-acetylmuramoyl-L-alanine amidase precursor [Homo sapiens] | 105 kDa | Gene regulation | Ubiquitous | Nucleus, cytoplasm | Neurogenesis |
| 54 | Proprotein convertase subtilisin/kexin type 5 (PCSK5) | SEQ ID NO 54 | AAH12064.1 Proprotein convertase subtilisin/kexin type 5 | 100 kDa | Gene regulation | Ubiquitous | Nucleus | Neurogenesis |
| 55 | Pre-mRNA-splicing factor CWC22 homolog (CWC22) | SEQ ID NO 55 | NP_065994.1 pre-mRNA-splicing factor CWC22 homolog [Homo sapiens] | 207 kDa | Proteolysis | Ubiquitous | extracellular | Synaptogenesis |
| 56 | Protein S100-A11 (S100A11) | SEQ ID NO 56 | NP_005611.1 protein S100-A11 [Homo sapiens] | 152 kDa | Cell signaling | Ubiquitous | Cell Membrane | Unknown |
| 57 | Protein S100-A7 (S100A7) | SEQ ID NO 57 | NP_002954.2 protein S100-A7 [Homo sapiens] | 12 kDa | Cytoskeleton | Ubiquitous | Cell Membrane | Inflammation |
| 58 | Protein S100-A8 (S100A8) | SEQ ID NO 58 | NP_001306125.1 proteinS100-A8 isoform a [Homo sapiens] | 11 kDa | Cytoskeleton | Ubiquitous | Cytoplasm | Synaptogenesis |
| 59 | Protein S100-A9 (S100A9) | SEQ ID NO 59 | NP_002956.1 protein S100-A9 [Homo sapiens] | 11 kDa | Cytoskeleton | Ubiquitous | Cytoplasm | Synaptogenesis |

FIG. 1G

| 60 | Protein SON (SON) | SEQ ID NO 60 | NP_620305.2 protein SON isoform F [Homo sapiens] | 13 kDa | Cytoskeleton | Ubiquitous | Cytoplasm | Synaptogenesis |
|---|---|---|---|---|---|---|---|---|
| 61 | Protein-tyrosine sulfotr-ansferase 1 (TPST1) | SEQ ID NO 61 | NP_003587.1 protein-tyrosine sulfotransferase 1 [Homo sapiens] | 264 kDa | Gene regulation | Ubiquitous | Nucleus | Neurogenesis |

FIG. 1G CONTINUED

TABLE 1

| No. | Protein name (Gene name) | Amino acid sequence for detected protein. | Accession number | MW (kDa). | Function. | Tissue/Cell Specificity. | Cell location. | Role in brain repair process. |
|---|---|---|---|---|---|---|---|---|
| 62 | Scaffold attachment factor B1 (SAFB) | SEQ ID NO 62 | NP_001188267.1 scaffold attach-ment factor B1 isoform 1 [Homo sapiens] | 42 kDa | Metabolism | Ubiquitous | Cytoplasm | Neurogenesis |
| 63 | Serine/threonine-protein kinase TNNI3K (TNNI3K) | SEQ ID NO 63 | NP_057062.1 serine/threonine-protein kinase TNNI3K [Homo sapiens] | 103 kDa | Gene regulation | Ubiquitous | Nucleus | Neurogenesis |
| 64 | Serpin B12 (SERP INB12) | SEQ ID NO 64 | NP_001294857.1 serpin B12 isoform 1 [Homo sapiens] | 93 kDa | Signaling | Cardiac, bone | Nucleus | Vascular repair |
| 65 | Serpin B3 (SERPINB3) | SEQ ID NO 65 | NP_008850.1 serpin B3 [Homo sapiens] | 46 kDa | Proteolysis | Ubiquitous | extracellular | Inflammation |
| 66 | Serpin B4 (SERPINB4) | SEQ ID NO 66 | NP_002965.1 serpin B4 isoform 1 [Homo sapiens] | 45 kDa | Proteolysis | Ubiquitous | extracellular | Inflammation |
| 67 | SLIT-ROBO Rho GT Pase-activating protein 1 (SRGAP1) | SEQ ID NO 67 | NP_065813.1 SLIT-ROBO Rho GTPase-activating protein 1 isoform 1 [Homo sapiens] | 45 kDa | Proteolysis | Ubiquitous | extracellular | Inflammation |
| 68 | Serum amyloid A-1 protein (SAA1) | SEQ ID NO 68 | NP_954630.1 serum amyloid A-1 protein preproprotein [Homo sapiens] | 14 kDa | Inflammation | Ubiquitous | Blood | Inflammation |

FIG. 1H

| | | | | | | | | |
|---|---|---|---|---|---|---|---|---|
| 69 | Serum amyloid A-4 protein (SAA4) | SEQ ID NO 69 | NP_006503.2 serum amyloid A-4 protein precursor [Homo sapiens] | 15 kDa | Inflammation | Ubiquitous | Blood | Inflammation |
| 70 | Serum amyloid P-component (APCS) | SEQ ID NO 70 | NP_001630.1 serum amyloid P-component precursor [Homo sapiens] | 25 kDa | Inflammation | Ubiquitous | Blood | Inflammation |

FIG. 1H
CONTINUED

TABLE 1

| No. | Protein name (Gene name) | Amino acid sequence for detected protein | Accession number | MW (kDa) | Function | Tissue/Cell Specificity | Cell location | Role in brain repair process |
|---|---|---|---|---|---|---|---|---|
| 71 | Small proline-rich protein 2E (SPRR2) | SEQ ID NO 71 | NP_001019380.2 small proline-rich protein 2E [Homo sapiens] | 124 kDa | Signaling | Neuronal | Nucleus, Cytoplasm | Neurogenesis |
| 72 | Pre-mRNA-splicing factor SYF1 (XAB2) | SEQ ID NO 71 | NP_064581.2 pre-mRNA-splicing factor SYF1 [Homo sapiens] | 8 kDa | Cell adhesion | Epithelial cell layers, Skin | Cell membrane | Unknown |
| 73 | Small subunit processome component 20 homolog (UTP20) | SEQ ID NO 73 | NP_055318.2 small subunit processome component 20 homolog [Homo sapiens] | 318 kDa | Metabolism, proteolysis | Ubiquitous | Cytoplasm | Metabolism |
| 74 | Storkhead-box protein 2 (STOX2) | SEQ ID NO 74 | NP_064610.1 storkhead-box protein 2 [Homo sapiens] | 103 kDa | Gene regulation | Nucleus | Neuron | Neurogenesis |
| 75 | Transforming acidic coiled-coil-containing protein 2 (TACC2) | SEQ ID NO 75 | XP_005269446.1 PREDICTED: transforming acidic coiled-coil-containing protein 2 isoform X1 [Homo sapiens] | 309 kDa | Cell signaling | Ubiquitous | Nucleus, cytoplasm | Metabolism |
| 76 | Transmembrane and TPR repeat-containing protein 3 (TMTC3) | SEQ ID NO 76 | NP_861448.2 transmembrane and TPR repeat-containing protein 3 [Homo sapiens] | 104 kDa | Cell signaling | Ubiquitous | Golgi apparatus | Synaptogenesis |

FIG. 1I

| | | | | | | | | |
|---|---|---|---|---|---|---|---|---|
| 77 | Tripartite motif-containing protein 44 (TRIM44) | SEQ ID NO 77 | NP_060053.2 tripartite motif-containing protein 44 [Homo sapiens] | 38 kDa | Cell signaling | Neurons in development | Nucleus | Neurogenesis |
| 78 | Ubiquitin-60S ribosomal protein L40 (UBA52) | SEQ ID NO 78 | NP_003324.1 ubiquitin-60S ribosomal protein L40 isoform 1 precursor [Homo sapiens] | 15 kDa | Gene regulation | Ubiquitous | Nucleus | Metabolism |

FIG. 1I
CONTINUED

TABLE 1

| No. | Protein name (Gene name) | Amino acid sequence for detected protein | Accession number | MW (kDa) | Function | Tissue/Cell Specificity | Cell location | Role in brain repair process |
|---|---|---|---|---|---|---|---|---|
| 79 | von Willebrand factor (VWF) | SEQ ID NO 79 | NP_000543.2 von Willebrandfac-tor preproprotein [Homo sapiens] | 309 kDa | Cell adhesion | Ubiquitous | Cell membrane | Vascular repair |
| 80 | WD repeat-containing protein 87 (WDR87) | SEQ ID NO 80 | NP_001278017.1 WD repeat-containing protein 87 isoform 1 [Homo sapiens] | 333 kDa | Cell signaling | Ubiquitous | Nucleus, cytoplasm | Neurogenesis |
| 81 | Zinc finger protein 652 (ZNF652) | SEQ ID NO 81 | NP_055712.1 zinc finger protein 652 [Homo sapiens] | 70 kDa | Gene regulation | Blood, Heart | Nucleus | Neurogenesis |

FIG. 1J

PROTEIN BIOMARKER INDICATORS OF NEUROLOGICAL INJURY AND/OR DISEASE AND METHODS OF USE THEREOF

PRIORITY

This application is a divisional application of U.S. patent application Ser. No. 16/763,794, filed on May 13, 2020, which is a § 371 (c)(1) application of PCT Application No. PCT/US2018/061372, filed Nov. 15, 2018, which claims priority to claims priority from U.S. provisional patent application No. 62/587,272, filed on Nov. 16, 2017, the disclosures of which are incorporated by reference herein in their entireties.

SEQUENCE LISTING

The Sequence Listing, submitted herewith through Patent Center as an eXtensible Markup Language file (2024-04-25 Sequence Listing 179.0002-US01; created on Apr. 24, 2024; 152,565 bytes), is incorporated by reference herein in its entirety.

BACKGROUND OF THE INVENTION

An estimated 5 million patients per year are evaluated for head injury in the emergency departments of hospitals and medical facilities in the United States. Most of the patients who present with head injury have unclear clinical symptoms and no evidence of intracranial structural damage, such as intracranial bleeding or hemorrhage, when evaluated by computed tomography (CT) imaging of the head. Such patients may be allowed to leave a medical facility, but may suffer from late-emerging symptoms or secondary injury. These subsequent complications, resulting from the head injury, can include rupture of damaged blood vessels, neurodegeneration that may be long term and insidious, or more subtle neurocognitive and neuromotor deficits that develop over time. The persistence of brain inflammation can be one underlying factor that influences these changes over time, and both the innate immune response (e.g., resident microglial cell activation in the brain and infiltrating neutrophils) and the adaptive immune system (e.g., autoantibodies and against damage-related proteins), can play a role in these processes. Such factors generate a different proteomic profile in a patient.

Thus, objective tests are needed that can quickly identify and triage patients who have high or low risk for neurological injury-related symptoms. Current techniques involving single or multiple biomarkers are not sufficient to aid in determining or recommending treatments, for predicting a patient's clinical course. As described herein, methods, compositions, and kits are provided that offer clinical and medical advantages and improvements for identifying, diagnosing, and assessing neurological injury and/or disease, as well as severity thereof, in individuals (patients). The biomarkers and methods described herein provide detection and treatment benefits for patients having brain injury.

SUMMARY OF THE INVENTION

Methods, compositions, and kits as described herein are provided for detecting, identifying, diagnosing, prognosing, assessing, monitoring and/or treating a neurological injury or a brain injury and involve the use of one or more, or a subset of, newly discovered protein biomarkers that are indicative of neurological or brain injury, such as in a patient having traumatic brain injury (TBI). A subset of the protein biomarkers detected in the described methods may contain fewer than all of the proteins set forth in Table 1 herein. For example, a detectable subset may contain, illustratively, two or more, three or more, four or more, five or more, six or more, seven or more, eight or more, nine or more, ten or more, etc., of the protein biomarkers set forth in Table 1 herein. Table 1 lists protein biomarker Nos. 1-81 along with, among other things, identifiers for function, cell and tissue specificity and role in brain repair process.

The proteins set forth in Tables 1 reflect components that result from injury, damage, or destruction of various types of neurological, neuronal and/or brain cells and tissues during injury, and/or that result from such cells and tissues undergoing repair processes subsequent to neurological, neuronal, or brain cell and tissue injury, insult, or damage. These protein biomarkers thus provide superior indicators of neurological, neuronal, or brain injury in a subject. The protein biomarkers are readily detectable in a sample, e.g., a blood or serum sample obtained from a subject, and offer new and assayable proteins that provide distinctive insights into different aspects of neurological injury or disease, or brain injury detection, diagnosis, assessment and in a patient who is or may be in need, as well as being useful for clinical and research purposes.

In an aspect, a method of detecting protein biomarkers, or peptide biomarkers derived therefrom, indicative of neurological or brain injury in a subject detects whether one or more protein biomarkers as set forth in Table 1, or peptide biomarkers derived therefrom, are present in a biological sample obtained from the subject by using a protein detection assay. In one embodiment, the method includes contacting the sample with one or more antibodies or antigen binding fragments thereof that specifically bind to the one or more protein biomarkers, or peptide biomarkers derived therefrom, and detecting binding of the one or more antibodies or antigen binding fragments thereof to the one or more protein biomarkers, or peptide biomarkers derived therefrom, or detecting the one or more protein biomarkers, or peptide biomarkers derived therefrom, by using mass spectrometry or other techniques known in the art.

In another aspect, a method of diagnosing a neurological or brain injury in a subject detects whether one or more protein biomarkers in a protein biomarker panel, or peptide biomarkers derived therefrom, are present in a biological sample obtained from the subject by contacting the sample with one or more antibodies or antigen binding fragments thereof that specifically bind the one or more protein biomarkers, or peptide biomarkers derived therefrom; measuring the levels of the one or more protein biomarkers, or peptide biomarkers derived therefrom, present in the biological sample relative to the levels of the same proteins, or peptide biomarkers derived therefrom, in a control sample; and diagnoses a neurological or brain injury in the subject when the measured levels of the one or more protein biomarkers, or peptide biomarkers derived therefrom, are increased or decreased in the subject's sample relative to the control levels. In an embodiment of this exemplary method, the control levels are one or more of (i) levels of the one or more protein biomarkers, or peptide biomarkers derived therefrom, in a subject not having a neurological or brain injury; (ii) the levels of the one or more protein biomarkers, or peptide biomarkers derived therefrom, in a subject having a more serious or severe form of the neurological or brain injury; or (iii) the levels of the one or more protein biomarkers, or peptide biomarkers derived therefrom, in a subject having a less serious or mild form of the neurological or brain injury.

In embodiments of the methods of any of the foregoing aspects, the neurological or brain injury is traumatic brain injury (TBI). In some embodiments of the method, the TBI is a mild form of TBI (mTBI).

In yet another aspect, a method of assessing whether a therapy or treatment regimen for a neurological or brain injury is effective in a subject includes (i) measuring the amounts or levels of one or more protein biomarkers in a protein biomarker panel, or peptide biomarkers derived therefrom, in a sample obtained from the subject at a first time point prior to initiation of a therapy or treatment regimen for a neurological or brain injury; (ii) measuring the amounts or levels of the one or more protein biomarkers in the protein biomarker panel, or peptide biomarkers derived therefrom, in a sample obtained from the subject at second time point subsequent to the first time point and after the subject has received the therapy or treatment regimen; and (iii) assessing that the therapy or treatment regimen is effective when the measured levels of the one or more protein biomarkers in the protein biomarker panel, or peptide biomarkers derived therefrom, are decreased or trending to normal levels at the second time point compared with the levels of the one or more protein biomarkers in the protein biomarker panel, or peptide biomarkers derived therefrom, measured at the first time point.

In embodiments of the methods of any of the foregoing aspects, the biological sample obtained from the subject is selected from blood, serum, plasma, cerebrospinal fluid (CSF), saliva, urine, sputum, secretions, or tears. In particular embodiments, the sample is blood, serum, or plasma. In embodiments of the methods of any of the foregoing aspects, the one or more protein biomarkers or peptide biomarkers derived therefrom, or levels thereof are detected or measured by an immunoassay, an immunoblotting method, an immunoprecipitation assay, an immunostaining method, a quantitative assay, a immunofluorescent assay, or a chemiluminescence assay. In particular embodiments, the one or more protein biomarkers or peptide biomarkers derived therefrom, or levels thereof are detected or measured by an immunoassay, or an assay-on-a-chip assay (e.g., a microarray multiplex assay). In embodiments of the methods of any of the foregoing aspects, the immunoassay is an enzyme linked immunosorbent assay (ELISA) using one or more antibodies or antigen binding fragments thereof that specifically bind to the one or more protein biomarkers in a protein biomarker panel, or peptide biomarkers derived therefrom. In a particular embodiment, the ELISA is a mesoscale discovery electro-chemiluminescence assay (MSD-ELISA).

In embodiments of the methods of any of the foregoing aspects, the protein biomarker panel includes a plurality of biomarkers and includes (A) a subset of one or more, two or more, three or more, four or more, five or more, six or more, seven or more, eight or more, nine or more, or ten or more, protein biomarkers selected from protein Nos. 1-81 from Table 1; and, optionally, (B) one or more protein biomarkers selected from Brain-Derived Neurotrophic Factor (BDNF), Glial Fibrillary Acidic Protein (GFAP), Intracellular Adhesion Molecule 5 (ICAM5), Synuclein Beta (SNCB), Metallothionein 3 (MT3), Neurogranin (NRGN), Neuron Specific Enolase (NSE), and Aldolase C (ALDOC). In embodiments of the methods of any of the foregoing aspects, a peptide derived from the one or more protein biomarkers is detected or measured. In embodiments of the methods of any of the foregoing aspects, the one or more protein biomarkers, (A), includes a subset of the proteins set forth in Table 1. In embodiments of the methods of any of the foregoing aspects, the one or more protein biomarkers, (A), include a plurality of the proteins set forth in Table 1.

In yet another aspect, a method of assessing whether a therapy or treatment regimen for a neurological or brain injury is effective in a subject includes (a) measuring the amounts or levels of one or more autoantibodies that specifically bind to one or more protein biomarkers in a protein biomarker panel, or peptide biomarkers derived therefrom, in a sample obtained from the subject at a first time point prior to initiation of a therapy or treatment regimen for a neurological or brain injury; (b) measuring the amounts or levels of the one or more autoantibodies in a sample obtained from the subject at second time point subsequent to the first time point and after the subject has received the therapy or treatment regimen; and (c) assessing that the therapy or treatment regimen is effective when the measured levels of the one or more autoantibodies are decreased or trending to normal levels at the second time point compared with the levels of the one or more protein biomarkers, or peptide biomarkers derived therefrom, measured at the first time point.

In another aspect, a method of detecting autoantibodies indicative of a neurological or brain injury in a subject includes contacting a biological sample obtained from the patient with one or more protein biomarkers in a protein biomarker panel, or peptide biomarkers derived therefrom; and detecting specific binding of the one or more protein biomarkers or peptides to one or more antibodies or antigen binding fragments thereof in the sample; wherein the detection of binding is indicative of the presence of one or more autoantibodies against the one or more protein biomarkers or peptides thereof in the subject.

In an embodiment of above methods, the neurological or brain injury is traumatic brain injury (TBI). In embodiments of the above methods, the biological sample is selected from blood, serum, plasma, cerebrospinal fluid (CSF), saliva, urine, sputum, secretions, tears, or tissue. In an embodiment of the above methods, the one or more autoantibodies or levels thereof are detected or measured by an immunoassay, an immunoblotting method, an immunoprecipitation assay, an immunostaining method, a quantitative assay, an immunofluorescent assay, or a chemiluminescence assay. In an embodiment of the above methods, the one or more autoantibodies or levels thereof are detected or measured by an immunoassay or a chip assay.

In an embodiment of the methods of any of the foregoing aspects, detection of the one or more protein biomarkers in a protein biomarker panel, or peptide biomarkers derived therefrom, and/or the amounts or levels thereof in a subject's sample provides a determination and identification of biological or biochemical changes occurring in the subject, which reflect post-injury repair processes selected from inflammation, synaptogenesis, neurogenesis, transdifferentiation, neuronal degeneration, demyelination, glial scar formation, angiogenesis, autophagy, necrosis and/or vascular repair.

In another aspect, a composition includes a solid substrate and a plurality of binding agents immobilized on the substrate, wherein each of the binding agents is immobilized at a different, indexable location on the substrate and the binding agents specifically bind to a plurality of protein biomarkers in a protein biomarker panel, or peptide biomarkers derived therefrom, wherein the protein biomarker panel includes (A) a subset of two or more, three or more, four or more, five or more, six or more, seven or more, eight or more, nine or more, or ten or more, protein biomarkers selected from protein Nos. 1-81 from Table 1; and, optionally, (B) one or more protein biomarkers selected from BDNF, GFAP, ICAM5, SNCB, MT3, NRGN, NSE, and ALDOC. In an embodiment of the composition, the binding agents are labeled with a detectable moiety, optionally wherein the detectable moiety is selected from the group consisting of luminescent agents, chemiluminescent agents, radioisotopes, colorimetric agents; and enzyme-substrate agents. In another embodiment of the composition, the binding agents include one or more antibodies or antigen-binding fragments thereof.

In another aspect, a kit includes a plurality of biomarker binding agents capable of specifically binding to a plurality of protein biomarkers in a protein biomarker panel, or peptide biomarkers derived therefrom, contained in a biological sample obtained from a human patient suspected of having or at risk of having traumatic brain injury, wherein the protein biomarker panel includes (A) a subset of two or more, three or more, four or more, five or more, six or more, seven or more, eight or more, nine or more, or ten or more, protein biomarkers selected from protein Nos. 1-81 from Table 1; and, optionally, (B) one or more protein biomarkers selected from BDNF, GFAP, ICAM5, SNCB, MT3, NRGN, NSE, and ALDOC; and a detecting reagent or a detecting apparatus capable of indicating binding of the binding agents to the one or more proteins or peptides thereof. In an embodiment of the kit, the biological sample is selected from blood, serum, plasma, cerebrospinal fluid (CSF), saliva, urine, sputum, secretions, tears, or tissue.

In particular embodiments of the methods, compositions, or kit of any of the foregoing aspects, the biological sample is a blood, serum, or plasma sample obtained from a human subject.

In an embodiment of the methods, compositions, or kit of any of the foregoing aspects, the peptide derived from the protein biomarker in the protein panel is a post-translationally modified peptide. In some embodiments, the posttranslational modification is citrullination.

In a particular embodiment of the methods, compositions, or kit of any of the foregoing aspects the protein biomarker panel include (B), one or more protein biomarkers selected from BDNF, GFAP, ICAM5, SNCB, MT3, NRGN, NSE, and ALDOC. In another particular embodiment of the methods, compositions, or kit of any of the foregoing aspects, the protein biomarker panel does not include the one or more protein biomarkers from (B).

In the embodiment of the methods, compositions, or kit of any of the foregoing aspects, (A), the subset of protein biomarkers, includes: (i) at least one protein biomarker selected from one or more cell adhesion proteins, one or more cell signaling proteins, a cell toxicity protein, a clotting protein, one or more cytoskeleton proteins, an extracellular matrix protein, a gene expression mediating protein, one or more gene regulation proteins, one or more inflammation proteins, a microtubule trafficking protein, one or more lipid binding proteins, one or more metabolic enzymes, one or more metabolism protein, a protein binding protein, one or more proteolytic proteins, one or more signaling proteins, a structural protein, one or more synapse proteins, and combinations thereof; (ii) at least one protein biomarker found in mammalian cells or tissue, selected from a protein found in astrocytes, one or more proteins found in blood, one or more protein found in blood, heart and liver tissue, one or more proteins found in brain tissue, a protein found in cardiac tissue, a protein found in epithelial tissue, a protein found in interneurons, a protein found in neuroepithelial cells, one or more proteins found in neurons, a protein found in skin tissue, one or more ubiquitous proteins, and combinations thereof; (iii) at least one protein biomarker having a role in a brain repair process selected from one or more apoptosis proteins, one or more inflammation proteins, one or more innate immunity proteins, one or more membrane repair proteins, one or more metabolism proteins, one or more necrosis proteins, one or more neurodegeneration proteins, one or more neurogenesis proteins, one or more synaptogenesis proteins, one or more vascular repair proteins, and combinations thereof; or combinations of (i), (ii), and (iii).

In a particular embodiment of the methods, compositions, or kits of any of the foregoing aspects, the biomarker panel including (A), the subset of protein biomarkers includes one or more cell adhesion proteins are selected from the group consisting of protein Nos. 6, 12, 16, 25, 32, 38, 45, 47, 51, 72, 79, and 49 from Table 1. In another particular embodiment of the methods, compositions, or kits of any of the foregoing aspects, the biomarker panel including (A), the subset of protein biomarkers includes a cell toxicity protein, No 48, from Table 1. 21. In another particular embodiment of the methods, compositions, or kits of any of the foregoing aspects, the biomarker panel including (A), the subset of protein biomarkers includes a clotting protein, No 43, from Table 1. In another particular embodiment of the methods, compositions, or kits of any of the foregoing aspects, the biomarker panel including (A), the subset of protein biomarkers includes one or more cytoskeleton proteins selected from the group consisting of protein Nos. 57, 58, 59, and 60 from Table 1. In another particular embodiment of the methods, compositions, or kits of any of the foregoing aspects, the biomarker panel including (A), the subset of protein biomarkers includes one or more cell signaling proteins selected from the group consisting of protein Nos. 2, 23, 35, 56, 75, 76, 77, and 80 from Table 1. In another particular embodiment of the methods, compositions, or kits of any of the foregoing aspects, the biomarker panel including (A), the subset of protein biomarkers includes a cell toxicity protein, No 48, from Table 1. In another particular embodiment of the methods, compositions, or kits of any of the foregoing aspects, the biomarker panel including (A), the subset of protein biomarkers includes a clotting protein, No 43, from Table 1. In another particular embodiment of the methods, compositions, or kits of any of the foregoing aspects, the biomarker panel including (A), the subset of protein biomarkers includes one or more cytoskeleton proteins selected from the group consisting of protein Nos. 57, 58, 59, and 60 from Table 1. In another particular embodiment of the methods, compositions, or kits of any of the foregoing aspects, the biomarker panel including (A), the subset of protein biomarkers includes an extracellular matrix protein, No. 37, from Table 1. In another particular embodiment of the methods, compositions, or kits of any of the foregoing aspects, the biomarker panel including (A), the subset of protein biomarkers includes a gene expression mediating protein, No. 31, from Table 1. In another particular embodiment of the methods, compositions, or kits of any of the foregoing aspects, the biomarker panel including (A), the subset of protein biomarkers includes one or more gene regulation proteins selected from the group consisting of protein Nos. 7, 15, 44, 46, 53, 54, 61, 63, 74, 78, and 81 from Table 1. In another particular embodiment of the methods, compositions, or kits of any of the foregoing aspects, the biomarker panel including (A), the subset of protein biomarkers includes one or more inflammation proteins selected from the group consisting of protein Nos. 26, 27, 28, 29, 30, 68, 69, 70, and 36 from Table 1. In another particular embodiment of the methods, compositions, or kits of any of the foregoing aspects, the biomarker panel including (A), the subset of protein biomarkers includes a microtubule trafficking protein, No. 13, from Table 1. In another particular embodiment of the methods, compositions, or kits of any of the foregoing aspects, the biomarker panel including (A), the subset of protein biomarkers includes protein No. 5 from Table 1. In another particular embodiment of the methods, compositions, or kits of any of the foregoing aspects, the biomarker panel including (A), the subset of protein biomarkers includes one or more lipid binding proteins selected from the group consisting of protein Nos. 8, 9, 10, and 34 from Table 1. In another particular embodiment of the methods, compositions, or kits of any of the foregoing aspects, the biomarker panel including (A), the subset of protein biomarkers includes one or more metabolic enzymes selected from the group consisting of protein Nos. 4, 11, 14, 21, 39, 40, 41, and 50 from Table 1. In another particular embodiment of the methods, compositions, or kits of any of the foregoing aspects, the biomarker panel including (A), the subset of protein biomarkers includes one or more metabolism proteins selected from protein Nos. 62 and 73 from Table 1. In another particular embodiment of the methods, compositions, or kits of any of the foregoing aspects, the biomarker panel including (A), the subset of protein biomarkers includes a protein binding protein, No. 42, from Table 1. In another particular embodiment of the methods, compositions, or kits of any of the foregoing aspects, the biomarker panel including (A), the subset of protein biomarkers includes one or more proteolytic proteins selected from the group consisting of protein Nos. 3, 22, 24, 33, 52, 55, 65, 66, and 67 from Table 1. In another particular embodiment of the methods, compositions, or kits of any of the foregoing aspects, the biomarker panel including (A), the subset of protein biomarkers includes one or more signaling proteins selected from protein Nos. 64 and 70 from Table 1. In another particular embodiment of the methods, compositions, or kits of any of the foregoing aspects, the biomarker panel including (A), the subset of protein biomarkers includes a structural protein, No. 1 from Table 1. In another particular embodiment of the methods, compositions, or kits of any of the foregoing aspects, the biomarker panel including (A), the subset of protein biomarkers includes one or more synapse proteins selected from the group consisting of protein Nos. 17, 18, 19, and 20 from Table 1.

In another particular embodiment of the methods, compositions, or kits of any of the foregoing aspects, the biomarker panel including (A), the subset of protein biomarkers includes a protein found in astrocytes, No. 49, from Table 1. In another particular embodiment of the methods, compositions, or kits of any of the foregoing aspects, the biomarker panel including (A), the subset of protein biomarkers includes one or more proteins found in blood selected from the group consisting of protein Nos. 8, 9, 10, 26, 27, 28, 29, 30, 34, and 81 from Table 1. In another particular embodiment of the methods, compositions, or kits of any of the foregoing aspects, the biomarker panel including (A), the subset of protein biomarkers includes one or more protein found in blood, heart and liver tissue selected from protein Nos. 14 and 15 from Table 1. In another particular embodiment of the methods, compositions, or kits of any of the foregoing aspects, the biomarker panel including (A), the subset of protein biomarkers includes a protein found in brain tissue, No. 48, from Table 1. In another particular embodiment of the methods, compositions, or kits of any of the foregoing aspects, the biomarker panel including (A), the subset of protein biomarkers includes a protein found in cardiac tissue, No. 64, from Table 1. In another particular embodiment of the methods, compositions, or kits of any of the foregoing aspects, the biomarker panel including (A), the subset of protein biomarkers includes a protein found in epithelial tissue, No. 72, from Table 1. In another particular embodiment of the methods, compositions, or kits of any of the foregoing aspects, the biomarker panel including (A), the subset of protein biomarkers includes proteins selected from the group consisting of protein Nos. 22, 24, and 25 from Table 1. In another particular embodiment of the methods, compositions, or kits of any of the foregoing aspects, the biomarker panel including (A), the subset of protein biomarkers includes a protein found in interneurons, No. 13, from Table 1. In another particular embodiment of the methods, compositions, or kits of any of the foregoing aspects, the biomarker panel including (A), the subset of protein biomarkers includes a protein found in neuroepithelial cells, No. 45, from Table 1. In another particular embodiment of the methods, compositions, or kits of any of the foregoing aspects, the biomarker panel including (A), the subset of protein biomarkers includes one or more proteins found in neurons selected from the group consisting of protein Nos. 74, 35, 12, 17, 18, 19, 71, 51, 77, 7, 31, 32, 38, and 16 from Table 1. In another particular embodiment of the methods, compositions, or kits of any of the foregoing aspects, the biomarker panel including (A), the subset of protein biomarkers includes a protein found in skin tissue, No. 20, from Table 1. In another particular embodiment of the methods, compositions, or kits of any of the foregoing aspects, the biomarker panel including (A), the subset of protein biomarkers includes one or more ubiquitous proteins selected from the group consisting of protein Nos. 1, 2, 3, 4, 6, 11, 23, 33, 36, 37, 39, 40, 41, 42, 43, 44, 46, 47, 50, 52, 53, 54, 55, 56, 57, 58, 59, 60, 61, 62, 63, 65, 66, 67, 68, 69, 70, 73, 75, 76, 78, 79, and 80 from Table 1.

In another particular embodiment of the methods, compositions, or kits of any of the foregoing aspects, the biomarker panel including (A), the subset of protein biomarkers includes at least one protein biomarker with a role in a brain repair process including one or more apoptosis proteins, selected from protein Nos. 22 and 33 from Table 1. In another particular embodiment of the methods, compositions, or kits of any of the foregoing aspects, the biomarker panel including (A), the subset of protein biomarkers includes at least one protein biomarker with a role in a brain repair process including one or more inflammation proteins, selected from the group consisting of protein Nos. 3, 8, 9, 21, 34, 36, 43, 57, 65, 66, 67, 68, 69, and 70 from Table 1. In another particular embodiment of the methods, compositions, or kits of any of the foregoing aspects, the biomarker panel including (A), the subset of protein biomarkers includes at least one protein biomarker with a role in a brain repair process including one or more innate immunity proteins, selected from the group consisting of protein Nos. 27, 28, 29, and 30 from Table 1. In another particular embodiment of the methods, compositions, or kits of any of the foregoing aspects, the biomarker panel including (A), the subset of protein biomarkers includes at least one protein biomarker with a role in a brain repair process including one or more membrane repair proteins, selected protein Nos. 2 and 41 from Table 1. In another particular embodiment of the methods, compositions, or kits of any of the foregoing aspects, the biomarker panel including (A), the subset of protein biomarkers includes at least one protein biomarker with a role in a brain repair process including one or more metabolism proteins, selected from the group consisting of protein Nos. 11, 14, 15, 37, 39, 40, 48, 50, 73, 75, and 78 from Table 1. In another particular embodiment of the methods, compositions, or kits of any of the foregoing aspects, the biomarker panel including (A), the subset of protein biomarkers includes at least one protein biomarker with a role in a brain repair process including one or more necrosis proteins, selected from the group consisting of protein Nos. 24, 49, and 52 from Table 1. In another particular embodiment of the methods, compositions, or kits of any of the foregoing aspects, the biomarker panel including (A), the subset of protein biomarkers includes at least one protein biomarker with a role in a brain repair process including one or more neurodegeneration proteins, selected from the group consisting of protein Nos. 4, 10, and 25 from Table 1. In another particular embodiment of the methods, compositions, or kits of any of the foregoing aspects, the biomarker panel including (A), the subset of protein biomarkers includes at least one protein biomarker with a role in a brain repair process including one or more neurogenesis proteins, selected from the group consisting of protein Nos. 44, 53, 54, 61, 62, 63, 71, 74, 77, 80, and 81 from Table 1. In another particular embodiment of the methods, compositions, or kits of any of the foregoing aspects, the biomarker panel including (A), the subset of protein biomarkers includes at least one protein biomarker with a role in a brain repair process including one or more synaptogenesis proteins, selected from the group consisting of protein Nos. 6, 7, 12, 13, 16, 17, 18, 19, 20, 23, 35, 38, 45, 47, 51, 55, 58, 59, 60, and 76 from Table 1. In another particular embodiment of the methods, compositions, or kits of any of the foregoing aspects, the biomarker panel including (A), the subset of protein biomarkers includes at least one protein biomarker with a role in a brain repair process including one or more vascular repair proteins, selected from the group consisting of protein Nos. 26, 31, 64, and 79 from Table 1.

In yet another particular embodiment of the methods, compositions, or kits of any of the foregoing aspects, the biomarker panel including (A), the subset of protein biomarkers (i) includes a cell adhesion protein, a cell signaling protein, a cell toxicity protein, a clotting protein, a cytoskeleton protein, an extracellular matrix protein, a gene expression mediating protein, a gene regulation protein, an inflammation protein, a microtubule trafficking protein, a lipid binding protein, a metabolic enzyme, a metabolism protein, a protein binding protein, a proteolytic protein, a signaling protein, a structural protein, and a synapse protein. In yet another particular embodiment of the methods, compositions, or kits of any of the foregoing aspects, the biomarker panel including (A), the subset of protein biomarkers (ii) includes a protein found in astrocytes, a protein found in blood, a protein found in blood, heart and liver tissue, a protein found in brain tissue, a protein found in cardiac tissue, a protein found in epithelial tissue, a protein found in interneurons, a protein found in neuroepithelial cells, a protein found in neurons, a protein found in skin tissue, and a ubiquitous protein. In yet another particular embodiment of the methods, compositions, or kits of any of the foregoing aspects, the biomarker panel including (A), the subset of protein biomarkers (iii) includes an apoptosis protein, an inflammation protein, an innate immunity protein, a membrane repair protein, a metabolism protein, a necrosis protein, a neurodegeneration protein, a neurogenesis protein, synaptogenesis protein, and a vascular repair proteins.

In another aspect, methods of treatment for post-TBI outcomes include: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptide biomarkers derived therefrom, in a control sample; stratifying the risk of the patient at one or more time points for post-TBI outcome when the measured levels of the one or more protein biomarkers, or peptide biomarkers derived therefrom, are increased or decreased in the subject's sample relative to the control levels; and if the risk stratification of the patient is high, administering a therapy or an effective amount of a drug specific to the post TBI outcome to treat the patient. In exemplary methods of treatment, the protein biomarker panel includes a plurality of protein biomarkers selected from: (A) a subset of one or more, two or more, three or more, four or more, five or more, six or more, seven or more, eight or more, nine or more, or ten or more, protein biomarkers selected from protein Nos. 1-81 from Table 1; and, optionally, (B) one or more protein biomarkers selected from BDNF, GFAP, ICAM5, SNCB, MT3, NRGN, NSE, and ALDOC. Embodiments of methods of treatment include methods of treatment for post-TBI seizures, post-TBI depression, post-TBI anxiety, post-TBI PTSD, post-TBI sleep disorders, post-TBI headache, post-TBI chronic pain, post-TBI oculomotor deficits, post-TBI attention and cognitive defects, and post-TBI balance and gait problems.

DESCRIPTION OF THE FIGURES

FIGS. 1A-1J presents Table 1, which sets forth the novel protein biomarkers, Nos. 1-81. The protein biomarkers set forth in Table 1 and amino acid sequences in the sequence listing filed herewith, respectively, were discovered in serum samples obtained from patients having traumatic brain injury (TBI) and identified by mass spectroscopy sequencing.

DEFINITIONS

Figure 2:
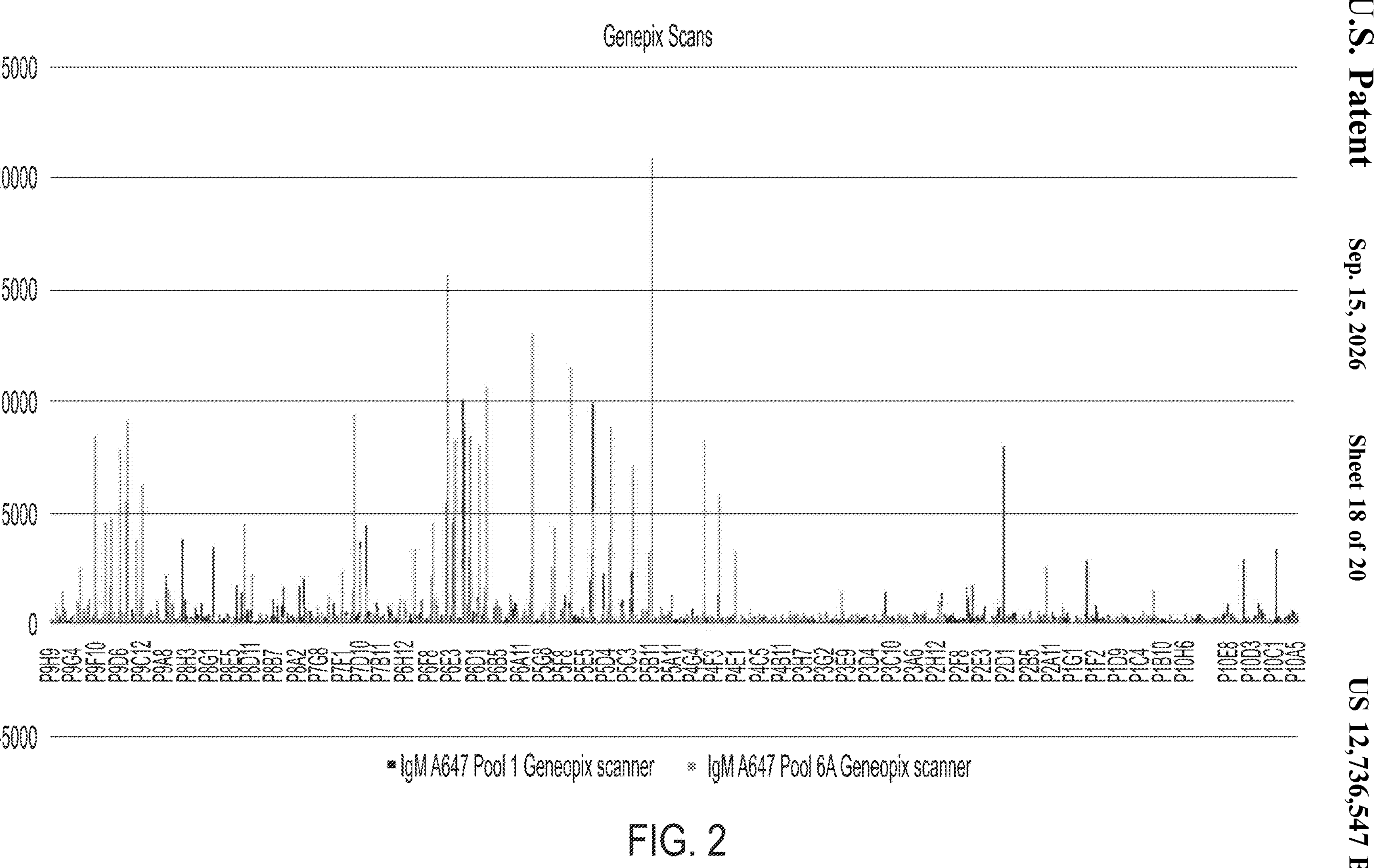
FIG. 2 shows a histogram that graphs the fluorescent signal obtained when individual proteins isolated by two dimensional electrophoresis of serum samples taken from human subjects diagnosed with traumatic brain injury, (TBI), (patient-derived protein arrays), were incubated with serum from a separate cohort of brain-injured patients to allow autoantibody binding, and then probed with anti-human IgM antibody that had a conjugated fluorescent tag (Alexafluor 647). The superimposed orange histograms show the fluorescence intensity of individual proteins from pooled healthy control serum, whereas the blue histograms show the intensity from individual proteins from acutely brain injured individuals. These assays were used to determine which protein fractions showed differential serum protein levels between TBI patients (labelled "IgM A647 Pool 1 Geneopix scanner"—blue histograms) and healthy controls (labelled "IgM A647 Pool 6A Geneopix scanner"—orange histograms). These fractions were subsequently subjected to mass spectroscopy of individual proteins and the sequence of the proteins were identified.

The meaning of certain terms and phrases employed in the specification, examples, and appended claims are provided. The definitions are not meant to be limiting in nature and are intended to provide a clearer understanding of certain aspects and embodiments of the invention.

The term "about" as used herein means, in quantitative terms, plus or minus 5%, or in another embodiment, plus or minus 10%, or in another embodiment, plus or minus 15%, or in another embodiment, plus or minus 20%.

As used herein, the term "antigen" is generally used in reference to any substance that is capable of reacting with an antibody. More specifically, as used herein, the term "antigen" refers to a synthetic peptide, polypeptide, protein or fragment of a polypeptide or protein, or other molecule which elicits an antibody response in a subject, or is recognized and bound by an antibody.

As used herein, the term "autoantibody" or "autoantibodies" refers to an antibody or antibodies produced in an individual, which is/are capable of reacting against an antigenic constituent of the individual's own protein, tissue, or cells (e.g., the antibodies recognize and bind to "self-antigens" or "self-proteins").

As used herein, the term "biomarker" refers to a molecule that is associated either quantitatively or qualitatively with a biological change. Examples of biomarkers include polypeptides, proteins or fragments of a polypeptide or protein; and polynucleotides, such as a gene product, RNA or RNA fragment, or encoding polynucleotides; and other body metabolites. In certain embodiments, a "biomarker" means a compound (e.g., a protein) that is differentially present (i.e., increased or decreased) in a biological sample from a subject or a group consisting of subjects having a first phenotype (e.g., having a disease or condition) as compared to a biological sample from a subject or group consisting of subjects having a second phenotype (e.g., not having the disease or condition or having a less severe version of the disease or condition). A biomarker may be differentially present at any level, but is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); or that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more. Alternatively, the differential presence of a biomarker can be characterized by a -fold change in level including, for example, a level that is decreased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold; or that is increased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold. A biomarker is preferably differentially present at a level that is statistically significant (e.g., a p-value less than 0.05 and/or a q-value of less than 0.10 as determined using, for example, either Welch's T-test or Wilcoxon's rank-sum Test).

The term "one or more of" refers to combinations of various protein biomarkers. The term encompasses 1, 2, 3, 4, 5, 6, 7, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40 . . . to N, where "N" is the total number of protein biomarkers in the particular embodiment. The term also encompasses at least 1, at least 2, at least 3, at least 4, at least 5, at least 6, at least 7, at least 8, at least 9, at least 10, at least 11, at least 12, at least 13, at least 15, 16, 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40 . . . to N. In the biomarker panel of the methods, compositions and kits of the invention, for the one or more biomarkers in (A), N=81. It is understood that the recitation of biomarkers herein includes the phrase "one or more of" the biomarkers and, in particular, includes the "at least 1, at least 2, at least 3" and so forth language in each recited embodiment of a biomarker panel.

The term "biomarker panel" refers to a collection of a plurality of biomarkers grouped together for use in the embodiments of the methods, compositions and kits of the invention. The biomarkers in the panel may be protein biomarkers, or peptide biomarkers derived therefrom. In some embodiments of the methods, compositions or kits of the invention, the protein biomarker panel includes (A) a subset of one or more, two or more, three or more, four or more, five or more, six or more, seven or more, eight or more, nine or more, or ten or more, protein biomarkers selected from protein Nos. 1-81 from Table 1; and, optionally, (B) one or more protein biomarkers selected from BDNF, GFAP, ICAM5, SNCB, MT3, NRGN, NSE, and ALDOC. If the protein biomarker panel contains only one protein from Table 1, then the panel must include (B) one or more protein biomarkers selected from BDNF, GFAP, ICAM5, SNCB, MT3, NRGN, NSE, and ALDOC, so that the panel includes a plurality of biomarkers.

The term "peptide biomarkers derived therefrom" includes the isoforms and/or post-translationally modified forms of any of the foregoing. The invention contemplates the detection, measurement, quantification and/or determination or other analysis of both unmodified and modified (e.g., citrullination or other post-translational modification) proteins/polypeptides/peptides, as well as autoantibodies to any of the foregoing. In certain embodiments, it is understood that reference to the detection, measurement, quantification and/or determination, or other analysis, of a biomarker refers to detection of the protein/polypeptide/peptide (modified and/or unmodified). In other embodiments, reference to the detection, measurement, quantification and/or determination, or other analysis, of a biomarker refers to detection of autoantibodies of the protein/polypeptide/peptide.

"Altered" as used herein can refer to an increase or decrease. An increase is any positive change, e.g., by at least about 5%, 10%, or 20%; by at least about 25%, 50%, 75%, or even by 100%, 200%, 300% or more, including values between the stated percentages. A decrease is a negative change, e.g., a decrease by at least about 5%, 10%, or 20%; by at least about 25%, 50%, 75%; or even an increase by 100%, 200%, 300% or more, including values between the stated percentages.

The term "brain injury" refers to a condition in which the brain (central nervous system or neurological system) is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as a single or repetitive impact (percussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

More specifically, the term "brain injury" refers to a condition that results in central nervous system damage, irrespective of its pathophysiological basis. Among the most frequent origins of a "brain injury" are stroke and traumatic brain injury (TBI).

"Stroke" refers to the destruction of brain tissue as a result of intracerebral hemorrhage or infarction. Stroke is a leading cause of death in the developed world. It may be caused by reduced blood flow and death of tissues in one area of the brain (infarction). Causes of strokes include blood clots that form in the blood vessels in the brain (thrombus) and blood clots or pieces of atherosclerotic plaque or other material that travel to the brain from another location (emboli). Transient ischemic attack (TIA or "mini stroke") is caused by a temporary blockage of blood to the brain, which causes short-term brain dysfunction and is typically resolved within about 24 hours. Bleeding (hemorrhage) within the brain may also cause symptoms that mimic stroke. A "stroke" is classified into hemorrhagic and non-hemorrhagic forms. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

A neurological injury, disorder, disease, or condition refers to any injury to the nervous system or central nervous system, or any disorder of the nervous system or central nervous system. Structural, biochemical, or electrical abnormalities in the brain, spinal cord, nerves of the central nervous system, or other nerves (e.g., peripheral nerves) can result in a range of symptoms. Examples of symptoms of a neurological injury include paralysis, muscle weakness, poor coordination, loss of sensation, seizures, confusion, pain and altered levels of consciousness. Neurological injury or disorders may be assessed by neurological examination and may be treated within neurology and clinical neuropsychology medical specialties. Neurological disorders can be categorized according to the primary location affected, the primary type of dysfunction involved, or the primary cause. Other non-limiting examples of neurological diseases and conditions include neuromuscular disease (e.g., neuropathy, amyotrophic lateral sclerosis (ALS), myopathy, muscular dystrophy, myasthenia gravis), movement disorders (e.g., Parkinson's disease, dystonia, Huntington's disease, Benign essential tremor, Tourette syndrome, cerebral palsy, spasicity), multiple sclerosis, epilepsy, headaches, hemifacial spasm, trigeminal neuralgia (TGN), occipital neuralgia, or brain aneurysm. Neurological tumors can occur at many sites throughout the nervous system and may include pituitary adenoma, acoustic neuroma, meningioma, brain tumor, neurofibromatosis (NF). Other neurological conditions or disorders include Alzheimer's disease and dementias. A brain injury is a non-limiting type of neurological injury, disorder, or condition.

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, medications particularly sedation and anesthesia.

The term "traumatic brain injury" or "TBI" refers to traumatic injuries to the brain which occur when physical trauma causes brain damage. For example, TBI can result from a closed head injury or a penetrating head injury. Symptoms of TBI can be mild (even imperceptible at first) and include headache, confusion, visual disturbances, and nausea. Signs of severe TBI include loss of consciousness exceeding six hours, convulsions, dilation of the pupils, and dizziness. TBI is graded as mild (mild TBI or "mTBI") meaning a brief change in mental status or consciousness), moderate, or severe (meaning an extended period of unconsciousness or amnesia after the injury) on the basis of the level of consciousness or Glasgow coma scale (GCS) score after resuscitation. The GCS scores eye opening (spontaneous=4, to speech=3, to pain=3, none=1), motor response (obeys=6, localizes=5, withdraws=4, abnormal flexion=3, extensor response=2, none=1), and verbal response (oriented=5, confused=4, inappropriate=3, incomprehensible=2, none=1). Mild TBI (GCS 13-15) is in most cases a concussion and there is full neurological recovery, although many of these patients have short-term memory and concentration difficulties. In moderate TBI (GCS 9-13) the patient is lethargic or stuporous, and in severe injury (GCS 3-8) the patient is comatose, unable to open his or her eyes or follow commands.

A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

The term "mild traumatic brain injury (mTBI)" is also commonly known as "concussion" and refers to the occurrence of injury to the head or brain arising from blunt trauma or impact, or forceful motion of the head (acceleration or deceleration forces) causing one or more of the following conditions attributable to head injury: transient confusion, disorientation, or impaired consciousness; dysfunction of memory around the time of injury; or loss of consciousness lasting less than 30 minutes. One or more of the symptoms of mTBI can last a year or more following the initial head or brain injury. While early mTBI symptoms may appear to be mild, they can lead to significant, life-long impairment in an individual's ability to function physically, cognitively and psychologically. While the term "concussion" is used interchangeably with mTBI at times, concussions cover a clinical spectrum and may occur without loss of consciousness. Mild concussion may be present even if there is no external sign of trauma to Lhe head. The spectrum of concussions related to sports injuries are defined by The Quality Standards Subcommittee of the American Academy of Neurology as follows: Grade 1 concussion: transient confusion, no loss of consciousness and duration of mental status abnormalities on examination that resolve in less than 15 minutes; Grade 2 concussion: transient confusion, no loss of consciousness, concussion symptoms or mental status abnormalities on examination that last more than 15 minutes; and Grade 3 concussion: any loss of consciousness, either brief (seconds) or prolonged (minutes). (Centers for Disease Control and Prevention).

As used herein, "secondary brain trauma" refers to damage to the brain of a patient post-acute brain injury, i.e., during the secondary injury phase of a TBI.

As used herein, "acute brain injury" refers to the condition of a patient who has suffered a neurological or brain injury and at a relatively short number of hours, such as 1-10 hours, 1-8 hours, 1-5 hours, 2-5 hours, 3-5 hours, 4-5 hours, and the like from the actual time of the injury.

As used herein, "sub-acute brain injury" refers to the condition of a patient who has suffered a neurological or brain injury from about 2-5 days post injury.

As used herein, "chronic brain injury" refers to the condition of a patient who has suffered a neurological or brain injury from about three days post injury until at least 12 months previously, or from about 1-5 months, or about 1-3 months from the actual time of injury, yet continues to present symptoms of brain injury.

A "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

The term "brain injury biomarker" (BIB), "brain injury protein biomarker", "brain injury biomarker peptide", brain injury biomarker polypeptide," neurological injury biomarker, and the like refer to a protein, including those described herein, that is associated with or indicative of neurological injury or disease and/or brain injury or disease and can be used in methods according to the principles of the invention, e.g., to identify, diagnose and/or detect neurological injury or disease, or brain injury or disease, e.g., mTBI or concussion, in a patient. As described herein, the protein biomarkers include, but are not limited to, the proteins set forth in Table 1, herein.

The term "brain injury biomarkers" also includes the isoforms and/or post-translationally modified forms of any of the foregoing. The invention contemplates the detection, measurement, quantification, determination and the like of both unmodified and modified (e.g., citrullination or other post-translational modification) proteins/polypeptides/peptides, as well as autoantibodies to any of the foregoing. In certain embodiments, it is understood that reference to the detection, measurement, determination, and the like, of a biomarker refers to detection of the protein/polypeptide/peptide (modified and/or unmodified). In other embodiments, reference to the detection, measurement, determination, and the like, of a biomarker refers to detection of autoantibodies of the protein/polypeptide/peptide.

As used herein, the terms "comparing" or "comparison" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, a patient having a neurological injury or brain injury, not having a neurological injury or brain injury, is responding to treatment for a neurological injury or brain injury, is not responding to treatment for the neurological injury or brain injury, is/is not likely to respond to a particular treatment for the neurological injury or brain injury, or having/not having another disease or condition. In a specific embodiment, the term "comparing" refers to assessing whether the level of one or more biomarkers of the invention in a sample from a patient is the same as, more or less than, different from or other otherwise corresponds (or not) to levels/ratios of the same biomarkers in a control sample (e.g., predefined levels/ratios that correlate to healthy individuals, to individuals with no neurological injury or brain injury, to individuals with a lesser degree of neurological injury or brain injury, standard brain injury levels/ratios, etc.). In another embodiment, the terms "comparing" or "comparison" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared.

An "isolated polynucleotide" refers to a nucleic acid (e.g., a DNA or RNA) that is free of the genes which, in the naturally-occurring genome of the organism from which the nucleic acid molecule is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule (mRNA) that is transcribed from a DNA molecule, as well as a recombinant DNA that is part of a hybrid gene encoding one or more additional polypeptide sequences.

Nucleic acid molecules (polynucleotides), which encode the protein biomarkers of Table 1 in the present disclosure, include any nucleic acid molecule that encodes the disclosed proteins, or peptides thereof. Such nucleic acid molecules need not be 100% identical to an endogenous nucleic acid sequence, but will typically exhibit substantial identity. For example, a polynucleotide can have at least about 85% or greater nucleotide sequence identity to a polynucleotide that encodes a protein biomarker of Table 1. Polynucleotides having "substantial identity" to an endogenous sequence are typically capable of hybridizing with at least one strand of a double-stranded nucleic acid molecule. Polynucleotides having "substantial identity" to an endogenous sequence are typically capable of hybridizing with at least one strand of a double-stranded nucleic acid molecule. By "hybridize" is meant pairing to form a double-stranded molecule between complementary polynucleotide sequences (e.g., a gene), or portions thereof, under various conditions of stringency. (See, e.g., Wahl, G. M. and S. L. Berger, 1987, *Methods Enzymol.,* 152:399; Kimmel, A. R., 1987, *Methods Enzymol.,* 152:507).

An "isolated polypeptide" refers to a polypeptide or protein, such as the proteins set forth in Table 1 that has been separated from components that naturally accompany it, or from components that are present during an isolation or purification process. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the disclosure. An isolated polypeptide of the disclosure may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient is improving, not improving, etc. In specific embodiments, the parameter may include the level of one or more biomarkers as described herein. A particular set or pattern of the amounts of one or more biomarkers may indicate that a patient has improved or worsened.

In other embodiments, a particular set or pattern of the amounts of one or more biomarkers may be correlated to a patient being unaffected (i.e., indicates a patient does not have brain injury). In certain embodiments, "indicating," or "correlating," as used according to the invention, may be by any linear or non-linear method of quantifying the relationship between levels/ratios of biomarkers to a standard, control or comparative value for the assessment of the diagnosis, prediction of a neurological injury, brain injury or progression thereof, assessment of efficacy of clinical treatment, identification of a patient who may respond to a particular treatment regime or pharmaceutical agent, monitoring of the progress of treatment, and in the context of a screening assay, for the identification of a therapeutic for the neurological injury or brain injury.

"Magnetic resonance imaging (MRI)" of the brain is a noninvasive and painless neuroimaging test for detailed visualization and analysis that uses a magnetic field and radio waves to produce detailed images of the brain and the brain stem. Unlike a CAT scan (also called a CT scan; computed axial tomography scan), an MRI scan does not use radiation. In some cases, a dye (contrast dye) or contrast material (e.g., iodine, barium, or gadolinium) is used during the MRI to allow visualization of the brain structures (e.g., blood vessels and tissue) more clearly. For example, the dye may show blood flow and areas of inflammation or edema. In some cases, MRI is 3T MRI.

The terms "patient," "individual," or "subject" are used interchangeably herein, and refer to a mammal, particularly, a human. The patient may have a mild, intermediate or severe disease or condition. The patient may be an individual in need of treatment or in need of diagnosis based on particular symptoms or personal or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining or providing a patient sample and/or detecting the level (or amount) of a biomarker(s) in a sample. In one embodiment, the terms refer to obtaining or providing a patient sample and detecting the level of one or more biomarkers in the sample. In another embodiment, the terms "measuring" and "determining" mean detecting the level of one or more biomarkers in a patient sample. The term "measuring" is also used interchangeably throughout with the term "detecting." In certain embodiments, the term is also used interchangeably with the term "quantifying."

The terms "sample," "patient sample," "biological sample," "biologic sample," "biofluid sample," and the like, encompass a variety of sample types obtained from a patient, individual, or subject and can be used in a diagnostic, screening, or monitoring assay. The patient sample may be obtained from a healthy subject or a patient suspected of having or having associated symptoms of neurological injury or brain injury. Moreover, a sample obtained from a patient can be divided, and only a portion may be used for diagnosis. Further, the sample, or a portion thereof, can be stored under conditions to maintain sample for later analysis. The definition of "sample" specifically encompasses blood, serum, plasma, cerebrospinal fluid (CSF) and other liquid samples of biological origin, including, but not limited to, peripheral blood, cord blood, amniotic fluid, tears, urine, saliva, stool, semen, secretions and synovial fluid. A sample also encompasses solid tissue samples, such as a biopsy specimen or cells derived therefrom, or tissue culture cells and the progeny thereof. A tissue or cell sample may be processed (e.g., homogenized, etc.) to produce a suspension or dispersion in liquid form, as discussed below. In a specific embodiment, a sample includes a blood sample. In another embodiment, a sample includes a plasma sample. In yet another embodiment, a serum sample is used. In certain embodiments, a sample includes cerebrospinal fluid.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also include fresh-frozen and/or formalin-fixed, paraffin-embedded tissue blocks, such as blocks prepared from clinical or pathological biopsies, prepared for pathological analysis or study by immunohistochemistry. A sample may be tested immediately after collection, or it may be tested after storage at 4° C., −20° C., or −80° C. Storage times may be 24 hours, 1 week, 1 month, 1 year, 10 years or up to 30 years, depending on stability of the sample and storage conditions.

Various methodologies of the instant invention include a step that involves comparing a value, level, feature, characteristic, property, etc. to a "suitable control," referred to interchangeably herein as an "appropriate control," a "control sample," a "reference" or simply a "control." A "suitable control," "appropriate control," "control sample," "reference" or a "control" is any control or standard familiar to one of ordinary skill in the art useful for comparison purposes. A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "brain injury-positive reference level" of a biomarker means a level of a biomarker that is indicative of brain injury in a subject, and a "brain injury-negative reference level" of a biomarker means a level of a biomarker that is indicative of no brain injury of in a subject.

A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., ELISA, PCR, LC-MS, GC-MS, etc.), where the levels of biomarkers may differ based on the specific technique that is used.

In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the invention may be assayed for levels/ratios in a sample from an unaffected individual (UI) (e.g., no brain injury) or a normal control individual (NC) (both terms are used interchangeably herein). For example, a "suitable control" or "appropriate control" can be a value, level, feature, characteristic, property, ratio, etc. determined prior to performing a therapy (e.g., brain injury treatment) on a patient or a value, level, feature, characteristic, property, ratio, etc. determined prior to disease development (e.g., a baseline test). In yet another embodiment, a protein level/ratio, transcription rate, mRNA level, translation rate, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, ratio, etc. A "suitable control" can be a profile or pattern of levels/ratios of one or more biomarkers of the invention that correlates to brain injury, to which a patient sample can be compared. The patient sample can also be compared to a negative control, i.e., a profile that correlates to not having brain injury.

As used herein, the term "predetermined threshold value of expression" of a biomarker refers to the level of expression of the same biomarker (expressed, for example, in ng/ml) in a corresponding control/normal sample or group consisting of control/normal samples obtained from normal, or healthy, subjects, i.e., subject who do not have brain injury. Further, the term "altered level of expression" of a biomarker in a sample refers to a level that is either below or above the predetermined threshold value of expression for the same biomarker and thus encompasses either high (increased) or low (decreased) expression levels. In particular embodiments, the biomarkers described herein are increased or decreased relative to age-matched (and/or sex-matched) controls.

The terms "specifically binds to," "specific for," and related grammatical variants refer to that binding which occurs between such paired species as enzyme/substrate, receptor/agonist, antibody/antigen, aptamer/target, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. As used herein, the terms "specific binding" or "specifically binding" when used in reference to the interaction of an antibody and a protein or peptide means that the interaction is dependent upon the presence of a particular structure (i.e., the epitope) on the protein.

As used herein, the terms "binding agent specific for" or "binding agent that specifically binds" refers to an agent that binds to a biomarker and does not significantly bind to unrelated compounds. Examples of binding agents that can be effectively employed in the disclosed methods include, but are not limited to, proteins and antibodies, such as monoclonal or polyclonal antibodies, or antigen-binding fragments thereof. In certain embodiments, a binding agent binds a biomarker (e.g., a polypeptide biomarker) with an affinity constant of, for example, greater than or equal to about $1\times10^{-6}$ M.

By "antibody" is meant any immunoglobulin polypeptide, or fragment thereof, having immunogen or antigen binding ability. As used herein, the terms "antibody fragments", "fragment", or "fragment thereof" refer to a portion of an intact antibody, in particular, an immunogen- or antigen-binding portion of the antibody. Examples of antibody fragments include, but are not limited to, linear antibodies; single-chain antibody molecules; Fc or Fc' peptides, Fab and Fab fragments, and multi-specific antibodies formed from antibody fragments. In most embodiments, the terms also refer to fragments that bind an antigen of a target molecule (e.g., a protein biomarker described herein) and can be referred to as "antigen-binding fragments." As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies that specifically binds the target antigen.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

By "an effective amount" is meant the amount of a required to ameliorate the symptoms of a disease relative to an untreated patient. The effective amount of active compound(s) used to practice the invention for therapeutic treatment of brain injury varies depending upon the manner of administration, the age, body weight, and general health of the subject. Ultimately, the attending physician or veterinarian will decide the appropriate amount and dosage regimen. Such amount is referred to as an "effective" amount.

As used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the invention. It is understood that the invention is not limited to the particular methods and components, etc., described herein, as these may vary. It is also to be understood that the terminology used herein is used for the purpose of describing particular embodiments only, and is not intended to limit the scope of the invention.

All publications cited herein are hereby incorporated by reference including all journal articles, books, manuals, published patent applications, and issued patents.

DETAILED DESCRIPTION OF THE INVENTION

The methods, compositions, and kits described herein are based in part on the discovery of new proteins in pooled sera from patients having a neurological injury, such as a brain injury, namely, traumatic brain injury (TBI). The described proteins, or subsets thereof, serve as biomarkers for brain injury and neurodegenerative processes in the brain and spinal cord. Briefly, the proteins were discovered by pooling serum from TBI patients using art-recognized 2D gel electrophoresis (PF2D) protein separation and isolation methods. The separated and resolved proteins were purified and sequenced via mass spectroscopy, thus identifying the new protein biomarkers that are detectable in a patient's sample and that are indicative of neurological or brain injury or disease in a patient undergoing testing. Such a patient may have a neurological injury or disease, such as a brain injury, e.g., TBI, may be suspected of having, or may be at risk of having these conditions.

The identified proteins described herein provide new and advantageous biomarkers that are associated with and/or are indicative of neurological injury or disease, brain injury or disease and/or neurodegenerative processes in the brain and spinal cord of a patient who has, is suspected of having, or is at risk of having the foregoing conditions. These protein biomarkers are presented in Table 1 (FIGS. 1A-1J) and are detected in a biological sample from a patient undergoing testing, evaluation, or analysis using the methods as described herein. Encompassed herein are peptides derived from the amino acid sequences of the proteins of Table 1. Such peptides may be detected in the methods described herein. In embodiments of the methods, the amounts of these detected proteins are increased or decreased in a patient's sample compared to controls, if a patient has a neurological injury such as a brain injury, e.g., TBI. In embodiments, a control is a healthy individual with no neurological injury or disease, or no brain injury or disease, e.g., TBI; or a control is an individual who has a lesser or milder form of a neurological injury or disease, or a brain injury or disease, e.g., TBI; or the control is an individual who has a more serious or severe form of a neurological injury or disease, or a brain injury or disease, e.g., TBI.

In an embodiment, a polynucleotide encoding one or more of the protein biomarkers described herein and presented in Table 1 are detected by the methods described herein.

In an embodiment, autoantibodies directed against one or more of the described protein biomarkers are detected in a biological sample from a patient undergoing testing, evaluation, or analysis using the methods as described herein.

Brain Injury

Traumatic brain injury (TBI) is an injury to the head that involves an acute mechanical event, in which sheer force, blunt force, or linear acceleration or deceleration damages brain tissue. Those having skill in the art appreciate that even individuals who are completely asymptomatic after a head injury can have symptoms or disabilities that develop over time, such as weeks to months after the initial injury. Late emerging deficits in patients can also result from multiple subclinical or sub-concussive head injuries.

The recognition of chronic traumatic encephalopathy (CTE) as a more common long term consequence of concussion or repetitive head injury has further underscored the need for biomarkers that are sensitive to more subtle changes after TBI and for long term changes that are not evident in a patient at the time of injury. The proteins identified and described herein are improved and comprehensive biomarkers, and protein biomarker panels, which are indicative of neurological or brain injury or disease and are informative across the spectrum of injury and recovery. The provision of readily detectable protein biomarkers for TBI identification, diagnosis and outcome is beneficial to both patients and the medical community, because these protein biomarkers are detected by the practice of non-invasive methods in which a biological sample obtained from a patient is assayed as described herein.

For example, in order to follow the course of neural inflammation and subsequent degeneration or repair mechanisms in patients who have or are suspected of having TBI, samples from the patients are examined at several time points after the patient experiences or presents with TBI. The protein biomarker panels, provide biomarkers that are detected in elevated (increased), acutely elevated, or decreased amounts, levels, or concentrations in a patient's sample (e.g., a blood sample from a TBI patient), as well as biomarkers that are involved with chronic degradative processes in the patient. Thus, the methods in which these protein biomarkers are detected allow for determining the evolution of post-TBI responses and for arriving at an accurate molecular and anatomical picture of TBI in a patient across a given time course.

Different types of biomarkers may also reflect the various types of cells that suffer damage in TBI. The biological nature and types of cell damage involved in brain injury such as TBI is as complex and heterogeneous as the brain tissue itself, arguably the most complex tissue in the body. Detection of the described protein biomarkers, subsets thereof, and/or increases or decreases in their amounts, in a patient's sample using the methods described herein allows the determination and identification of changes that occur in an injured patient and that reflect the processes of inflammation, synaptogenesis, glial scar formation, angiogenesis and vascular repair which occur post-injury. In embodiments, different subsets of the protein biomarkers, and/or amounts and alterations thereof, are associated with one or more of these biological features and processes that lead to more or less severe neurological damage or brain injury in an injured patient, such as a TBI patient.

Detection of Biomarkers of Neurological Injury or Disease

Detection by Immunoassay

In specific embodiments of the methods of the invention, the biomarkers in Table 1, Protein Nos. 1-81, can be detected and/or measured by immunoassay. Immunoassay requires biospecific capture reagents/binding agents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

Detection methods suitable for use in the described methods involve, without limitation, traditional immunoassays including, for example, sandwich immunoassays including enzyme-linked immunosorbent assays (ELISA) or fluorescence-based immunoassays, immunoblots, Western Blots (WB), as well as other enzyme immunoassays. Multiplex ELISA assays are also suitable for use. Nephelometry is an assay performed in liquid phase, in which antibodies are in solution. The binding of a protein antigen to a specific antibody results in changes in absorbance, a parameter that is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

In certain embodiments, the expression levels of the biomarkers employed herein are quantified by immunoassay, such as ELISA technology. In specific embodiments, the levels of expression of the biomarkers are determined by contacting the biological sample with antibodies, or antigen binding fragments thereof, that selectively bind to the biomarkers; and detecting binding of the antibodies, or antigen binding fragments thereof, to the biomarkers. In certain embodiments, the binding agents employed in the disclosed methods and compositions are labeled with a detectable moiety.

For example, the level of a biomarker in a sample can be assayed by contacting the biological sample with an antibody, or antigen binding fragment thereof, that selectively binds to the target biomarker (referred to as a capture molecule or antibody or a binding agent), and detecting the binding of the antibody, or antigen-binding fragment thereof, to the biomarker. The detection can be performed using a second antibody to bind to the capture antibody complexed with its target biomarker. A target biomarker can be an entire protein, or a variant or modified form thereof. Kits for the detection of biomarkers as described herein can include pre-coated strip plates, biotinylated secondary antibody, standards, controls, buffers, streptavidin-horse radish peroxidase (HRP), tetramethyl benzidine (TMB), stop reagents, and detailed instructions for carrying out the tests including performing standards.

Embodiments of the invention also provide methods for identifying, detecting, or diagnosing brain injury, e.g., mTBI or concussion, in a subject, wherein the protein biomarkers, or levels, amounts, or concentrations thereof, are detected in a sample obtained from a patient or subject. For example, in one embodiment, methods are provided that include: (a) contacting a biological sample obtained from the subject with a plurality of binding agents that selectively bind to a plurality of the protein biomarkers disclosed herein in Table 1 for a period of time sufficient to form binding agent-biomarker complexes; and (b) detecting binding of the binding agents to the plurality of biomarkers in the sample. In an embodiment, detection is by immunoassay or mass spectrometry or other suitable detection assay or system.

In an embodiment, the levels, amounts, or concentrations of the protein biomarkers, or the level of expression of the protein biomarkers from protein biomarker panel, in the biological sample is determined. In addition to the biomarkers in Table, 1, the biomarker panel may include one or more previously known biomarkers for brain injury. In an embodiment, a plurality of the biomarkers from protein biomarker panel includes (A) one or more, two or more, three or more, four or more, five or more, six or more, seven or more, eight or more, nine or more, ten or more, and the like, or all, or a subset of the proteins presented in Table 1, and optionally (B) one or more protein biomarkers selected from BDNF, GFAP, ICAM5, SNCB, MT3, NRGN, NSE, and ALDOC. International Patent Application Publication No. WO 2018/005791 describes methods, compositions and kits useful in the diagnosis, prognosis and/or assessment of brain injuries and risk for brain injuries, such as hemorrhage, are based upon detection of certain biomarkers including BDNF, GFAP, ICAM5, SNCB, MT3, and NSE. U.S. Pat. No. 9,746,481, describes panels of biomarkers useful in diagnosing brain injuries, which include the biomarkers NRGN, MT3 and GFAP, among others. International Patent Application Publication No. WO 2016/179426 describes methods and kits for detecting or monitoring TBI using ALDOC.

The levels, amounts, or concentrations of the biomarkers, or the levels of expression of the biomarkers, or plurality of biomarkers in the protein biomarker panel, in the patient's sample can be compared with predetermined threshold values. By way of example, the levels of expression of at least one of the plurality of polypeptide biomarkers in the panel which are above or below the predetermined threshold values indicates, for example, a neurological injury or brain injury in the subject. Examples of binding agents that can be effectively employed in such methods include, but are not limited to, antibodies or antigen-binding fragments thereof, aptamers, lectins and the like. Such binding agents may include single chain antibodies and camelid antibodies and may be recombinantly produced.

In a further aspect, embodiments of the invention provide compositions that can be employed in the disclosed methods. In certain embodiments, such compositions include a solid substrate and a plurality of binding agents immobilized on the substrate, wherein each of the binding agents is immobilized at a different, indexable, location on the substrate and the binding agents selectively bind to a plurality of biomarkers in a protein biomarker panel, wherein the panel includes (A) one or more, two or more, three or more, four or more, five or more, six or more, seven or more, eight or more, nine or more, ten or more, and the like, or all, or a subset of the proteins presented in Table 1, and optionally (B) one or more protein biomarkers selected from BDNF, GFAP, ICAM5, SNCB, MT3, NRGN, NSE, and ALDOC. In a specific embodiment, the locations are pre-determined. In one embodiment, the binding agents selectively bind to a plurality of biomarkers of the proteins presented in Table 1 described herein. Binding agents that can be employed in such compositions include, but are not limited to, antibodies, or antigen-binding fragments thereof, aptamers, lectins and the like.

In a related aspect, methods for assessing brain injury, e.g., mTBI or concussion, in a subject are provided, such methods including: (a) contacting a biological sample obtained from the subject with a composition disclosed herein for a period of time sufficient to form binding agent-polypeptide biomarker complexes; (b) detecting binding of the plurality of binding agents to the plurality of polypeptide biomarkers in the protein biomarker panel, thereby determining the levels of expression of the plurality of polypeptide biomarkers in the biological sample; and (c) comparing the levels of expression of the plurality of polypeptide biomarkers in the biological sample with predetermined threshold values, wherein levels of expression of at least one of the plurality of polypeptide biomarkers above or below the predetermined threshold values indicates brain injury status in the subject.

In yet another aspect, embodiments of the invention provide compositions including a solid substrate and a plurality of polypeptide biomarkers in a protein biomarker panel disclosed herein immobilized on the substrate, wherein each of the polypeptide biomarkers is immobilized at a different, indexable, location on the substrate. The protein biomarker panel includes a plurality of biomarkers selected from: (A) a subset of one or more, two or more, three or more, four or more, five or more, six or more, seven or more, eight or more, nine or more, or ten or more, protein biomarkers selected from protein Nos. 1-81 from Table 1; and, optionally, (B) one or more protein biomarkers selected from BDNF, GFAP, ICAM5, SNCB, MT3, NRGN, NSE, and ALDOC.

Although antibodies are useful because of their extensive characterization, any other suitable agent (e.g., a ligand molecule, a peptide, an aptamer, or a small organic molecule) that specifically binds a biomarker of the invention may be optionally used in place of the antibody in the above described immunoassays. For example, an aptamer that specifically binds a biomarker and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

In specific embodiments, the assay performed on the biological sample can include contacting the biological sample with one or more capture agents (e.g., antibodies, peptides, aptamer, etc., combinations thereof) to form a biomarker capture agent complex. The complexes can then be detected and/or quantified. A subject can then be identified as having brain injury based on a comparison of the detected/quantified/measured levels of biomarkers to one or more reference controls as described herein.

In one method, a first, or capture, binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker (or to the bound capture antibody) is then used to detect binding of the polypeptide biomarker to the capture antibody. The detection antibody is preferably conjugated, either directly or indirectly, to a detectable moiety. Examples of detectable moieties that can be employed in such methods include, but are not limited to, chemiluminescent and luminescent agents; fluorophores such as fluorescein, rhodamine and eosin; radioisotopes; colorimetric agents; and enzyme-substrate labels, such as biotin.

In another embodiment, the assay is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate. Suitable microporous membranes include, for example, those described in U.S. Patent Application Publication No. U.S. 2010/0093557 A1. Methods for the automation of immunoassays are well known in the art and include, for example, those described in U.S. Pat. Nos. 5,885,530, 4,981,785, 6,159,750 and 5,358,691.

The presence of several different polypeptide biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations.

In certain embodiments, such methods employ an array, wherein multiple binding agents (for example capture antibodies) specific for multiple biomarkers are immobilized on a substrate, such as a membrane, with each capture agent being positioned at a specific, pre-determined, location on the substrate. Methods for performing assays employing such arrays include those described, for example, in U.S.

Patent Application Publication Nos. US2010/0093557A1 and US2010/0190656A1, the disclosures of which are incorporated by reference herein.

Multiplex arrays in several different formats based on the utilization of, for example, flow cytometry, chemiluminescence or electron-chemiluminescence technology, can be used. Flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis.

In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

Detection by Mass Spectrometry

In one aspect, the described biomarkers may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic co-elution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method includes matrix assisted laser desorption/ionization time-of-flight (MALDI-TOF MS or MALDI-TOF). In another embodiment, method includes MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique includes surface enhanced laser desorption and ionization or "SELDI," as described, for example, in U.S. Pat. Nos. 6,225,047 and 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes including energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that includes antibodies that bind the biomarkers, wash the resin to remove unbound material, elute the biomarkers from the resin and detect the eluted biomarkers by MALDI or by SELDI.

Detection by Electrochemiluminescent Assay

In several embodiments, the described protein biomarkers may be detected by means of an electrochemiluminescent assay developed by Meso Scale Discovery (Gaithersburg, MD). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. Nos. 7,497,997; 7,491,540; 7,288,410; 7,036,946; 7,052,861; 6,977,722; 6,919,173; 6,673,533; 6,413,783; 6,362,011; 6,319,670; 6,207,369; 6,140,045; 6,090,545; and 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

Other Methods for Detecting Biomarkers

The protein biomarkers can be detected by other suitable methods. Detection paradigms that can be employed to this end include optical methods, electrochemical methods (voltammetry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In another embodiment, a sample, such as a sample containing the protein biomarkers described herein, may also be analyzed by means of a biochip. Biochips generally include solid substrates and have a generally planar surface, to which a capture reagent (also called an adsorbent or affinity reagent) is attached. Frequently, the surface of a biochip includes a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, CA.), Invitrogen Corp. (Carlsbad, CA), Affymetrix, Inc. (Fremont, CA), Zyomyx (Hayward, CA), R&D Systems, Inc. (Minneapolis, MN), Biacore (Uppsala, Sweden) and Procognia (Berkshire, UK). Examples of such protein biochips are described in the following patents or published patent applications: U.S. Pat. Nos. 6,537,749; 6,329,209; 6,225,047; 5,242,828; PCT International Publication No. WO 2000/56934; and PCT International Publication No. WO 03/048768.

In a particular embodiment, a microarray chip may be utilized. More specifically, the chip includes a small wafer that carries a collection of binding agents bound to its surface in an orderly pattern, each binding agent occupying a specific position on the chip. The set of binding agents specifically bind to each of the one or more one or more of the biomarkers described herein. In particular embodiments, a few microliters of a biological sample, e.g., a blood, serum, or plasma sample, are dropped on the chip array. Protein biomarkers present in the tested specimen bind to the binding agents which specifically recognize and target the proteins. The subtype and amount of a bound biomarker can be detected and quantified using, for example, a fluorescently-labeled secondary, subtype-specific antibody. In particular embodiments, an optical reader is used for bound biomarker detection and quantification. Thus, a system can include a chip array and an optical reader. In other embodiments, a chip is provided.

Other assays useful for detection of the plurality of protein biomarkers in the protein biomarker panel, or peptide biomarkers derived therefrom, in a biological sample from a patient, e.g., a TBI patient, include single-molecule arrays (SIMOA™), (e.g., as provided by Quanterix, Lexington, MA), which are bead-based detection assays, in which antibody capture molecules are attached to the surface of paramagnetic beads that are capable of detecting thousands of single protein molecules simultaneously and use the same reagents as are used in conventional ELISA assays described herein. Femtomolar (fg/mL) concentrations of proteins can be measured in a SIMOA bead-based immunoassay, which involves arrays of femtoliter-sized reaction chambers that can isolate and detect single protein molecules. Because the array volumes are significantly smaller than those of a conventional ELISA, a rapid increase of fluorescent product is generated if a labeled protein is present.

2-Dimensional Gel Electrophoresis

Two-dimensional electrophoresis (2-D electrophoresis) is a powerful and widely-used biochemical separation technique for the analysis of complex protein mixtures extracted from cells, tissues, or other biological samples. As is appreciated by the skilled practitioner, this technique separates proteins according to two independent properties in two discrete steps: The first dimension step is isoelectric focusing (IEF), which separates proteins according to their isoelectric points (pI). The second dimension step is SDS-polyacrylamide gel electrophoresis (SDS-PAGE), which separates proteins according to their molecular weights (MW). The separated proteins are delineated as spots on a two-dimensional array.

Each spot on the resulting two-dimensional array corresponds to a single protein in a sample. Thousands of different proteins can be separated, and information such as the pI, apparent molecular weight (MW), e.g., in kDa, and the amount of each protein can be obtained. 2-D electrophoresis is a particularly useful as biochemical separation technique tool that may be integral to other developments in separation techniques, image analysis, and protein characterization.

Proteomics, which refers to the systematic separation, identification, and quantification of many proteins simultaneously from a single sample, relies on 2-D electrophoresis and its ability to separate thousands of proteins simultaneously. 2-D electrophoresis can also be used to detect post- and co-translational modifications of protein molecules, which cannot be predicted from the genomic sequence. 2-D electrophoresis is applicable for the analysis of cell differentiation, detection of disease markers in research, drug discovery research, cancer research, purity checks, and microscale protein purification.

2-D Gel Electrophoresis Sample Preparation

For optimal 2-D electrophoresis results, samples must have the right composition for IEF, which means they must be in a solution that does not affect the pI of the proteins to be separated. Accordingly, the samples should not include impurities, especially ionic impurities. Sample preparation can be improved by using specific products to clean-up the samples and provide optimal sample buffers for gel electrophoresis. Streaking resulting from nonspecific oxidation of thiol groups on proteins during 2-D electrophoresis may be addressed by utilizing specific reagents that reduce or eliminate streaking between spots in the gel, especially in the pH range 7 to 11. Such reagents also simplify the spot pattern by reducing the number of spots caused by protein oxidation.

Spot Processing

Gel spots (protein spots) of interest can be picked and analyzed by mass spectrometry (MS) to identify the corresponding proteins. The procedure of picking and digesting spots can be performed manually or semi-automatically by manual transfer of gels and microplates between instruments, or automatically using an integrated workstation. For example, an Ettan Spot Picker is designed to reproducibly spot protein samples and matrix on multiple MALDI MS targets for subsequent analysis by mass spectrometry. An Ettan Digester is an example of a versatile instrument designed to perform in-gel digestion of proteins captured in 2-D gel electrophoresis spots.

2-D Fluorescence Difference Gel Electrophoresis (2-D DIGE)

2-D DIGE is a variant of two-dimensional gel electrophoresis in which an internal standard may be included so that all samples—even those run on different gels—can easily be compared and accurately quantified. An internal standard can virtually eliminate experimental gel-to-gel variation and avoid a need to run technical replicates to confirm differences in protein abundance. 2-D DIGE allows increased throughput and significantly reduced analysis time and cost, dependable results with far fewer 2-D gels (multiplexing two samples per gel with internal standards) and the detection of true differences in protein expression with extremely high statistical confidence.

Briefly, 2-D DIGE is performed by labeling protein samples and internal standard with different fluorescent molecules, such as CyDye DIGE Fluors (GE Healthcare Life Sciences, Piscataway, NJ). The internal standard and one or two samples are run on each gel. Using an internal standard and running multiple samples on the same gel results in fewer gels being run and cost savings. The internal standard is made by pooling all samples in an experiment, and is run on every 2-D DIGE gel. This means that there is a standard for every spot on the gel, and that all gels within the same experiment are quantitatively linked. The internal standard virtually eliminates gel-to-gel variation such that technical replicates are not necessary. A protein sample is first labeled with fluorophores. In contrast to conventional 2D gel electrophoresis in which proteins are post-stained, the protein labeling step in 2-D DIGE is performed before electrophoresis using fluorescent molecules, such as CyDye DIGE Fluors. The first and second dimension electrophoresis steps are performed in a manner similar to that of traditional 2-D electrophoresis, for example using an IEF system, IPG strips, and an electrophoresis system. Image analysis of 2-D DIGE gels is performed with a biomolecular imager that detects multiplex fluorescence, for example, as Typhoon FLA 9500. Analysis (GE Healthcare Life Sciences, Piscataway, NJ) is performed using DeCyder 2-D Differential Analysis Software, optimized for 2-D DIGE.

Autoantibodies

Provided herein are methods for detecting, determining, identifying, measuring, or quantifying, unmodified and modified, e.g., post-translationally modified, citrullinated, glycosylated, etc., proteins in the biomarker panels described herein, as well as autoantibodies to any of the foregoing in a sample obtained from a patient having, suspected of having, or at risk of having a neurological injury or a brain injury. Such autoantibodies directed against a plurality of proteins in a protein biomarker panel, or peptide biomarkers derived therefrom, may be of different immunoglobulin classes and subclasses, e.g., IgM, IgG, IgG1, IgG2a, IgG2b, IgG3, IgG4, etc.). Without wishing to be bound by theory, autoantibodies of the IgM class, or a predominance thereof, that are directed against a plurality of proteins in the protein biomarker panel, or peptide biomarkers derived therefrom, and that are detected in a patient's sample may indicate an early or acute stage of a neurological or brain injury, as this class of antibodies develops early in the immune response. Autoantibodies of the IgG class, or a predominance thereof, detected in a patient's sample may indicate a later or chronic stage of a neurological or brain injury, as this class of antibodies can reflect a sustained or memory immune response.

The determination of the presence of autoantibodies, or of an autoantibody profile, in a patient can be used as a surrogate measurement of the state of the patient prior to brain injury. In addition, the determination of the levels of circulating protein detected at a time after a neurological or brain injury, e.g., a short or a long time period after injury, can be used as a surrogate measurement of the nature or degree of injury. Algorithms that combine the information about the state of the patient prior to injury and the nature or degree of the injury can be used in order to determine how a patient will fare or the outcome of a patient's injury or disease.

The detection of the presence of autoantibodies against protein biomarkers as antigens, as well as the determination of an autoantibody profile, in a subject can be performed, for example, using a platform in which the antigens, e.g., a plurality of proteins in a protein biomarker panel, or peptide biomarkers derived therefrom, are bound to a solid surface or substrate. The surface or substrate is contacted with a sample containing the autoantibodies, which specifically bind to the antigen (e.g., a plurality of proteins in a protein biomarker panel, or peptide biomarkers derived therefrom), and the autoantibodies are detected with a tagged or labeled secondary antibody (e.g., a labeled IgM or IgG antibody) which is detectable. Autoantibody detection can be achieved using, for example, an immunoassay, such as an ELISA format, which includes one or more capture antigens (proteins) and detection antibody(ies).

The platforms used for autoantibody and protein antigen detection may be independent (e.g., iCHIP for autoantibody, MSD ELISA for protein antigens, or any relevant ELISA based platform) or may be combined into a single platform to simultaneously measure both circulating autoantibodies and protein antigens in a sample. By way of example, such dual detection can be accomplished by printing an iCHIP with both the relevant protein antigens and protein antigen-specific capture antibodies (or binding molecules); contacting a subject's sample, e.g., serum, with the printed surface such that circulating autoantibodies bind to the surface bound protein antigens, and circulating protein antigens bind to the surface bound capture antibodies (or binding molecules). A cocktail or mixture of secondary antibodies and detection antibodies can be used for detection of autoantibodies and protein antigens in a sample. In the case where there is a need to measure autoantibodies to the same protein antigen that informs about a disease state or condition, these measurements can we done in two separate chambers. The data from multiple tests can be combined for the purpose of an algorithmic analysis to determine, diagnose, or predict the status of the patient and/or the patient's outcome.

In an embodiment, methods are provided for detecting or diagnosing neurological injury or brain injury in a patient by detecting autoantibodies to a plurality of proteins in a protein biomarker panel, or peptide biomarkers derived therefrom. In one embodiment, autoantibodies to a plurality of protein biomarkers are detected, for example, autoantibodies directed against more than one, more than two, more than three, more than four, more than five, and the like, of the proteins in the protein biomarker panel are detected in a sample. In another embodiment, autoantibodies directed against a subset of the proteins in the protein biomarker panel is detected.

In an embodiment, a method is provided for detecting the presence of autoantibodies that bind to one or more of the protein biomarkers, or a plurality of the protein biomarkers, a protein biomarker panel in a biological sample obtained from the patient. In an embodiment, the detection of the autoantibodies can diagnose, identify, evaluate, or assess a neurological injury or a brain injury, e.g., TBI, in the patient. In an embodiment, the autoantibodies are detected by contacting a biological sample obtained from the patient with one or more of the protein biomarkers of the biomarker panel, or a bindable peptide derived therefrom, and detecting the binding of the protein biomarker or peptide with a labeled or otherwise detectable antibody specific for the protein or peptide, wherein the detection of binding is indicative of the presence of autoantibodies against the protein biomarker or peptide thereof in the patient. In an embodiment, the amount of autoantibodies that specifically bind to the protein or peptide biomarkers can be compared with those in a control subject not having a neurological injury or a brain injury, or to those in a control subject having a lesser or milder form of the neurological injury or brain injury, which assists in determining the status of the neurological injury or the brain injury in the patient undergoing testing.

In another embodiment, a method for assessing the effectiveness of a neurological injury or brain injury therapy or treatment regimen in a patient, in which (a) a baseline level of autoantibodies that bind to a plurality of protein biomarkers in a biomarker panel is established in the subject, by detecting the presence of the autoantibodies in the patient at a first time point prior to therapy or treatment of the patient for the neurological injury or brain injury; (b) detecting (monitoring) the levels of autoantibodies that bind to a plurality of protein biomarkers in a biomarker panel, at a second time point and, optionally at additional time points, after initiation of the therapy or treatment regimen; and (c) comparing the detected levels of the autoantibodies that bind to the plurality of protein biomarkers in a biomarker panel at the second (and/or subsequent time points) to the baseline level of autoantibodies determined at the first time point as described for (a) above. A decrease in the level of autoantibodies detected at the second and/or subsequent time points is indicative of the effectiveness of the neurological injury or brain injury therapy or treatment regimen in the patient. In an embodiment, one or more peptide biomarkers derived from the protein biomarkers in the protein biomarker panel that are bindable by autoantibodies in the sample are detected.

In a further embodiment, a method for qualifying neurological injury or brain injury status, or degree thereof, in a patient is provided, in which the method involves (a) detecting autoantibodies that bind to a plurality of protein biomarkers in a biomarker panel in a biological sample obtained from a patient; (b) measuring the levels of the autoantibodies that bind to the a plurality of protein biomarkers in a biomarker panel in the patient's sample; and (c) comparing the measured levels of the autoantibodies in (b) with levels of autoantibodies in controls, such as samples from subjects having different neurological injury or brain injury status, e.g., no injury, or mild or lesser degrees of injury, so as to qualify the neurological injury or brain injury status, or degree thereof, in the patient. In various embodiments of the method, the neurological or brain injury status involves one or more of the risk of neurological or brain injury, the development of neurological or brain injury, the presence or absence of neurological or brain injury, the stage of neurological or brain injury, the subtype of neurological or brain injury, the prognosis for the patient, and the effectiveness of treatment of neurological or brain injury.

In embodiments of any of the foregoing methods, the binding of autoantibodies to the one or more protein biomarkers, or to peptides thereof, is detected by enzyme-linked immunosorbent assay (ELISA), immunoprecipitation, or immunoblotting. In certain embodiments, the detected protein is one from a plurality of protein biomarkers in a protein biomarker panel, or a subset of the proteins, or a bindable peptide derived from the proteins in the protein biomarker panel.

Protein Biomarker Panels

The described protein biomarkers can be used in panels of several biomarkers in screening, identification, detection, determinative, or diagnostic methods to screen, identify, detect, determine, evaluate, assess and/or qualify brain injury, TBI, or other types of brain injury in an individual (patient). In particular embodiments of the methods, compositions or kits of the invention, the protein biomarker panel includes a plurality of biomarkers and includes (A) a subset of one or more, two or more, three or more, four or more, five or more, six or more, seven or more, eight or more, nine or more, or ten or more, protein biomarkers selected from protein Nos. 1-81 from Table 1; and, optionally, (B) one or more protein biomarkers selected from BDNF, GFAP, ICAM5, SNCB, MT3, NRGN, NSE, and ALDOC.

In some embodiments of the methods, compositions, or kit of any of the foregoing aspects the protein biomarker panel includes (B), one or more protein biomarkers selected from BDNF, GFAP, ICAM5, SNCB, MT3, NRGN, NSE, and ALDOC. In other embodiments, the protein biomarker panel does not include the one or more protein biomarkers from (B). It is understood that if the protein biomarker panel contains only one protein biomarker (A) from protein Nos. 1-81 from Table 1, then the panel must include (B) one or more protein biomarkers selected from BDNF, GFAP, ICAM5, SNCB, MT3, NRGN, NSE, and ALDOC, so that the panel includes a plurality of biomarkers.

In an embodiment of the methods, compositions, or kit of any of the foregoing aspects, the protein biomarker panel includes (A), the subset of protein biomarkers selected from protein Nos. 1-81 from Table 1, including: (i) at least one protein biomarker selected from one or more cell adhesion proteins, one or more cell signaling proteins, a cell toxicity protein, a clotting protein, one or more cytoskeleton proteins, an extracellular matrix protein, a gene expression mediating protein, one or more gene regulation proteins, one or more inflammation proteins, a microtubule trafficking protein, one or more lipid binding proteins, one or more metabolic enzymes, one or more metabolism protein, a protein binding protein, one or more proteolytic proteins, one or more signaling proteins, a structural protein, one or more synapse proteins, and combinations thereof; (ii) at least one protein biomarker found in mammalian cells or tissue, selected from a protein found in astrocytes, one or more proteins found in blood, one or more protein found in blood, heart and liver tissue, one or more proteins found in brain tissue, a protein found in cardiac tissue, a protein found in epithelial tissue, a protein found in interneurons, a protein found in neuroepithelial cells, one or more proteins found in neurons, a protein found in skin tissue, one or more ubiquitous proteins, and combinations thereof; (iii) at least one protein biomarker with a role in a brain repair process selected from one or more apoptosis proteins, one or more inflammation proteins, one or more innate immunity proteins, one or more membrane repair proteins, one or more metabolism proteins, one or more necrosis proteins, one or more neurodegeneration proteins, one or more neurogenesis proteins, one or more synaptogenesis proteins, one or more vascular repair proteins, and combinations thereof; or (iv) combinations of (i), (ii), and (iii). The protein biomarker panels described above for use in the exemplary methods, compositions and kits of the invention optionally include (B) one or more protein biomarkers selected from BDNF, GFAP, ICAM5, SNCB, MT3, NRGN, NSE, and ALDOC. The functions, cell and tissue types and roles in brain repair processes are known in the art. The term "ubiquitous" refers to proteins found in multiple tissues and cells throughout the body.

In some embodiments of the methods, compositions, or kits of the invention, exemplary protein biomarker panels including a plurality of biomarker proteins and optionally including (B) one or more protein biomarkers selected from BDNF, GFAP, ICAM5, SNCB, MT3, NRGN, NSE, and ALDOC, include one of more of the following biomarkers or groups of biomarkers:

- one or more cell adhesion proteins selected from the group consisting of protein Nos. 6, 12, 16, 25, 32, 38, 45, 47, 51, 72, 79, and 49 from Table 1;
- one or more cell signaling proteins selected from the group consisting of protein Nos. 2, 23, 35, 56, 75, 76, 77, and 80 from Table 1;
- a cell toxicity protein, No. 48, from Table 1;
- a clotting protein, No. 43, from Table 1;
- one or more cytoskeleton proteins selected from the group consisting of protein Nos. 57, 58, 59, and 60 from Table 1;
- an extracellular matrix protein, No. 37, from Table 1;
- a gene expression mediating protein, No. 31, from Table 1;
- one or more gene regulation proteins selected from the group consisting of protein Nos. 7, 15, 44, 46, 53, 54, 61, 63, 74, 78, and 81 from Table 1;
- one or more inflammation proteins selected from the group consisting of protein Nos. 26, 27, 28, 29, 30, 68, 69, 70, and 36 from Table 1;
- a microtubule trafficking protein, No. 13, from Table 1;
- protein No. 5 from Table 1;
- one or more lipid binding proteins selected from the group consisting of protein Nos. 8, 9, 10, and 34 from Table 1;
- one or more metabolic enzymes selected from the group consisting of protein Nos. 4, 11, 14, 21, 39, 40, 41, and 50 from Table 1;
- one or more metabolism proteins selected from protein Nos. 62 and 73 from Table 1;
- a protein binding protein, No. 42, from Table 1;
- one or more proteolytic proteins selected from the group consisting of protein Nos. 3, 22, 24, 33, 52, 55, 65, 66, and 67 from Table 1;
- one or more signaling proteins selected from protein Nos. 64 and 70 from Table 1;
- a structural protein, No. 1, from Table 1;
- one or more synapse proteins selected from the group consisting of protein Nos. 17, 18, 19, and 20 from Table 1;
- a protein found in astrocytes, No. 49, from Table 1;
- one or more proteins found in blood selected from the group consisting of protein Nos. 8, 9, 10, 26, 27, 28, 29, 30, 34, and 81 from Table 1;
- one or more protein found in blood, heart and liver tissue selected from protein Nos. 14 and 15 from Table 1;
- a protein found in brain tissue, No. 48, from Table 1;
- a protein found in cardiac tissue, No. 64, from Table 1;
- a protein found in epithelial tissue, No. 72, from Table 1;
- protein Nos. 22, 24, and 25 from Table 1;
- a protein found in interneurons, No. 13, from Table 1;
- a protein found in neuroepithelial cells, No. 45, from Table 1;
- one or more proteins found in neurons selected from the group consisting of protein Nos. 74, 35, 12, 17, 18, 19, 71, 51, 77, 7, 31, 32, 38, and 16 from Table 1;
- a protein found in skin tissue, No. 20, from Table 1;
- one or more ubiquitous proteins selected from the group consisting of protein Nos. 1, 2, 3,4, 6, 11,23, 33, 36, 37, 39, 40, 41, 42, 43, 44, 46, 47, 50, 52, 53, 54, 55, 56, 57, 58, 59, 60, 61, 62, 63, 65, 66, 67, 68, 69, 70, 73, 75, 76, 78, 79, and 80 from Table 1;
- one or more apoptosis proteins with a role in the brain repair process, selected from protein Nos. 22 and 33 from Table 1;
- one or more inflammation proteins with a role in the brain repair process, selected from the group consisting of protein Nos. 3, 8, 9, 21, 34, 36, 43, 57, 65, 66, 67, 68, 69, and 70 from Table 1;
- one or more innate immunity proteins with a role in the brain repair process, selected from the group consisting of protein Nos. 27, 28, 29, and 30 from Table 1;
- one or more membrane repair proteins with a role in the brain repair process, selected protein Nos. 2 and 41 from Table 1;
- one or more metabolism proteins with a role in the brain repair process, selected from the group consisting of protein Nos. 11, 14, 15, 37, 39, 40, 48, 50, 73, 75, and 78 from Table 1; one or more necrosis proteins with a role in the brain repair process, selected from the group consisting of protein Nos. 24, 49, and 52 from Table 1;
- one or more neurodegeneration proteins with a role in the brain repair process, selected from the group consisting of protein Nos. 4, 10, and 25 from Table 1;
- one or more neurogenesis proteins with a role in the brain repair process, selected from the group consisting of protein Nos. 44, 53, 54, 61, 62, 63, 71, 74, 77, 80, and 81 from Table 1;
- one or more synaptogenesis proteins with a role in the brain repair process, selected from the group consisting of protein Nos. 6, 7, 12, 13, 16, 17, 18, 19, 20, 23, 35, 38, 45, 47, 51, 55, 58, 59, 60, and 76 from Table 1; and
- one or more vascular repair proteins with a role in the brain repair process, selected from the group consisting of protein Nos. 26, 31, 64, and 79 from Table 1. Exemplary protein biomarker panels also include combinations of one or more of the above.

In some embodiments of the methods, compositions, or kits of the invention, exemplary protein biomarker panels including a plurality of biomarker proteins and optionally including (B) one or more protein biomarkers selected from BDNF, GFAP, ICAM5, SNCB, MT3, NRGN, NSE, and ALDOC, include one of more of the following biomarkers or groups of biomarkers:

- one or more cell adhesion proteins selected from the group consisting of protein Nos. 12, 16, 25, 38, 51, 79, and 49 from Table 1;
- one or more cell signaling proteins selected from the group consisting of protein Nos. 2, 35, 75, 76, 77, and 80 from Table 1;
- a cell toxicity protein, No. 48, from Table 1;
- a clotting protein, No. 43, from Table 1;
- a gene expression mediating protein, No. 31, from Table 1;

one or more gene regulation proteins selected from the group consisting of protein Nos. 7, 53, 54, 61, and 74 from Table 1;

one or more inflammation proteins selected from the group consisting of protein Nos. 26, 27, 28, 29, 30, and 36 from Table 1;

one or more lipid binding proteins selected from the group consisting of protein Nos. 10, and 34 from Table 1;

one or more metabolic enzymes selected from the group consisting of protein Nos. 39, 40, 41, and 50 from Table 1;

a metabolism protein, No. 73, from Table 1;

one or more proteolytic proteins selected from the group consisting of protein Nos. 22, 24, and 33 from Table 1;

a signaling protein, No. 71, from Table 1;

a synapse protein, No. 17, from Table 1;

a protein found in astrocytes, No. 49, from Table 1;

one or more proteins found in blood selected from the group consisting of protein Nos. 10, 27, 28, 29, 30, and 34, from Table 1;

a protein found in brain tissue, No. 48, from Table 1;

one or more proteins found in neurons selected from the group consisting of protein Nos. 74, 35, 12, 17, 71, 51, 77, 7, 31, 38, and 16 from Table 1;

a protein found in skin tissue, No. 20, from Table 1;

one or more ubiquitous proteins selected from the group consisting of protein Nos. 2, 33, 36, 39, 40, 41, 43, 50, 53, 54, 61, 73, 75, 76, and 79 from Table 1;

one or more apoptosis proteins with a role in the brain repair process, selected from protein Nos. 22 and 33 from Table 1;

one or more inflammation proteins with a role in the brain repair process, selected from the group consisting of protein Nos. 34, 36, and 43 from Table 1;

one or more innate immunity proteins with a role in the brain repair process, selected from the group consisting of protein Nos. 27, 28, 29, and 30 from Table 1;

one or more membrane repair proteins with a role in the brain repair process, selected protein Nos. 2 and 41 from Table 1;

one or more metabolism proteins with a role in the brain repair process, selected from the group consisting of protein Nos. 39, 40, 48, 50, 73, and 75 from Table 1;

one or more necrosis proteins with a role in the brain repair process, selected from the group consisting of protein Nos. 24 and 49 from Table 1;

one or more neurodegeneration proteins with a role in the brain repair process, selected from the group consisting of protein Nos. 10 and 25 from Table 1;

one or more neurogenesis proteins with a role in the brain repair process, selected from the group consisting of protein Nos. 53, 54, 61, 71, 74, and 77 from Table 1;

one or more synaptogenesis proteins with a role in the brain repair process, selected from the group consisting of protein Nos. 7, 12, 13, 16, 17, 35, 38, 51, 55, 58, 59, 60, and 76 from Table 1; and one or more vascular repair proteins with a role in the brain repair process, selected from the group consisting of protein Nos. 31 and 79 from Table 1. Exemplary protein biomarker panels also include combinations of one or more of the above.

In yet another particular embodiment of the methods, compositions, or kits of any of the foregoing aspects, the protein biomarker panel includes (A), the subset of protein biomarkers (i) includes a cell adhesion protein, a cell signaling protein, a cell toxicity protein, a clotting protein, a cytoskeleton protein, an extracellular matrix protein, a gene expression mediating protein, a gene regulation protein, an inflammation protein, a microtubule trafficking protein, a lipid binding protein, a metabolic enzyme, a metabolism protein, a protein binding protein, a proteolytic protein, a signaling protein, a structural protein, and a synapse protein. In yet another particular embodiment of the methods, compositions, or kits of any of the foregoing aspects, the biomarker panel includes (A), the subset of protein biomarkers (ii) includes a protein found in astrocytes, a protein found in blood, a protein found in blood, heart and liver tissue, a protein found in brain tissue, a protein found in cardiac tissue, a protein found in epithelial tissue, a protein found in interneurons, a protein found in neuroepithelial cells, a protein found in neurons, a protein found in skin tissue, and a ubiquitous protein. In yet another particular embodiment of the methods, compositions, or kits of any of the foregoing aspects, the biomarker panel includes (A), the subset of protein biomarkers (iii) includes an apoptosis protein, an inflammation protein, an innate immunity protein, a membrane repair protein, a metabolism protein, a necrosis protein, a neurodegeneration protein, a neurogenesis protein, synaptogenesis protein, and a vascular repair proteins.

In yet another particular embodiment of the methods, compositions, or kits of any of the foregoing aspects, the protein biomarker panel includes a plurality of biomarker proteins selected from one or more of the following: one or more cell adhesion proteins selected from the group consisting of NAV3, MEG10, LAMA3, CELGR1, CLUS, ANXA2, LEG7, ASTN2, VWF, ICAM5, and SPR2E; one or more cell signaling proteins selected from the group consisting of TMTC3, TRI44, and FRMPD4; one or more cell toxicity proteins selected from the group consisting of MT1X and MT3; a clotting protein, HRG; one or more cytoskeleton proteins selected from the group consisting of S100A7, S100A8, S100A9, S100A11, and GFAP; an extracellular matrix protein FBN1; one or more gene regulation proteins selected from the group consisting of A2GL, STOX2, CWC22, SYF1, SON, ZN652, AP3B2 and KMT2A; one or more inflammation proteins selected from the group consisting of FABP5, CAH1, S100A11, SAA1, SAA4, SAMP, HRG, FETB, CO41, CO9, CFAH and FHR1; a microtubule trafficking protein, ABCA2; one or more lipid binding proteins selected from the group consisting of APOA1 and APOB; one or more metabolic enzymes selected from the group consisting of CAH1, ARGI1, GGCT, GPX3, PGRP2, TACC2, NSE and ALDOC; a metabolism protein, FBN1; one or more proteolytic proteins selected from the group consisting of CASPE, ADAM8, and A1AT; a signaling protein TRI44; a structural protein; and a synapse protein, KCNMA1.

In yet another particular embodiment of the methods, compositions, or kits of any of the foregoing aspects, the protein biomarker panel includes a plurality of biomarker proteins selected from one or more of the following: one or more proteins found in astrocytes selected from the group consisting of ASTN2, MEG10, GFAP, and ALDOC; a protein found in blood, APOE; one or more proteins found in blood, heart and liver tissue selected from the group consisting of BD1L1 and NR1H1; a protein found in brain tissue, MT1X; a protein found in cardiac tissue FABP5; a protein found in epithelial tissue, SPR2E; a protein found in interneurons, ABCA2; one or more proteins found in neuroepithelial cells selected from the group consisting of DSC1, LEG7, ASTN2, FRMDP4 and KCNMA1; and one or more proteins found in neurons selected from the group consisting of AP3B2, CELGR1, NAV3, STOX2, TRI44, OR SRGAP1.

In yet another particular embodiment of the methods, compositions, or kits of any of the foregoing aspects, the protein biomarker panel includes a plurality of biomarker proteins selected from one or more of the following: one or more apoptosis proteins selected from the group consisting of CASPE, MEG10 and CATD, one or more inflammation proteins selected from the group consisting of FABP5, CAH1, S100A11, SAA1, SAA4, SAMP, HRG and FETB; one or more innate immunity proteins selected from the group consisting of CO41, CO9, CFAH, and FHR1; one or more membrane repair proteins selected from the group consisting of PLCH1 and PG12A; one or more metabolism proteins selected from the group consisting of ARGI1, GGCT, GPX3, PGRP2, TACC2, and ALDOC; one or more necrosis proteins selected from the group consisting of KLKB1, CATD, and MEG10, one or more neurodegeneration proteins selected from the group consisting of APOE, CLUS, and ENOA, one or more neurogenesis proteins selected from the group consisting of SRGAP1, STOX2, and TRI44; one or more synaptogenesis proteins selected from the group consisting of TMTC3, PCSK5, NAV3, FRMPD4, and LEG7; and one or more vascular repair proteins selected from the group consisting of VWF, TNI3K, FA12, and CUL7.

The phrase "brain injury status" includes any distinguishable manifestation of brain injury, as the case may be, e.g., TBI, mTBI or concussion, including not having brain injury. For example, brain injury status includes, without limitation, brain injury or non-injury in a patient, the stage or severity of brain injury, the progress of brain injury (e.g., progress of brain injury over time), or the effectiveness or response to treatment of brain injury (e.g., clinical follow up and surveillance of brain injury after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the invention may show a statistical difference in different brain injury statuses of at least $p<0.05$, $p<10^{-2}$, $p<10^{-1}$, $p<10^{-4}$ or $p<10^{-1}$. Diagnostic tests that use these biomarkers may show an ROC of at least 0.6, at least about 0.7, at least about 0.8, or at least about 0.9.

The protein biomarkers can be differentially present in UI (NC or non-brain injury) and brain injury, and, therefore, are useful in aiding in the determination of brain injury status. In certain embodiments, the biomarkers are measured in a patient sample using the methods described herein and compared, for example, to predefined biomarker levels/ratios and correlated to brain injury status. In particular embodiments, the measurement(s) may then be compared with a relevant diagnostic amount(s), cut-off(s), or multivariate model scores that distinguish a positive brain injury status from a negative brain injury status. The diagnostic amount(s) represents a measured amount of a biomarker(s) above which or below which a patient is classified as having a particular brain injury status. For example, if the biomarker(s) is/are up-regulated compared to normal, then a measured amount(s) above (or greater than) the diagnostic cutoff(s) provides an assessment of brain injury status. Alternatively, if the biomarker(s) is/are down-regulated, then a measured amount(s) at or below the diagnostic cutoff(s) provides an assessment of brain injury status. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different brain injury statuses, and drawing the cut-off to suit the desired levels of specificity and sensitivity.

In other embodiments, the relative or normalized amounts of biomarkers to each other are useful in aiding in the determination of brain injury status. In certain embodiments, the biomarker ratios are indicative of diagnosis. In other embodiments, a biomarker ratio can be compared to another biomarker ratio in the same sample or to a set of biomarker ratios from a control or reference sample.

Furthermore, in certain embodiments, the values measured for markers of a biomarker panel are mathematically combined and the combined value is correlated to the underlying diagnostic question. Biomarker values may be combined by any appropriate state of the art mathematical method. Mathematical methods useful for correlating a marker combination to a brain injury status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. In one embodiment, the method used in correlating a biomarker combination of the invention, e.g. to assess brain injury, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. of Computational and Graphical Statistics 475-511 (2003); Friedman, J. H., 84 J. of the American Statistical Association 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 Machine Learning 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

Determining Risk of Brain Injury

In a specific embodiment, methods are provided for determining the risk of brain injury, such as TBI, in a patient. Biomarker percentages, ratios, amounts or patterns are characteristic of various risk states, e.g., high, medium or low. The risk of brain injury is determined by measuring the relevant biomarkers in a protein biomarker panel, and then either submitting them to a classification algorithm or comparing them with a reference amount, i.e., a predefined level or pattern of biomarkers that is associated with the particular risk level.

Determining Severity of Brain Injury

In other embodiments, methods are provided for determining the severity of brain injury, e.g., TBI, mTBI, in a patient. Each grade or stage of brain injury likely has a characteristic level of a biomarker or relative levels/ratios of a set of biomarkers (a pattern or ratio). The severity of brain injury is determined by measuring the relevant biomarkers and then either submitting them to a classification algorithm or comparing them with a reference amount, i.e., a predefined level or pattern of biomarkers that is associated with the particular stage. In embodiments, severity of brain injury, e.g., TBI, is further determined by performing neuroimaging analysis to detect more serious or severe damage or insult, such as a change in vascular permeability, such as, for example, blood vessel leakage or intracranial hemorrhage (ICH). Neuroimaging analysis, e.g., using contrast MRI, allows for the detection and visualization of injury such as bleeding, hemorrhage, or other insult or damage to the integrity to the brain or its blood-brain barrier.

Determining Brain Injury Prognosis

In one embodiment, methods are provided for determining the course of brain injury, e.g., TBI, mTBI or concussion, in a patient, e.g., a patient who has experienced repetitive injury. Brain injury course refers to changes in brain injury status over time, including brain injury progression (worsening) and brain injury regression (improvement). Over time, the levels, amounts, or relative levels or amounts (e.g., the pattern or ratio) of the biomarkers change. For example, biomarker "X" may be increased with brain injury, while biomarker "Y" may be decreased with brain injury. Therefore, the trend of these biomarkers, either increased or decreased over time toward neurological injury or brain injury, or recovery, indicates the course of the condition. Accordingly, this method involves measuring the level of one or more biomarkers in a patient at least two different time points, e.g., at a first time point and at a second time point, and comparing the change, if any. The course of brain injury, as well as a determination of injury status, are determined based on these comparisons.

Patient Management

In certain embodiments, methods of identifying or qualifying the status of a neurological injury or a brain injury, e.g., TBI, mTBI or concussion include determining and/or managing patient treatment based on injury status and/or risk. Such management includes the decisions and actions of the medical practitioner, physician, or clinician subsequent to determining brain injury status, e.g., as to TBI, mTBI, or concussion. For example, if a physician makes a diagnosis of TBI, mTBI or concussion, then a certain monitoring regimen would follow. An assessment of the course of brain injury using the described methods may then require a certain treatment or therapy regimen. Profiles of the levels of a set of biomarkers in the biological sample, combined with the age, sex, and acute symptoms of a patient, can provide a risk stratification (high risk, lower risk, or little to no risk likelihood of developing a certain post-TBI outcome, such as seizures, chronic pain, chronic headache, post-concussive symptoms, incomplete recovery assessed by GOS-E<8, sleep disturbances, mild to severe depressive symptoms, mild to severe anxiety, PTSD, chronic headache, poor attention or cognitive performance, or motor deficits). Each model profile with these biomarkers allows the physician to better make an informed decision to direct the TBI, mild TBI, or concussion patient down a treatment pathway tailored for each of the outcomes for which he or she is at high risk. An assessment of the course of brain injury using the described methods may then require a certain treatment or therapy regimen, including identifying an individual's eligibility for clinical trials that investigate therapeutics for a symptom or set of symptoms that results from TBI. Alternatively, a diagnosis of no brain injury might be followed with further testing or monitoring. Also, further tests may be called for if the diagnostic test gives an inconclusive result for neurological or brain injury status.

In one aspect, methods of treatment for post-TBI outcomes include: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptide biomarkers derived therefrom, in a control sample; stratifying the risk of the patient at one or more time points for post-TBI outcome when the measured levels of the one or more protein biomarkers, or peptide biomarkers derived therefrom, are increased or decreased in the subject's sample relative to the control levels; and if the risk stratification of the patient is high, administering a therapy or an effective amount of a drug specific to the post TBI outcome to treat the patient. In the exemplary methods of treatment of the invention, the protein biomarker panel includes a plurality of protein biomarkers selected from: (A) a subset of one or more, two or more, three or more, four or more, five or more, six or more, seven or more, eight or more, nine or more, or ten or more, protein biomarkers selected from protein Nos. 1-81 from Table 1; and, optionally, (B) one or more protein biomarkers selected from BDNF, GFAP, ICAM5, SNCB, MT3, NRGN, NSE, and ALDOC.

In one embodiment, a method treatment of post-TBI seizures includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient at one or more time points for post-TBI seizures when the measured levels of the one or more protein biomarkers, or peptide biomarkers derived therefrom, are increased or decreased in the subject's sample relative to the control levels; and if the risk stratification of the patient is high, administering an effective amount of an antiepileptic drug, such as Keppra, Depakote, or Gabapentin, to the patient.

In another embodiment, a method of treating post-TBI depression includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient for at one or more time points post-TBI depression when the measured levels of the one or more protein biomarkers, or peptide biomarkers derived therefrom, are increased or decreased in the subject's sample relative to the control levels; and if the risk stratification of the patient is high, administering psychotherapy or psychiatry or an effective amount of an antidepressant, such as Prozac or Elavil to the patient.

In another embodiment, a method of treating post-TBI anxiety includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient at one or more time points for post-TBI anxiety when the measured levels of the one or more protein biomarkers, or peptide biomarkers derived therefrom, are increased or decreased in the subject's sample relative to the control levels; and if the risk stratification of the patient is high, administering psychotherapy or psychiatry or an effective amount of an anxiolytic depressant, such as Xanax, Librium, Klonopin, or Ativan to the patient.

In another embodiment, a method of treating post-TBI post-traumatic stress disorder (PTSD) includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient at one or more time points for post-TBI PTSD when the measured levels of the one or more protein biomarkers, or peptide biomarkers derived therefrom, are increased or decreased in the subject's sample relative to the control levels; and if the risk stratification of the patient is high, administering psychotherapy or psychiatry to the patient.

In yet another embodiment, a method of treating post-TBI sleep disorder includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient at one or more time points for post-TBI sleep disorder when the measured levels of the one or more protein biomarkers, or peptide biomarkers derived therefrom, are increased or decreased in the subject's sample relative to the control levels; and if the risk stratification of the patient is high, administering therapy at a sleep clinic or an effective amount of sleep aid, such as melatonin or Advil PM to the patient.

In yet another embodiment, a method of treating post-TBI headache includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient at one or more time points for post-TBI headache when the measured levels of the one or more protein biomarkers, or peptide biomarkers derived therefrom, are increased or decreased in the subject's sample relative to the control levels; and if the risk stratification of the patient is high, administering an effective amount of analgesic, such as ibuprofen, acetaminophen to the patient.

In yet another embodiment, a method of treating post-TBI chronic pain includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient at one or more time points for post-TBI chronic pain when the measured levels of the one or more protein biomarkers, or peptide biomarkers derived therefrom, are increased or decreased in the subject's sample relative to the control levels; and if the risk stratification of the patient is high, administering therapy from a pain specialist or an effective amount of analgesic, such as opioids or cannabidiols to the patient.

In yet another embodiment, a method of treating post-TBI oculomotor deficits includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient at one or more time points for post-TBI oculomotor deficits when the measured levels of the one or more protein biomarkers, or peptide biomarkers derived therefrom, are increased or decreased in the subject's sample relative to the control levels; and if the risk stratification of the patient is high, administering vision therapy to the patient.

In yet another embodiment, a method of treating post-TBI attention and cognitive defects includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient at one or more time points for post-TBI attention and cognitive defects when the measured levels of the one or more protein biomarkers, or peptide biomarkers derived therefrom, are increased or decreased in the subject's sample relative to the control levels; and if the risk stratification of the patient is high, administering cognitive therapy to the patient.

In yet another embodiment, a method of treating post-TBI balance and gait problems includes: detecting whether a plurality of protein biomarkers in a protein biomarker panel, or peptide biomarkers derived therefrom, are present in a biological sample obtained from a patient; measuring the levels of the one or more protein biomarkers, or peptide biomarkers derived therefrom, present in the biological sample relative to the levels of the same proteins, or peptides derived therefrom, in a control sample; stratifying the risk of the patient at one or more time points for post-TBI balance and gait problems when the measured levels of the one or more protein biomarkers, or peptide biomarkers derived therefrom, are increased or decreased in the subject's sample relative to the control levels; and if the risk stratification of the patient is high, administering physical therapy to the patient.

Determining Therapeutic Efficacy of Pharmaceutical Drug

In another embodiment, methods are provided for determining the therapeutic efficacy of a pharmaceutical drug or treatment. These methods are useful in performing clinical trials of the drug, as well as monitoring the progress of a patient undergoing treatment with the drug. Therapy or clinical trials involve administering the drug in a particular regimen. The regimen may involve a single dose of the drug, or multiple doses of the drug over time. The doctor or clinical researcher monitors the effect of the drug on the patient or subject over the course of administration. If the drug has a pharmacological impact on the condition, the amounts or relative amounts (e.g., the pattern, profile or ratio) of one or more of the biomarkers described herein may change toward a neurological injury or brain injury status profile, such as TBI, mTBI or concussion. Therefore, the course of one or more biomarkers in the patient can be followed or monitored during the course of treatment. Accordingly, this method involves measuring one or more biomarkers in a patient receiving drug therapy, and correlating the biomarker levels/ratios with the brain injury status of the patient (e.g., by comparison to predefined levels/ratios of the biomarkers that correspond to different brain injury statuses). An embodiment of this method involves determining the levels/ratios of one or more biomarkers for at least two different time points during a course of drug therapy, e.g., a first time and a second time, and comparing the change in levels/ratios of the biomarkers, if any. For example, the levels/ratios of one or more biomarkers can be measured before and after drug administration or at two different time points during drug administration. The effect of therapy is determined based on these comparisons. If a treatment is effective, then the level/ratio of one or more biomarkers will trend toward normal, while if treatment is ineffective, the level/ratio of one or more biomarkers will trend toward a particular brain injury status.

Generation of Classification Algorithms for Qualifying Brain Injury Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may include raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., brain injury versus no brain injury).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application Publication No. 2002/0138208 A1 to Paulse et al., "Method for analyzing mass spectra."

In other embodiments, the classification models that are created can be formed using unsupervised learning methods. Unsupervised classification attempts to learn classifications based on similarities in the training data set, without preclassifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a UNIX, WINDOWS® or LINUX™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

Kits for the Detection of Biomarkers

In another aspect, embodiments of the invention provide kits for detecting, identifying, assessing, diagnosing, evaluating, or qualifying neurological injury or brain injury or the status thereof, e.g., qualifying TBI, mTBI or concussion, in a patient (subject). The kits are used to detect the protein biomarkers in the protein, or to detect a peptide derived therefrom. In a specific embodiment, the kit is provided as an ELISA kit including antibodies, or an antigen binding fragment thereof, that bind to one or more of, or a subset of, the plurality of protein biomarkers in protein biomarker panel, or a bindable peptide thereof.

The ELISA kit may include a solid support, such as a chip, microtiter plate (e.g., a 96-well plate), beads, or resin having protein biomarker capture reagents (e.g., binding molecules) attached thereon. The kit may further include a means for detecting the protein biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit may be provided as an immuno-chromatography strip including a membrane on which specific antibodies are immobilized, and a means for detecting, e.g., gold particle bound antibodies, where the membrane, includes NC membrane and PVDF membrane. In certain embodiments, neurological injury or brain injury in a patient can be detected or diagnosed by adding to the kit a biological sample (e.g., blood or serum) obtained from the patient and detecting the relevant protein biomarkers that are bound to detectable antibodies, for example, by a method which includes: (i) collecting blood or serum from the patient; (ii) adding the blood or serum from the patient to the diagnostic kit; and, (iii) detecting the biomarkers bound to the antibodies. Use of the kit brings bound antibodies into contact with the patient's sample, such as blood or serum. If protein biomarkers of the protein biomarker panel (or peptides thereof) are present in the sample, the antibodies or antigen binding fragments thereof will bind to the proteins (or peptides thereof) in the sample, and are detected. In other kit and diagnostic embodiments, blood or serum is not collected from the patient (i.e., it is already collected). In other embodiments, the sample may include a tissue sample or a clinical sample, which may be processed prior to contact with detection antibodies.

The kit can also include a washing solution or instructions for making a washing solution, in which the combination of the capture reagents and the washing solution allows capture of the biomarkers on the solid support for subsequent detection by, e.g., antibodies, such as by using an immunoassay or mass spectrometry. In a further embodiment, a kit can include instructions in the form of a label or separate insert. For example, the instructions may inform the user about how to collect the sample, and how to wash a support or substrate on which the particular biomarkers are bound and can be detected, etc. In yet another embodiment, the kit can include one or more containers with control biomarker samples, to be used as standard(s) or references for calibration or normalization.

The practice of the principles of the invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

Without further elaboration, it is believed that one skilled in the art, using the preceding description, can utilize the invention to the fullest extent. The following examples are illustrative only, and not limiting of the remainder of the disclosure or claims in any way whatsoever. In addition, the examples are put forth so as to provide those of ordinary skill in the art with a complete disclosure, description and exemplification of how to make and use the assay, screening, assessing, monitoring and therapeutic methods of the invention, and are not intended to limit the scope of what the inventors regard as their invention.

EXAMPLES

In the following examples, efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Discovery of Biomarkers for Neurological Injury and Disease

The protein biomarkers presented in Table 1, and their amino acids sequences provided in the sequence listing filed herewith, were discovered by pooling serum from patients having TBI using 2D gel electrophoresis (PF2D), which used isoelectric focusing (separation by isoelectric focusing point, pI), followed by hydrophobicity focusing (separation by hydrophobicity). Separated proteins resolved by these methods were purified and sequenced (their amino acid sequences were determined) via mass spectroscopy using routine procedures.

In particular, serum proteins from healthy subjects (control pools) and serum proteins from patients with brain injury (brain injury patient pools) were separated by 2D gel electrophoresis involving isoelectric and hydrophobicity focusing. The resolved individual antigen (protein) fractions were printed (spotted) onto custom microarrays (i.e., microarrayed proteins printed from separated proteins from patient serum) and were probed with serum from human patients having acute to chronic brain injury, as well as with antibodies to known antigens. The reactivities of the antibodies against the proteins in the samples were detected with species-specific anti-IgG or anti-IgM antibodies with fluorescent tags. Candidate fractions were chosen for sequencing. Mass spectroscopy amino acid sequencing and bioinformatics were performed to identify candidate biomarkers that were differentially expressed (i.e., at higher or lower levels, based on fluorescence signals) in patients who had traumatic brain injury compared to controls (subject without TBI or with acute or milder forms of TBI). Several time points after injury were examined using the spotted TBI-protein or healthy control-protein arrays in order to discover the proteome of proteins that were indicative of neurological injury or brain injury, such as TBI.

The protein biomarkers discovered by using the above-designed strategy of proteomic profiling of proteins in serum samples from patients having brain injury, such as TBI, compared with proteins in serum samples from healthy controls, provide concrete and isolatable components (biomarkers) that result from neurological injury or brain injury in subjects with these conditions. These protein biomarker components further provide an indication of the many types of cells and tissues, as well as the cell and tissue damage, that constitute identified and detectable neurological injury-related or brain injury-related components in a patient's sample, such as serum. These biomarker components include proteins whose increased or decreased amounts or levels correlate with neurological injury or brain injury in patients, compared with the amounts or levels of these component proteins in control subjects who do not have the neurological injury or brain injury (e.g., non-TBI subjects).

The isolation and identification methods described above resulted in the identification of new protein biomarkers associated or correlated with, or indicative of, neurological injury or brain injury, such as neuron-enriched proteins, e.g., KCNMA1, FRMDP4, that correlate with synaptogenesis, neural signaling and neuronal survival (Lee et al., 2008, *J. Neurosci.,* 28(53):14546-56). In addition, protein biomarkers of vascular integrity, e.g., von Willebrand factor (vWF), (Gong et al., 2016, *Neurology,* 86(16): S11.001), initially reported in tumor angiogenesis and TBI were detected by the above method. Transcription factors that control injury-related phenotypes and gene expression, e.g., ZNF652, (Callen et al., 2010, *Oncol. Rep,* 23(4):1045-52) were detected in TBI samples, and proteases common to injury and restructuring, such as Cathepsin D (CTSD) and Kallikrein (KRKR1) were also discovered by the above described methods. These proteins identified and described herein are component parts of the cellular machinery that is involved with the normal turnover of cells and tissues. These proteins are also enhanced after tissue injury due to the cascade of injury-related restructuring processes that are activated in cells to remove and clear cell debris, damaged cell fragments, and extracellular matrix in order to allow regrowth and tissue repair in an injured subject. Thus, the proteins presented in Table 1 provide new proteins for use in detection, assessment, diagnostic, and/or prognostic methods as indicators of neurological injury or disease, injury of the nervous system, or brain injury. The methods described using these proteins as neurological or brain injury biomarkers afford more efficient, reliable and economical means and procedures for patients having, suspected of having, or at risk of having various types of neurological injury or disease or brain injury, such as TBI or mTBI, to receive determinative medical assessments, advice, treatments, therapies and outcomes.

Example 3

Detection of Autoantibodies to Proteins to Specific Candidate TBI Biomarkers

Figure 3:
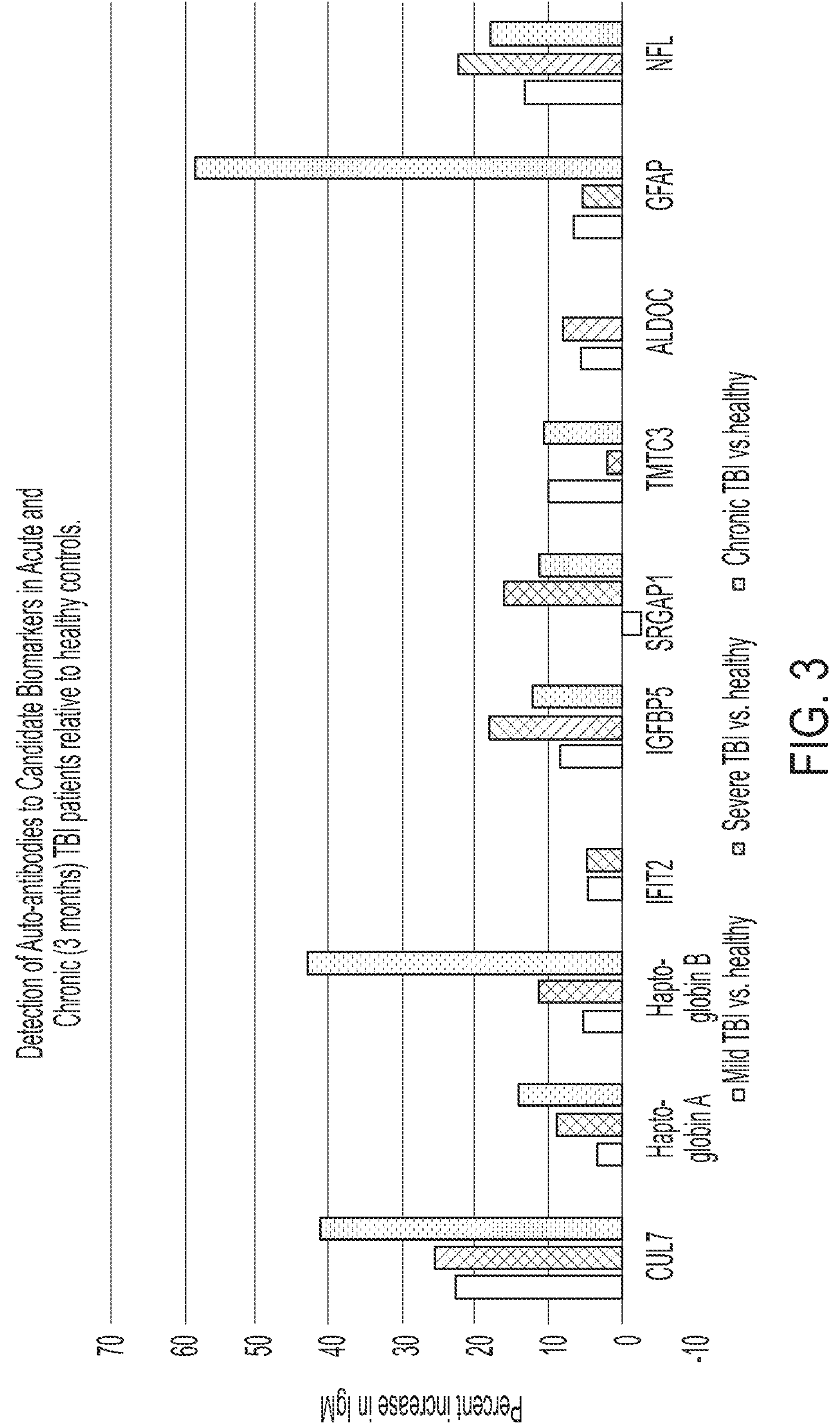
FIG. 3 shows the levels of auto-antibody reactivity against human proteins captured from serum using specific monoclonal antibodies and anti-human IgM detection antibody (electrochemiluminescence detection using MSD read buffer and a Quickplex 120 luminescence reader). Autoantibodies detected include anti-Haptoglobin, anti-Cullin-7, and known auto antibody TBI biomarkers such as anti-GFAP.

Auto-antibodies of proteins to specific candidate TBI biomarker proteins were detected in serum samples in sandwich immunoassays. Serum was diluted 1:20 in 1.5% bovine serum albumin (BSA) containing phosphate buffered saline (PBS blocking buffer) supplemented with Tween-20 detergent. Capture monoclonal antibodies raised against 10 specific human TBI antigen proteins were used to coat 96 well microtiter plates in PBS. Antibody coated wells were washed and incubated in blocking buffer, then incubated with diluted serum. FIG. 3 demonstrates the detected increase in auto-antibody reactivity against human proteins captured from serum using specific monoclonal antibodies and anti-human IgM detection antibody (electrochemiluminescence detection using MSD read buffer and a Quickplex 120 luminescence reader). Auto-antibodies detected include anti-Haptoglobin, anti-Cullin-7, and known auto antibody TBI biomarkers such as anti-GFAP.

Example 4

Figure 4:
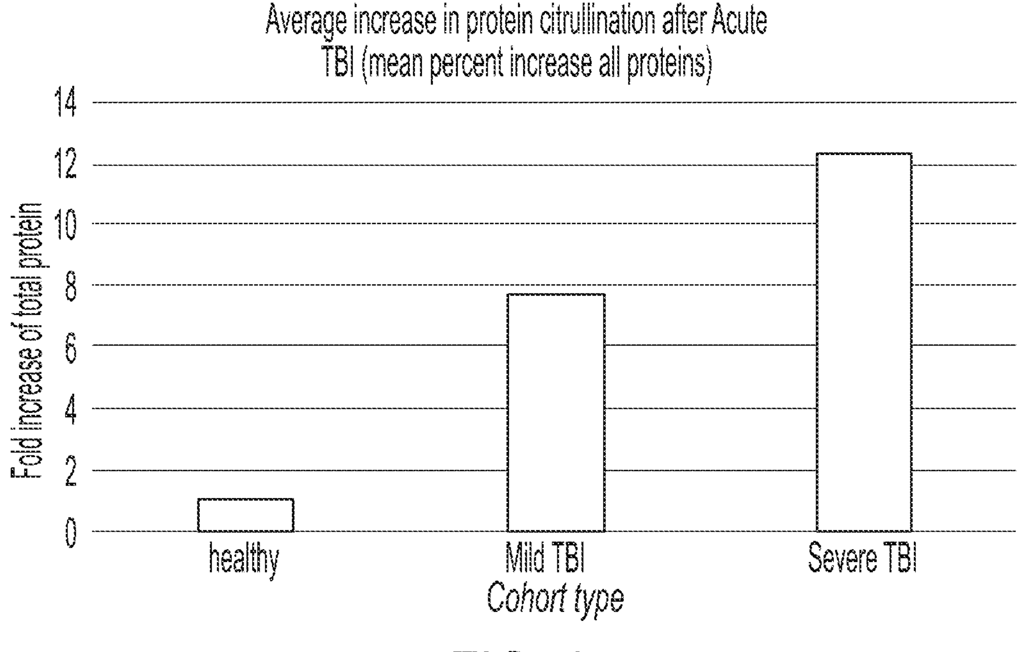
FIG. 4 shows detection of an overall increase in the average percent citrullination levels in TBI serum samples compared to healthy controls, averaged over the 10 proteins tested. Level of citrullination was detected by immunocapture using TBI antigen specific antibodies and detected with anti-citrulline antisera.

Citrullination levels in specific proteins for TBI protein biomarkers were detected in serum samples in sandwich immunoassays as follows. Serum was diluted 1:20 in 1.5% bovine serum albumin (BSA) containing phosphate buffered saline (PBS blocking buffer) supplemented with Tween-20 detergent. Capture monoclonal antibodies raised against 10 specific human TBI antigen proteins were used to coat 96 well microtiter plates in PBS. Antibody coated wells were washed and incubated in blocking buffer, then incubated with diluted serum. FIG. 4 demonstrates the detected increase in citrullinated amino acids for the 10 proteins studied, as detected in the immunocaptured proteins using a citrullination-specific antibody reactivity of the captured human proteins (electrochemiluminescence detection using MSD read buffer and a Quickplex 120 luminescence reader) as an average, based on cohort.

Example 5

Figure 5:
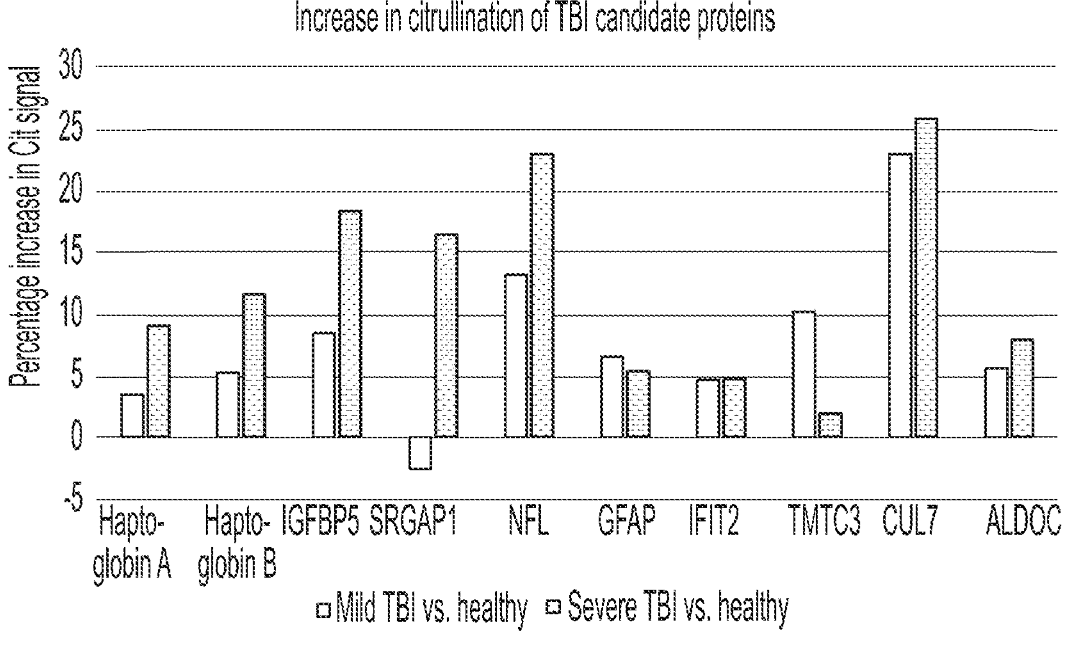
FIG. 5 shows detection of the average percent citrullination levels in TBI serum samples compared to controls, for the proteins tested.

Citrullination levels in specific proteins for TBI protein biomarkers were detected in serum samples in sandwich immunoassays as follows. Serum was diluted 1:20 in 1.5% bovine serum albumin (BSA) containing phosphate buffered saline (PBS blocking buffer) supplemented with Tween-20 detergent. Capture monoclonal antibodies raised against 10 specific human TBI antigen proteins were used to coat 96 well microtiter plates in PBS. Antibody coated wells were washed and incubated in blocking buffer, then incubated with diluted serum. FIG. 5 demonstrates the detected average increase in citrullinated amino acids for the 10 proteins studied, as detected in the immunocaptured proteins using a citrullination specific antibody reactivity of the captured human proteins (electrochemiluminescence detection using MSD read buffer and a Quickplex 120 luminescence reader).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

SEQUENCE LISTING

```
Sequence total quantity: 81
SEQ ID NO: 1             moltype = AA  length = 248
FEATURE                  Location/Qualifiers
source                   1..248
                         mol_type = protein
                         organism = Homo sapiens
SEQUENCE: 1
MERASLIQKA KLAEQAERYE DMAAFMKGAV EKGEELSCEE RNLLSVAYKN VVGGQRAAWR  60
VLSSIEQKSN EEGSEEKGPE VREYREKVET ELQGVCDTVL GLLDSHLIKE AGDAESRVFY  120
LKMKGDYYRY LAEVATGDDK KRIIDSARSA YQEAMDISKK EMPPTNPIRL GLALNFSVFH  180
YEIANSPEEA ISLAKTTFDE AMADLHTLSE DSYKDSTLIM QLLRDNLTLW TADNAGEEGG  240
EAPQEPQS                                                          248

SEQ ID NO: 2             moltype = AA  length = 1684
FEATURE                  Location/Qualifiers
source                   1..1684
                         mol_type = protein
                         organism = Homo sapiens
SEQUENCE: 2
MSYWNLEKRN CVQYRRHFLV DNSVFHVERC MSVMQSGTQM IKLKRGTKGL VRLFYLDEHR  60
TRLRWRPSRK SEKAKILIDS IYKVTEGRQS EIFHRQAEGN FDPSCCFTIY HGNHMESLDL  120
ITSNPEEART WITGLKYLMA GISDEDSLAK RQRTHDQWVK QTFEEADKNG DGLLNIEEIH  180
QLMHKLNVNL PRRKVRQMFQ EADTDENQGT LTFEEFCVFY KMMSLRRDLY LLLLSYSDKK  240
DHLTVEELAQ FLKVEQKMNN VTTDYCLDII KKFEVSEENK VKNVLGIEGF TNFMRSPACD  300
IFNPLHHEVY QDMDQPLCNY YIASSHNTYL TGDQLLSQSK VDMYARVLQE GCRCVEVDCW  360
DGPDGEPVVH HGYTLTSKIL FRDVVETINK HAFVKNEFPV ILSIENHCSI QQQRKIAQYL  420
KGIFGDKLDL SSVDTGECKQ LPSPQSLKGK ILVKGKKLPY HLGDDAEEGE VSDEDSADEI  480
EDECKFKLHY SNGTTEHQVE SFIRKKLESL LKESQIRDKE DPDSFTVRAL LKATHEGLNA  540
HLKQSPDVKE SGKKSHGRSL MTNFGKHKKT TKSRSKSYST DDEEDTQQST GKEGGQLYRL  600
GRRRKTMKLC RELSDLVVYT NSVAAQDIVD DGTTGNVLSF SETRAHQVVQ QKSEQFMIYN  660
QKQLTRIYPS AYRIDSSNFN PLPYWNAGCQ LVALNYQSEG RMMQLNRAKF KANGNCGYVL  720
KPQQMCKGTF NPFSGDPLPA NPKKQLILKV ISGQQLPKPP DSMFGDRGEI IDPFVEVEII  780
GLPVDCCKDQ TRVVDDNGFN PVWEETLTFT VHMPEIALVR FLVWDHDPIG RDFVGQRTVT  840
FSSLVPGYRH VYLEGLTEAS IFVHITINEI YGKNRQLQGL KGLFNKNPRH SSSENNSHYV  900
RKRSIGDRIL RRTASAPAKG RKKSKMGFQE MVEIKDSVSE ATRDQDGVLR RTTRSLQARP  960
VSMPVDRNLL GALSLPVSET AKDIEGKENS LEDKDGRRKG KASIKDPHFL NFNKKLSSSS  1020
SALLHKDTSQ GDTIVSTAHM SVTGEQLGMS SPRGGRTTSN ATSNCQENPC PSKSLSPKQH  1080
LAPDPVVNPT QDLHGVKIKE KGNPEDFVEG KSILSGSVLS HSNLEIKNLE GNRGKGRAAT  1140
SFSLSDVSML CSDIPDLHST AILQESVISH LIDNVTLTNE NEPGSSISAL IGQFDETNNQ  1200
ALTVVSHLHN TSVMSGHCPL PSLGLKMPIK HGFCKGKSKS SFLCSSPELI ALSSSETTKH  1260
ATNTVYETTC TPISKTKPDD DLSSKAKTAA LESNLPGSPN TSRGWLPKSP TKGEDWETLK  1320
SCSPASSPDL TLEDVIADPT LCFNSGESSL VEIDGESENL SLTTCEYRRE GTSQLASPLK  1380
LKYNQGVVEH FQRGLRNGYC KETLRPSVPE IFNNIQDVKT QSISYLAYQG AGFVHNHFSD  1440
SDAKMFQTCV PQQSSAQDMH VPVPKQLAHL PLPALKLPSP CKSKSLGDLT SEDIACNFES  1500
KYQCISKSFV TTGIRDKKGV TVKTKSLEPI DALTEQLRKL VSFDQEDNCQ VLYSKQDANQ  1560
LPRALVRKLS SRSQSRVRNI ASRAKEKQEA NKQKVPNPSN GAGVVLRNKP SAPTPAVNRH  1620
STGSYIAGYL KNTKGGGLEG RGIPEGACTA LHYGHVDQFC SDNSVLQTEP SSDDKPEIYF  1680
LLRL                                                              1684

SEQ ID NO: 3             moltype = AA  length = 2436
FEATURE                  Location/Qualifiers
source                   1..2436
                         mol_type = protein
                         organism = Homo sapiens
SEQUENCE: 3
MGFLHQLQLL LWKNVTLKRR SPWVLAFEIF IPLVLFFILL GLRQKKPTIS VKEVSFYTAA  60
PLTSAGILPV MQSLCPDGQR DEFGFLQYAN STVTQLLERL DRVVEEGNLF DPARPSLGSE  120
LEALRQHLEA LSAGPGTSGS HLDRSTVSSF SLDSVARNPQ ELWRFLTQNL SLPNSTAQAL  180
LAARVDPPEV YHLLFGPSSA LDSQSGLHKG QEPWSRLGGN PLFRMEELLL APALLEQLTC  240
TPGSGELGRI LTVPESQKGA LQGYRDAVCS GQAAARARRF SGLSAELRNQ LDVAKVSQQL  300
GLDAPNGSDS SPQAPPPRRL QALLGDLLDA QKVLQDVDVL SALALLLPQG ACTGRTPGPP  360
ASGAGGAANG TGAGAVMGPN ATAEEGAPSA AALATPDTLQ GQCSAFVQLW AGLQPILCGN  420
NRTIEPEALR RGNMSSLGFT SKEQRNLGLL VHLMTSNPKI LYAPAGSEVD RVILKANETF  480
AFVGNVTHYA QVWLNISAEI RSFLEQGRLQ QHLRWLQQYV AELRLHPEAL NLSLDELPPA  540
LRQDNFSLPS GMALLQQLDT IDNAACGWIQ FMSKVSVDIF KGFPDEESIV NYTLNQAYQD  600
NVTVFASVIF QTRKDGSLPP HVHYKIRQNS SFTEKTNEIR RAYWRPGPNT GGRFYFLYGF  660
```

```
VWIQDMMERA IIDTFVGHDV VEPGSYVQMF PYPCYTRDDF LFVIEHMMPL CMVISWVYSV  720
AMTIQHIVAE KEHRLKEVMK TMGLNNAVHW VAWFITGFVQ LSISVTALTA ILKYGQVLMH  780
SHVVIIWLFL AVYAVATIMF CFLVSVLYSK AKLASACGGI IYFLSYVPYM YVAIREEVAH  840
DKITAFEKCI ASLMSTTAFG LGSKYFALYE VAGVGIQWHT FSQSPVEGDD FNLLLAVTML  900
MVDAVVYGIL TWYIEAVHPG MYGLPRPWYF PLQKSYWLGS GRTEAWEWSW PWARTPRLSV  960
MEEDQACAME SRRFEETRGM EEEPTHLPLV VCVDKLTKVY KDDKKLALNK LSLNLYENQV  1020
VSFLGHNGAG KTTTMSILTG LFPPTSGSAT IYGHDIRTEM DEIRKNLGMC PQHNVLFDRL  1080
TVEEHLWFYS RLKSMAQEEI RREMDKMIED LELSNKRHSL VQTLSGGMKR KLSVAIAFVG  1140
GSRAIILDEP TAGVDPYARR AIWDLILKYK PGRTILLSTH HMDEADLLGD RIAIISHGKL  1200
KCCGSPLFLK GTYGDGYRLT LVKRPAEPGG PQEPGLASSP PGRAPLSSCS ELQVSQFIRK  1260
HVASCLLVSD TSTELSYILP SEAAKKGAFE RLFQHLERSL DALHLSSFGL MDTTLEEVFL  1320
KVSEEDQSLE NSEADVKESR KDVLPGAEGP ASGEGHAGNL ARCSELTQSQ ASLQSASSVG  1380
SARGDEGAGY TDVYGDYRPL FDNPQDPDNV SLQEVEAEAL SRVGQGSRKL DGGWLKVRQF  1440
HGLLVKRFHC ARRNSKALFS QILLPAFFVC VAMTVALSVP EIGDLPPLVL SPSQYHNYTQ  1500
PRGNFIPYAN EERREYRLRL SPDASPQQLV STFRLPSGVG ATCVLKSPAN GSLGPTLNLS  1560
SGESRLLAAR FFDSMCLESF TQGLPLSNFV PPPPSPAPSD SPASPDEDLQ AWNVSLPPTA  1620
GPEMWTSAPS LPRLVREPVR CTCSAQGTGF SCPSSVGGHP PQMRVVTGDI LTDITGHNVS  1680
EYLLFTSDRF RLHRYGAITF GNVLKSIPAS FGTRAPPMVR KIAVRRAAQV FYNNKGYHSM  1740
PTYLNSLNNA ILRANLPKSK GNPAAYGITV TNHPMNKTSA SLSLDYLLQG TDVVIAIFII  1800
VAMSFVPASF VVFLVAEKST KAKHLQFVSG CNPIIYWLAN YVWDMLNYLV PATCCVIILF  1860
VFDLPAYTSP TNFPAVLSLF LLYGWSITPI MYPASFWFEV PSSAYVFLIV INLFIGITAT  1920
VATFLLQLFE HDKDLKVVNS YLKSCFLIFP NYNLGHGLME MAYNEYINEY YAKIGQFDKM  1980
KSPFEWDIVT RGLVAMAVEG VVGFLLTIMC QYNFLRRPQR MPVSTKPVED DVDVASERQR  2040
VLRGDADNDM VKIENLTKVY KSRKIGRILA VDRLCLGVRP GECFGLLGVN GAGKTSTFKM  2100
LTGDESTTGG EAFVNGHSVL KELLQVQQSL GYCPQCDALF DELTAREHLQ LYTRLRGISW  2160
KDEARVVKWA LEKLELTKYA DKPAGTYSGG NKRKLSTAIA LIGYPAFIFL DEPTTGMDPK  2220
ARRFLWNLIL DLIKTGRSVV LTSHSMEECE ALCTRLAIMV NGRLRCLGSI QHLKNRFGDG  2280
YMITVRTKSS QSVKDVVRFF NRNFPEAMLK ERHHTKVQYQ LKSEHISLAQ VFSKMEQVSG  2340
VLGIEDYSVS QTTLDNVFVN FAKKQSDNLE QQETEPPSAL QSPLGCLLSL LRPRSAPTEL  2400
RALVADEPED LDTEDEGLIS FEEERAQLSF NTDTLC                           2436

SEQ ID NO: 4           moltype = AA  length = 418
FEATURE                Location/Qualifiers
source                 1..418
                       mol_type = protein
                       organism = Homo sapiens
SEQUENCE: 4
MPSSVSWGIL LLAGLCCLVP VSLAEDPQGD AAQKTDTSHH DQDHPTFNKI TPNLAEFAFS  60
LYRQLAHQSN STNIFFSPVS IATAFAMLSL GTKADTHDEI LEGLNFNLTE IPEAQIHEGF  120
QELLRTLNQP DSQLQLTTGN GLFLSEGLKL VDKFLEDVKK LYHSEAFTVN FGDTEEAKKQ  180
INDYVEKGTQ GKIVDLVKEL DRDTVFALVN YIFFKGKWER PFEVKDTEEE DFHVDQVTTV  240
KVPMMKRLGM FNIQHCKKLS SWVLLMKYLG NATAIFFLPD EGKLQHLENE LTHDIITKFL  300
ENEDRRSASL HLPKLSITGT YDLKSVLGQL GITKVFSNGA DLSGVTEEAP LKLSKAVHKA  360
VLTIDEKGTE AAGAMFLEAI PMSIPPEVKF NKPFVFLMIE QNTKSPLFMG KVVNPTQK    418

SEQ ID NO: 5           moltype = AA  length = 823
FEATURE                Location/Qualifiers
source                 1..823
                       mol_type = protein
                       organism = Homo sapiens
SEQUENCE: 5
MKLFGFGSRR GQTAQGSIDH VYTGSGYRIR DSELQKIHRA AVKGDAAEVE RCLARRSGEL  60
DALDKQHRTA LHLACASGHV QVVTLLVNRK CQIDVCDKEN RTPLIQAVHC QEEACAVILL  120
EHGANPNLKD IYGNTALHYA VYSESTSLAE KLLSHGAHIE ALDKDNNTPL LFAIICKKEK  180
MVEFLLKKKA SSHAVDRLRR SALMLAVYYD SPGIVNILLK QNIDVFAQDM CGRDAEDYAI  240
SHHLTKIQQQ ILEHKKKILK KEKSDVGSSD ESAVSIFHEL RVDSLPASDD KDLNVATKQC  300
VPEKVSEPLP GSSHEKGNRI VNGQGEGPPA KHPSLKPSTE VEDPAVKGAV QRKNVQTLRA  360
EQALPVASEE EQQRHERSEK KQPQVKEGNN TNKSEKIQLS ENICDSTSSA AAGRLTQQRK  420
IGKTYPQQFP KKLKEEHDRC TLKQENEEKT NVNMLYKKNR EELERKEKQY KKEVEAKQLE  480
PTVQSLEMKS KTARNTPNWD FHNHEEMKGL MDENCILKAD IAILRQEICT MKNDNLEKEN  540
KYLKDIKIVK ETNAALEKYI KLNEEMITET AFRYQQELND LKAENTRLNA ELLKEKESKK  600
RLEADIESYQ SRLAAAISKH SESVKTERNL KLALERTQDV SVQVEMSSAI SKVKDENEFL  660
TEQLSETQIK FNALKDKFRK TRDSLRKKSL ALETVQNNLS QTQQQTQEMK EMYQNAEAKV  720
NNSTGKWNCV EERICHLQRE NAWLVQQLDD VHQKEDHKEI VTNIQRGFIE SGKKDFVLEE  780
KSKKLMNECD HLKESLFQYE REKTEVVVSI KEDKYFQTSR KKI                    823

SEQ ID NO: 6           moltype = AA  length = 357
FEATURE                Location/Qualifiers
source                 1..357
                       mol_type = protein
                       organism = Homo sapiens
SEQUENCE: 6
MGRQLAGCGD AGKKASFKMS TVHEILCKLS LEGDHSTPPS AYGSVKAYTN FDAERDALNI  60
ETAIKTKGVD EVTIVNILTN RSNAQRQDIA FAYQRRTKKE LASALKSALS GHLETVILGL  120
LKTPAQYDAS ELKASMKGLG TDEDSLIEII CSRTNQELQE INRVYKEMYK TDLEKDIISD  180
TSGDFRKLMV ALAKGRRAED GSVIDYELID QDARDLYDAG VKRKGTDVPK WISIMTERSV  240
PHLQKVFDRY KSYSPYDMLE SIRKEVKGDL ENAFLNLVQC IQNKPLYFAD RLYDSMKGKG  300
TRDKVLIRIM VSRSEVDMLK IRSEFKRKYG KSLYYYIQQD TKGDYQKALL YLCGGDD     357
```

```
SEQ ID NO: 7            moltype = AA  length = 1101
FEATURE                 Location/Qualifiers
source                  1..1101
                        mol_type = protein
                        organism = Homo sapiens
SEQUENCE: 7
MSAAPAYSED KGGSAGPGEP EYGHDPASGG IFSSDYKRHD DLKEMLDTNK DSLKLEAMKR  60
IVAMIARGKN ASDLFPAVVK NVACKNIEVK KLVYVYLVRY AEEQQDLALL SISTFQRGLK  120
DPNQLIRASA LRVLSSIRVP IIVPIMMLAI KEAASDMSPY VRKTAAHAIP KLYSLDSDQK  180
DQLIEVIEKL LADKTTLVAG SVVMAFEEVC PERIDLIHKN YRKLCNLLID VEEWGQVVII  240
SMLTRYARTQ FLSPTQNESL LEENAEKAFY GSEEDEAKGA GSEETAAAAA PSRKPYVMDP  300
DHRLLLRNTK PLLQSRSAAV VMAVAQLYFH LAPKAEVGVI AKALVRLLRS HSEVQYVVLQ  360
NVATMSIKRR GMFEPYLKSF YIRSTDPTQI KILKLEVLTN LANETNIPTV LREFQTYIRS  420
MDKDFVAATI QAIGRCATNI GRVRDTCLNG LVQLLSNRDE LVVAESVVVI KKLLQMQPAQ  480
HGEIIKHLAK LTDNIQVPMA RASILWLIGE YCEHVPRIAP DVLRKMAKSF TAEEDIVKLQ  540
VINLAAKLYL TNSKQTKLLT QYVLSLAKYD QNYDIRDRAR FTRQLIVPSE QGGALSRHAK  600
KLFLAPKPAP VLESSFKDRD HFQLGSLSHL LNAKATGYQE LPDWPEEAPD PSVRNVEEED  660
LSLIETHVGL LGEYTEVPEW TKCSNREKRK EKEKPFYSDS EGESGPTESA DSDPESESES  720
DSKSSSESGS GESSSESDNE DQDEDEEKGR GSESEQSEED GKRKTKKKVP ERKGEASSSD  780
EGSDSSSSSS ESEMTSESEE EQLEPASWSR KTPPSSKSAP ATKEISLLDL EDFTPPSVQP  840
VSPPAIVSTS LAADLEGLTL TDSTLVPSLL SPVSGVGRQE LLHRVAGEGL AVDYTFSRQP  900
FSGDPHMVSV HIHFSNSSDT PIKGLHVGTP KLPAGISIQE FPEIESLAPG ESATAVMGIN  960
FCDSTQAANF QLCTQTRQFY VSIQPPVGEL MAPVFMSENE FKKEQGKLMG MNEITEKLML  1020
PDTCRSDHIV VQKVTATANL GRVPCGTSDE YRFAGRTLTG GSLVLLTLDA RPAGAAQLTV  1080
NSEKMVIGTM LVKDVIQALT Q                                          1101

SEQ ID NO: 8            moltype = AA  length = 267
FEATURE                 Location/Qualifiers
source                  1..267
                        mol_type = protein
                        organism = Homo sapiens
SEQUENCE: 8
MKAAVLTLAV LFLTGSQARH FWQQDEPPQS PWDRVKDLAT VYVDVLKDSG RDYVSQFEGS  60
ALGKQLNLKL LDNWDSVTST FSKLREQLGP VTQEFWDNLE KETEGLRQEM SKDLEEVKAK  120
VQPYLDDFQK KWQEEMELYR QKVEPLRAEL QEGARQKLHE LQEKLSPLGE EMRDRARAHV  180
DALRTHLAPY SDELRQRLAA RLEALKENGG ARLAEYHAKA TEHLSTLSEK AKPALEDLRQ  240
GLLPVLESFK VSFLSALEEY TKKLNTQ                                    267

SEQ ID NO: 9            moltype = AA  length = 4563
FEATURE                 Location/Qualifiers
source                  1..4563
                        mol_type = protein
                        organism = Homo sapiens
SEQUENCE: 9
MDPPRPALLA LLALPALLLL LLAGARAEEE MLENVSLVCP KDATRFKHLR KYTYNYEAES  60
SSGVPGTADS RSATRINCKV ELEVPQLCSF ILKTSQCTLK EVYGFNPEGK ALLKKTKNSE  120
EFAAAMSRYE LKLAIPEGKQ VFLYPEKDEP TYILNIKRGI ISALLVPPET EEAKQVLFLD  180
TVYGNCSTHF TVKTRKGNVA TEISTERDLG QCDRFKPIRT GISPLALIKG MTRPLSTLIS  240
SSQSCQYTLD AKRKHVAEAI CKEQHLFLPF SYKNKYGMVA QVTQTLKLED TPKINSRFFG  300
EGTKKMGLAF ESTKSTSPPK QAEAVLKTLQ ELKKLTISEQ NIQRANLFNK LVTELRGLSD  360
EAVTSLLPQL IEVSSPITLQ ALVQCGQPQC STHILQWLKR VHANPLLIDV VTYLVALIPE  420
PSAQQLREIF NMARDQRSRA TLYALSHAVN NYHKTNPTGT QELLDIANYL MEQIQDDCTG  480
DEDYTYLILR VIGNMGQTME QLTPELKSSI LKCVQSTKPS LMIQKAAIQA LRKMEPKDKD  540
QEVLLQTFLD DASPGDKRLA AYLMLMRSPS QADINKIVQI LPWEQNEQVK NFVASHIANI  600
LNSEELDIQD LKKLVKEALK ESQLPTVMDF RKFSRNYQLY KSVSLPSLDP ASAKIEGNLI  660
FDPNNYLPKE SMLKTTLTAF GFASADLIEI GLEGKGFEPT LEALFGKQGF FPDSVNKALY  720
WVNGQVPDGV SKVLVDHFGY TKDDKHEQDM VNGIMLSVEK LIKDLKSKEV PEARAYLRIL  780
GEELGFASLH DLQLLGKLLL MGARTLQGIP QMIGEVIRKG SKNDFFLHYI FMENAFELPT  840
GAGLQLQISS SGVIAPGAKA GVKLEVANMQ AELVAKPSVS VEFVTNMGII IPDFARSGVQ  900
MNTNFFHESG LEAHVALKAG KLKFIIPSPK RPVKLLSGGN TLHLVSTTKT EVIPPLIENR  960
QSWSVCKQVF PGLNYCTSGA YSNASSTDSA SYYPLTGDTR LELELRPTGE IEQYSVSATY  1020
ELQREDRALV DTLKFVTQAE GAKQTEATMT FKYNRQSMTL SSEVQIPDFD VDLGTILRVN  1080
DESTEGKTSY RLTLDIQNKK ITEVALMGHL SCDTKEERKI KGVISIPRLQ AEARSEILAH  1140
WSPAKLLLQM DSSATAYGST VSKRVAWHYD EEKIEFEWNT GTNVDTKKMT SNFPVDLSDY  1200
PKSLHMYANR LLDHRVPQTD MTFRHVGSKL IVAMSSWLQK ASGSLPYTQT LQDHLNSLKE  1260
FNLQNMGLPD FHIPENLFLK SDGRVKYTLN KNSLKIEIPL PFGGKSSRDL KMLETVRTPA  1320
LHFKSVGFHL PSREFQVPTF TIPKLYQLQV PLLGVLDLST NVYSNLYNWS ASYSGGNTST  1380
DHFSLRARYH MKADSVVDLL SYNVQGSGET TYDHKNTFTL SCDGSLRHKF LDSNIKFSHV  1440
EKLGNNPVSK GLLIFDASSS WGPQMSASVH LDSKKKQHLF VKEVKIDGQF RVSSFYAKGT  1500
YGLSCQRDPN TGRLNGESNL RFNSSYLQGT NQITGRYEDG TLSLTSTSDL QSGIIKNTAS  1560
LKYENYELTL KSDTNGKYKN FATSNKMDMT FSKQNALLRS EYQADYESLR FFSLLSGSLN  1620
SHGLELNADI LGTDKINSGA HKATLRIGQD GISTSATTNL KCSLLVLENE LNAELGLSGA  1680
SMKLTTNGRF REHNAKFSLD GKAALTELSL GSAYQAMILG VDSKNIFNFK VSQEGLKLSN  1740
DMMGSYAEMK FDHTNSLNIA GLSLDFSSKL DNIYSSDKFY KQTVNLQLQP YSLVTTLNSD  1800
LKYNALDLTN NGKLRLEPLK LHVAGNLKGA YQNNEIKHIY AISSAALSAS YKADTVAKVQ  1860
GVEFSHRLNT DIAGLASAID MSTNYNSDSL HFSNVFRSVM APFTMTIDAH TNGNGKLALW  1920
GEHTGQLYSK FLLKAEPLAF TFSHDYKGST SHHLVSRKSI SAALEHKVSA LLTPAEQTGT  1980
WKLKTQFNNN EYSQDLDAYN TKDKIGVELT GRTLADLTLL DSPIKVPLLL SEPINIIDAL  2040
EMRDAVEKPQ EFTIVAFVKY DKNQDVHSIN LPFFETLQEY FERNRQTIIV VLENVQRNLK  2100
```

```
HINIDQFVRK YRAALGKLPQ QANDYLNSFN WERQVSHAKE KLTALTKKYR ITENDIQIAL  2160
DDAKINFNEK LSQLQTYMIQ FDQYIKDSYD LHDLKIAIAN IIDEIIEKLK SLDEHYHIRV  2220
NLVKTIHDLH LFIENIDFNK SGSSTASWIQ NVDTKYQIRI QIQEKLQQLK RHIQNIDIQH  2280
LAGKLKQHIE AIDVRVLLDQ LGTTISFERI NDVLEHVKHF VINLIGDFEV AEKINAFRAK  2340
VHELIERYEV DQQIQVLMDK LVELAHQYKL KETIQKLSNV LQQVKIKDYF EKLVGFIDDA  2400
VKKLNELSFK TFIEDVNKFL DMLIKKLKSF DYHQFVDETN DKIREVTQRL NGEIQALELP  2460
QKAEALKLFL EETKATVAVY LESLQDTKIT LIINWLQEAL SSASLAHMKA KFRETLEDTR  2520
DRMYQMDIQQ ELQRYLSLVG QVYSTLVTYI SDWWTLAAKN LTDFAEQYSI QDWAKRMKAL  2580
VEQGFTVPEI KTILGTMPAF EVSLQALQKA TFQTPDFIVP LTDLRIPSVQ INFKDLKNIK  2640
IPSRFSTPEF TILNTFHIPS FTIDFVEMKV KIIRTIDQML NSELQWPVPD IYLRDLKVED  2700
IPLARITLPD FRLPEIAIPE FIIPTLNLND FQVPDLHIPE FQLPHISHTI EVPTFGKLYS  2760
ILKIQSPLFT LDANADIGNG TTSANEAGIA ASITAKGESK LEVLNFDFQA NAQLSNPKIN  2820
PLALKESVKF SSKYLRTEHG SEMLFFGNAI EGKSNTVASL HTEKNTLELS NGVIVKINNQ  2880
LTLDSNTKYF HKLNIPKLDF SSQADLRNEI KTLLKAGHIA WTSSGKGSWK WACPRFSDEG  2940
THESQISFTI EGPLTSFGLS NKINSKHLRV NQNLVYESGS LNFSKLEIQS QVDSQHVGHS  3000
VLTAKGMALF GEGKAEFTGR HDAHLNGKVI GTLKNSLFFS AQPFEITAST NNEGNLKVRF  3060
PLRLTGKIDF LNNYALFLSP SAQQASWQVS ARFNQYKYNQ NFSAGNNENI MEAHVGINGE  3120
ANLDFLNIPL TIPEMRLPYT IITTPPLKDF SLWEKTGLKE FLKTTKQSFD LSVKAQYKKN  3180
KHRHSITNPL AVLCEFISQS IKSFDRHFEK NRNNALDFVT KSYNETKIKF DKYKAEKSHD  3240
ELPRTFQIPG YTVPVVNVEV SPFTIEMSAF GYVFPKAVSM PSFSILGSDV RVPSYTLILP  3300
SLELPVLHVP RNLKLSLPDF KELCTISHIF IPAMGNITYD FSFKSSVITL NTNAELFNQS  3360
DIVAHLLSSS SSVIDALQYK LEGTTRLTRK RGLKLATALS LSNKFVEGSH NSTVSLTTKN  3420
MEVSVATTTK AQIPILRMNF KQELNGNTKS KPTVSSSMEF KYDFNSSMLY STAKGAVDHK  3480
LSLESLTSYF SIESSTKGDV KGSVLSREYS GTIASEANTY LNSKSTRSSV KLQGTSKIDD  3540
IWNLEVKENF AGEATLQRIY SLWEHSTKNH LQLEGLFFTN GEHTSKATLE LSPWQMSALV  3600
QVHASQPSSF HDFPDLGQEV ALNANTKNQK IRWKNEVRIH SGSFQSQVEL SNDQEKAHLD  3660
IAGSLEGHLR FLKNIILPVY DKSLWDFLKL DVTTSIGRRQ HLRVSTAFVY TKNPNGYSFS  3720
IPVKVLADKF IIPGLKLNDL NSVLVMPTFH VPFTDLQVPS CKLDFREIQI YKKLRTSSFA  3780
LNLPTLPEVK FPEVDVLTKY SQPEDSLIPF FEITVPESQL TVSQFTLPKS VSDGIAALDL  3840
NAVANKIADF ELPTIIVPEQ TIEIPSIKFS VPAGIVIPSF QALTARFEVD SPVYNATWSA  3900
SLKNKADYVE TVLDSTCSST VQFLEYELNV LGTHKIEDGT LASKTKGTFA HRDFSAEYEE  3960
DGKYEGLQEW EGKAHLNIKS PAFTDLHLRY QKDKKGISTS AASPAVGTVG MDMDEDDDFS  4020
KWNFYYSPQS SPDKKLTIFK TELRVRESDE ETQIKVNWEE EAASGLLTSL KDNVPKATGV  4080
LYDYVNKYHW EHTGLTLREV SSKLRRNLQN NAEWVYQGAI RQIDDIDVRF QKAASGTTGT  4140
YQEWKDKAQN LYQELLTQEG QASFQGLKDN VFDGLVRVTQ EFHMKVKHLI DSLIDFLNFP  4200
RFQFPGKPGI YTREELCTMF IREVGTVLSQ VYSKVHNGSE ILFSYFQDLV ITLPFELRKH  4260
KLIDVISMYR ELLKDLSKEA QEVFKAIQSL KTTEVLRNLQ DLLQFIFQLI EDNIKQLKEM  4320
KFTYLINYIQ DEINTIFSDY IPYVFKLLKE NLCLNLHKFN EFIQNELQEA SQELQQIHQY  4380
IMALREEYFD PSIVGWTVKY YELEEKIVSL IKNLLVALKD FHSEYIVSAS NFTSQLSSQV  4440
EQFLHRNIQE YLSILTDPDG KGKEKIAELS ATAQEIIKSQ AIATKKIISD YHQQFRYKLQ  4500
DFSDQLSDYY EKFIAESKRL IDLSIQNYHT FLIYITELLK KLQSTTVMNP YMKLAPGELT  4560
IIL                                                              4563

SEQ ID NO: 10          moltype = AA  length = 343
FEATURE                Location/Qualifiers
source                 1..343
                       mol_type = protein
                       organism = Homo sapiens
SEQUENCE: 10
MSSGASRKSW DPGNPWPPDW PITGRKMKVL WAALLVTFLA GCQAKVEQAV ETEPEPELRQ  60
QTEWQSGQRW ELALGRFWDY LRWVQTLSEQ VQEELLSSQV TQELRALMDE TMKELKAYKS  120
ELEEQLTPVA EETRARLSKE LQAAQARLGA DMEDVCGRLV QYRGEVQAML GQSTEELRVR  180
LASHLRKLRK RLLRDADDLQ KRLAVYQAGA REGAERGLSA IRERLGPLVE QGRVRAATVG  240
SLAGQPLQER AQAWGERLRA RMEEMGSRTR DRLDEVKEQV AEVRAKLEEQ AQQIRLQAEA  300
FQARLKSWFE PLVEDMQRQW AGLVEKVQAA VGTSAAPVPS DNH                   343

SEQ ID NO: 11          moltype = AA  length = 237
FEATURE                Location/Qualifiers
source                 1..237
                       mol_type = protein
                       organism = Homo sapiens
SEQUENCE: 11
MSAKSRTIGI IGAPFSKGQP RGGVEEGPTV LRKAGLLEKL KEQECDVKDY GDLPFADIPN  60
DSPFQIVKNP RSVGKASEQL AGKVAEVKKN GRISLVLGGD HSYILKTLGI KYFSMTEVDR  120
LGIGKVMEET LSYLLGRKKR PIHLSFDVDG LDPSFTPATG TPVVGGLTYR EGLYITEEIY  180
KTGLLSGLDI MEVNPSLGKT PEEVTRTVNT AVAITLACFG LAREGNHKPI DYLNPPK     237

SEQ ID NO: 12          moltype = AA  length = 1288
FEATURE                Location/Qualifiers
source                 1..1288
                       mol_type = protein
                       organism = Homo sapiens
SEQUENCE: 12
MAAAGARLSP GPGSGLRGRP RLCFHPGPPP LLPLLLLFLL LLPPPPLLAG ATAAASREPD  60
SPCRLKTVTV STLPALRESD IGWSGARAGA GAGTGAGAAA AAASPGSPGS AGTAAESRLL  120
LFVRNELPGR IAVQDDLDNT ELPFFTLEMS GTAADISLVH WRQQWLENGT LYFHVSMSSS  180
GQLAQATAPT LQEPSEIVEE QMHILHISVM GGLIALLLLL LVFTVALYAQ RRWQKRRRIP  240
QKSASTEATH EIHYIPSVLL GPQARESFRS SRLQTHNSVI GVPIRETPIL DDYDCEEDEE  300
PPRRANHVSR EDEFGSQVTH TLDSLGHPGE EKVDFEKKGG ISFGRAKGTS GSEADDETQL  360
```

```
TFYTEQYRSR RRSKGLLKSP VNKTALTLIA VSSCILAMVC GSQMSCPLTV KVTLHVPEHF  420
IADGSSFVVS EGSYLDISDW LNPAKLSLYY QINATSPWVR DLCGQRTTDA CEQLCDPETG  480
ECSCHEGYAP DPVHRHLCVR SDWGQSEGPW PYTTLERGYD LVTGEQAPEK ILRSTFSLGQ  540
GLWLPVSKSF VVPPVELSIN PLASCKTDVL VTEDPADVRE EAMLSTYFET INDLLSSFGP  600
VRDCSRNNGG CTRNFKCVSD RQVDSSGCVC PEELKPMKDG SGCYDHSKGI DCSDGFNGGC  660
EQLCLQQTLP LPYDATSSTI FMFCGCVEEY KLAPDGKSCL MLSDVCEGPK CLKPDSKFND  720
TLFGEMLHGY NNRTQHVNQG QVFQMTFREN NFIKDFPQLA DGLLVIPLPV EEQCRGVLSE  780
PLPDLQLLTG DIRYDEAMGY PMVQQWRVRS NLYRVKLSTI TLAAGFTNVL KILTKESSRE  840
ELLSFIQHYG SHYIAEALYG SELTCIIHFP SKKVQQQLWL QYQKETTELG SKKELKSMPF  900
ITYLSGLLTA QMLSDDQLIS GVEIRCEEKG RCPSTCHLCR RPGKEQLSPT PVLLEINRVV  960
PLYTLIQDNG TKEAFKSALM SSYWCSGKGD VIDDWCRCDL SAFDANGLPN CSPLLQPVLR  1020
LSPTVEPSST VVSLEWVDVQ PAIGTKVSDY ILQHKKVDEY TDTDLYTGEF LSFADDLLSG  1080
LGTSCVAAGR SHGEVPEVSI YSVIFKCLEP DGLYKFTLYA VDTRGRHSEL STVTLRTACP  1140
LVDDNKAEEI ADKIYNLYNG YTSGKEQQMA YNTLMEVSAS MLFRVQHHYN SHYEKFGDFV  1200
WRSEDELGPR KAHLILRRLE RVSSHCSSLL RSAYIQSRVE TVPYLFCRSE EVRPAGMVWY  1260
SILKDTKITC EEKMVSMARN TYGESKGR                                    1288

SEQ ID NO: 13          moltype = AA  length = 476
FEATURE                Location/Qualifiers
source                 1..476
                       mol_type = protein
                       organism = Homo sapiens
SEQUENCE: 13
MGSKMNLIEH SHLPTTDEFS FSENLFGVLT EQVAGPLGQN LEVEPYSQYS NVQFPQVQPQ  60
ISSSSYYSNL GFYPQQPEEW YSPGIYELRR MPAETLYQGE TEVAEMPVTK KPRMGASAGR  120
IKGDELCVVC GDRASGYHYN ALTCEGCKGF FRRSITKNAV YKCKNGGNCV MDMYMRRKCQ  180
ECRLRKCKEM GMLAECMYTG LLTEIQCKSK RLRKNVKQHA DQTVNEDSEG RDLRQVTSTT  240
KSCREKTELT PDQQTLLHFI MDSYNKQRMP QEITNKILKE EFSAEENFLI LTEMATNHVQ  300
VLVEFTKKLP GFQTLDHEDQ IALLKGSAVE AMFLRSAEIF NKKLPSGHSD LLEERIRNSG  360
ISDEYITPMF SFYKSIGELK MTQEEYALLT AIVILSPDRQ YIKDREAVEK LQEPLLDVLQ  420
KLCKIHQPEN PQHFACLLGR LTELRTFNHH HAEMLMSWRV NDHKFTPLLC EIWDVQ      476

SEQ ID NO: 14          moltype = AA  length = 3051
FEATURE                Location/Qualifiers
source                 1..3051
                       mol_type = protein
                       organism = Homo sapiens
SEQUENCE: 14
MATNPQPQPP PPAPPPPPPQ PQPQPPPPPP GPGAGPGAGG AGGAGAGAGD PQLVAMIVNH  60
LKSQGLFDQF RRDCLADVDT KPAYQNLRQR VDNFVANHLA THTWSPHLNK NQLRNNIRQQ  120
VLKSGMLESG IDRIISQVVD PKINHTFRPQ VEKAVHEFLA TLNHKEEGSG NTAPDDEKPD  180
TSLITQGVPT PGPSANVAND AMSILETITS LNQEASAARA STETSNAKTS ERASKKLPSQ  240
PTTDTSTDKE RTSEDMADKE KSTADSGGEG LETAPKSEEF SDLPCPVEEI KNYTKEHNNL  300
ILLNKDVQQE SSEQKNKSTD KGEKKPDSNE KGERKKEKKE KTEKKFDHSK KSEDTQKVKD  360
EKQAKEKEVE SLKLPSEKNS NKAKTVEGTK EDFSLIDSDV DGLTDITVSS VHTSDLSSFE  420
EDTEEEVVTS DSMEEGEITS DDEEKNKQNK TKTQTSDSSE GKTKSVRHAY VHKPYLYSKY  480
YSDSDDELTV EQRRQSIAKE KEERLLRRQI NREKLEEKRK QKAEKTKSSK TKGQGRSSVD  540
LEESSTKSLE PKAARIKEVL KERKVLEKKV ALSKKRKKDS RNVEENSKKK QQYEEDSKET  600
LKTSEHCEKE KISSSKELKH VHAKSEPSKP ARRLSESLHV VDENKNESKL EREHKRRTST  660
PVIMEGVQEE TDTRDVKRQV ERSEICTEEP QKQKSTLKNE KHLKKDDSET PHLKSLLKKE  720
VKSSKEKPER EKTPSEDKLS VKHKYKGDCM HKTGDETELH SSEKGLKVEE NIQKQSQQTK  780
LSSDDKTERK SKHRNERKLS VLGKDGKPVS EYIIKTDENV RKENNKKERR LSAEKTKAEH  840
KSRRSSDSKI QKDSLGSKQH GITLQRRSES YSEDKCDMDS TNMDSNLKPE EVVHKEKRRT  900
KSLLEEKLVL KSKSKTQGKQ VKVVETELQE GATKQATTPK PDKEKNTEEN DSEKQRKSKV  960
EDKPFEETGV EPVLETASSS AHSTQKDSSH RAKLPLAKEK YKSDKDSTST RLERKLSDGH  1020
KSRSLKHSSK DIKKKDENKS DDKDGKEVDS SHEKARGNSS LMEKKLSRRL CENRRGSLSQ  1080
EMAKGEEKLA ANTLSTPSGS SLQRPKKSGD MTLIPEQEPM EIDSEPGVEN VFEVSKTQDN  1140
RNNNSQQDID SENMKQKTSA TVQKDELRTC TADSKATAPA YKPGRGTGVN SNSEKHADHR  1200
STLTKKMHIQ SAVSKMNPGE KEPIHRGTTE VNIDSETVHR MLLSAPSEND RVQKNLKNTA  1260
AEEHVAQGDA TLEHSTNLDS SPSLSSVTVV PLRESYDPDV IPLFDKRTVL EGSTASTSPA  1320
DHSALPNQSL TVRESEVLKT SDSKEGGEGF TVDTPAKASI TSKRHIPEAH QATLLDGKQG  1380
KVIMPLGSKL TGVIVENENI TKEGGLVDMA KKENDLNAEP NLKQTIKATV ENGKKDGIAV  1440
DHVVGLNTEK YAETVKLKHK RSPGKVKDIS IDVERRNENS EVDTSAGSGS APSVLHQRNG  1500
QTEDVATGPR RAEKTSVATS TEGKDKDVTL SPVKAGPATT TSSETRQSEV ALPCTSIEAD  1560
EGLIIGTHSR NNPLHVGAEA SECTVFAAAE EGGAVVTEGF AESETFLTST KEGESGECAV  1620
AESEDRAADL LAVHAVKIEA NVNSVVTEEK DDAVTSAGSE EKCDGSLSRD SEIVEGTITF  1680
ISEVESDGAV TSAGTEIRAG SISSEEVDGS QGNMMRMGPK KETEGTVTCT GAEGRSDNFV  1740
ICSVTGAGPR EERMVTGAGV VLGDNDAPPG TSASQEGDGS VNDGTEGESA VTSTGITEDG  1800
EGPASCTGSE DSSEGFAISS ESEENGESAM DSTVAKEGTN VPLVAAGPCD DEGIVTSTGA  1860
KEEDEEGEDV VTSTGRGNEI GHASTCTGLG EESEGVLICE SAEGDSQIGT VVEHVEAEAG  1920
AAIMNANENN VDSMSGTEKG SKDTDICSSA KGIVESSVTS AVSGKDEVTP VPGGCEGPMT  1980
SAASDQSDSQ LEKVEDTTIS TGLVGGSYDV LVSGEVPECE VAHTSPSEKE DEDIITSVEN  2040
EECDGLMATT ASGDITNQNS LAGGKNQGKV LIISTSTTND YTPQVSAITD VEGGLSDALR  2100
TEENMEGTRV TTEEFEAPMP SAVSGDDSQL TASRSEEKDE CAMISTSIGE EFELPISSAT  2160
TIKCAESLQP VAAAVEERAT GPVLISTADF EGPMPSAPPE AESPLASTSK EEKDECALIS  2220
TSIAEECEAS VSGVVVESEN ERAGTVMEEK DGSGIISTSS VEDCEGPVSS AVPQEEGDPS  2280
VTPAEEMGDT AMISTSTSEG CEAVMIGAVL QDEDRLTITR VEDLSDAAII STSTAECMPI  2340
SASIDRHEEN QLTADNPEGN GDLSATEVSK HKVPMPSLIA ENNCRCPGPV RGGKEPGPVL  2400
AVSTEEGHNG PSVHKPSAGQ GHPSAVCAEK EEKHGKECPE IGPFAGRGQK ESTLHLINAE  2460
```

```
EKNVLLNSLQ KEDKSPETGT AGGSSTASYS AGRGLEGNAN SPAHLRGPEQ TSGQTAKDPS  2520
VSIRYLAAVN TGAIKADDMP PVQGTVAEHS FLPAEQQGSE DNLKTSTTKC ITGQESKIAP  2580
SHTMIPPATY SVALLAPKCE QDLTIKNDYS GKWTDQASAE KTGDDNSTRK SFPEEGDIMV  2640
TVSSEENVCD IGNEESPLNV LGGLKLKANL KMEAYVPSEE EKNGEILAPP ESLCGGKPSG  2700
IAELQREPLL VNESLNVENS GFRTNEEIHS ESYNKGEISS GRKDNAEAIS GHSVEADPKE  2760
VEEEERHMPK RKRKQHYLSS EDEPDDNPDV LDSRIETAQR QCPETEPHDT KEENSRDLEE  2820
LPKTSSETNS TTSRVMEEKD EYSSSETTGE KPEQNDDDTI KSQEEDQPII IKRKRGRPRK  2880
YPVETTLKMK DDSKTDTGIV TVEQSPSSSK LKVMQTDESN KETANLQERS ISNDDGEEKI  2940
VTSVRRRGRK PKRSLTVSDD AESSEPERKR QKSVSDPVED KKEQESDEEE EEEEEDEPSG  3000
ATTRSTTRSE AQRSKTQLSP SIKRKREVSP PGARTRGQQR VEEAPVKKAK R           3051

SEQ ID NO: 15           moltype = AA  length = 1208
FEATURE                 Location/Qualifiers
source                  1..1208
                        mol_type = protein
                        organism = Homo sapiens
SEQUENCE: 15
MANGGGGGGG SSGGGGGGGG SSLRMSSNIH ANHLSLDASS SSSSSSSSS SSSSSSSSS  60
VHEPKMDALI IPVTMEVPCD SRGQRMWWAF LASSMVTFFG GLFIILLWRT LKYLWTVCCH  120
CGGKTKEAQK INNGSSQADG TLKPVDEKEE AVAAEVGWMT SVKDWAGVMI SAQTLTGRVL  180
VVLVFALSIG ALVIYFIDSS NPIESCQNFY KDFTLQIDMA FNVFFLLYFG LRFIAANDKL  240
WFWLEVNSVV DFFTVPPVFV SVYLNRSWLG LRFLRALRLI QFSEILQFLN ILKTSNSIKL  300
VNLLSIFIST WLTAAGFIHL VENSGDPWEN FQNNQALTYW ECVYLLMVTM STVGYGDVYA  360
KTTLGRLFMV FFILGGLAMF ASYVPEIIEL IGNRKKYGGS YSAVSGRKHI VVCGHITLES  420
VSNFLKDFLH KDRDDVNVEI VFLHNISPNL ELEALFKRHF TQVEFYQGSV LNPHDLARVK  480
IESADACLIL ANKYCADPDA EDASNIMRVI SIKNYHPKIR IITQMLQYHN KAHLLNIPSW  540
NWKEGDDAIC LAELKLGFIA QSCLAQGLST MLANLFSMRS FIKIEEDTWQ KYYLEGVSNE  600
MYTEYLSSAF VGLSFPTVCE LCFVKLKLLM IAIEYKSANR ESRILINPGN HLKIQEGTLG  660
FFIASDAKEV KRAFFYCKAC HDDITDPKRI KKCGCKRLIY FEDEQPSTLS PKKKQRNGGM  720
RNSPNTSPKL MRHDPLLIPG NDQIDNMDSN VKKYDSTGMF HWCAPKEIEK VILTRSEAAM  780
TVLSGHVVVC IFGDVSSALI GLRNLVMPLR ASNFHYHELK HIVFVGSIEY LKREWETLHN  840
FPKVSILPGT PLSRADLRAV NINLCDMCVI LSANQNNIDD TSLQDKECIL ASLNIKSMQF  900
DDSIGVLQAN SQGFTPPGMD RSSPDNSPVH GMLRQPSITT GVNIPIITEL AKPGKLPLVS  960
VNQEKNSGTH ILMITELVND TNVQFLDQDD DDDPDTELYL TQPFACGTAF AVSVLDSLMS  1020
ATYFNDNILT LIRTLVTGGA TPELEALIAE ENALRGGYST PQTLANRDRC RVAQLALLDG  1080
PFADLGDGGC YGDLFCKALK TYNMLCFGIY RLRDAHLSTP SQCTKRYVIT NPPYEFELVP  1140
TDLIFCLMQF DHNAGQSRAS LSHSSHSSQS SSKKSSSVHS IPSTANRQNR PKSRESRDKQ  1200
KYVQEERL                                                          1208

SEQ ID NO: 16           moltype = AA  length = 149
FEATURE                 Location/Qualifiers
source                  1..149
                        mol_type = protein
                        organism = Homo sapiens
SEQUENCE: 16
MADQLTEEQI AEFKEAFSLF DKDGDGTITT KELGTVMRSL GQNPTEAELQ DMINEVDADG  60
NGTIDFPEFL TMMARKMKDT DSEEEIREAF RVFDKDGNGY ISAAELRHVM TNLGEKLTDE  120
EVDEMIREAD IDGDGQVNYE EFVQMMTAK                                   149

SEQ ID NO: 17           moltype = AA  length = 149
FEATURE                 Location/Qualifiers
source                  1..149
                        mol_type = protein
                        organism = Homo sapiens
SEQUENCE: 17
MADQLTEEQV TEFKEAFSLF DKDGDGCITT RELGTVMRSL GQNPTEAELR DMMSEIDRDG  60
NGTVDFPEFL GMMARKMKDT DNEEEIREAF RVFDKDGNGF VSAAELRHVM TRLGEKLSDE  120
EVDEMIRAAD TDGDGQVNYE EFVRVLVSK                                   149

SEQ ID NO: 18           moltype = AA  length = 146
FEATURE                 Location/Qualifiers
source                  1..146
                        mol_type = protein
                        organism = Homo sapiens
SEQUENCE: 18
MAGELTPEEE AQYKKAFSAV DTDGNGTINA QELGAALKAT GKNLSEAQLR KLISEVDSDG  60
DGEISFQEFL TAAKKARAGL EDLQVAFRAF DQDGDGHITV DELRRAMAGL GQPLPQEELD  120
AMIREADVDQ DGRVNYEEFA RMLAQE                                      146

SEQ ID NO: 19           moltype = AA  length = 261
FEATURE                 Location/Qualifiers
source                  1..261
                        mol_type = protein
                        organism = Homo sapiens
SEQUENCE: 19
MASPDWGYDD KNGPEQWSKL YPIANGNNQS PVDIKTSETK HDTSLKPISV SYNPATAKEI  60
INVGHSFHVN FEDNDNRSVL KGGPFSDSYR LFQFHFHWGS TNEHGSEHTV DGVKYSAELH  120
VAHWNSAKYS SLAEAASKAD GLAVIGVLMK VGEANPKLQK VLDALQAIKT KGKRAPFTNF  180
DPSTLLPSSL DFWTYPGSLT HPPLYESVTW IICKESISVS SEQLAQFRSL LSNVEGDNAV  240
```

```
PMQHNNRPTQ PLKGRTVRAS F                                           261

SEQ ID NO: 20          moltype = AA  length = 242
FEATURE                Location/Qualifiers
source                 1..242
                       mol_type = protein
                       organism = Homo sapiens
SEQUENCE: 20
MSNPRSLEEE KYDMSGARLA LILCVTKARE GSEEDLDALE HMFRQLRFES TMKRDPTAEQ  60
FQEELEKFQQ AIDSREDPVS CAFVVLMAHG REGFLKGEDG EMVKLENLFE ALNNKNCQAL  120
RAKPKVYIIQ ACRGEQRDPG ETVGGDEIVM VIKDSPQTIP TYTDALHVYS TVEGYIAYRH  180
DQKGSCFIQT LVDVFTKRKG HILELLTEVT RRMAEAELVQ EGKARKTNPE IQSTLRKRLY  240
LQ                                                                242

SEQ ID NO: 21          moltype = AA  length = 906
FEATURE                Location/Qualifiers
source                 1..906
                       mol_type = protein
                       organism = Homo sapiens
SEQUENCE: 21
MTAVHAGNIN FKWDPKSLEI RTLAVERLLE PLVTQVTTLV NTNSKGPSNK KRGRSKKAHV  60
LAASVEQATE NFLEKGDKIA KESQFLKEEL VAAVEDVRKQ GDLMKAAAGE FADDPCSSVK  120
RGNMVRAARA LLSAVTRLLI LADMADVYKL LVQLKVVEDG ILKLRNAGNE QDLGIQYKAL  180
KPEVDKLNIM AAKRQQELKD VGHRDQMAAA RGILQKNVPI LYTASQACLQ HPDVAAYKAN  240
RDLIYKQLQQ AVTGISNAAQ ATASDDASQH QGGGGGELAY ALNNFDKQII VDPLSFSEER  300
FRPSLEERLE SIISGAALMA DSSCTRDDRR ERIVAECNAV RQALQDLLSE YMGNAGRKER  360
SDALNSAIDK MTKKTRDLRR QLRKAVMDHV SDSFLETNVP LLVLIEAAKN GNEKEVKEYA  420
QVFREHANKL IEVANLACSI SNNEEGVKLV RMSASQLEAL CPQVINAALA LAAKPQSKLA  480
QENMDLFKEQ WEKQVRVLTD AVDDITSIDD FLAVSENHIL EDVNKCVIAL QEKDVDGLDR  540
TAGAIRGRAA RVIHVVTSEM DNYEPGVYTE KVLEATKLLS NTVMPRFTEQ VEAAVEALSS  600
DPAQPMDENE FIDASRLVYD GIRDIRKAVL MIRTPEELDD SDFETEDFDV RSRTSVQTED  660
DQLIAGQSAR AIMAQLPQEQ KAKIAEQVAS FQEEKSKLDA EVSKWDDSGN DIIVLAKQMC  720
MIMMEMTDFT RGKGPLKNTS DVISAAKKIA EAGSRMDKLG RTIADHCPDS ACKQDLLAYL  780
QRIALYCHQL NICSKVKAEV QNLGGELVVS GVDSAMSLIQ AAKNLMNAVV QTVKASYVAS  840
TKYQKSQGMA SLNLPAVSWK MKAPEKKPLV KREKQDETQT KIKRASQKKH VNPVQALSEF  900
KAMDSI                                                            906

SEQ ID NO: 22          moltype = AA  length = 412
FEATURE                Location/Qualifiers
source                 1..412
                       mol_type = protein
                       organism = Homo sapiens
SEQUENCE: 22
MQPSSLLPLA LCLLAAPASA LVRIPLHKFT SIRRTMSEVG GSVEDLIAKG PVSKYSQAVP  60
AVTEGPIPEV LKNYMDAQYY GEIGIGTPPQ CFTVVFDTGS SNLWVPSIHC KLLDIACWIH  120
HKYNSDKSST YVKNGTSFDI HYGSGSLSGY LSQDTVSVPC QSASSASALG GVKVERQVFG  180
EATKQPGITF IAAKFDGILG MAYPRISVNN VLPVFDNLMQ QKLVDQNIFS FYLSRDPDAQ  240
PGGELMLGGT DSKYYKGSLS YLNVTRKAYW QVHLDQVEVA SGLTLCKEGC EAIVDTGTSL  300
MVGPVDEVRE LQKAIGAVPL IQGEYMIPCE KVSTLPAITL KLGGKGYKLS PEDYTLKVSQ  360
AGKTLCLSGF MGMDIPPPSG PLWILGDVFI GRYYTVFDRD NNRVGFAEAA RL         412

SEQ ID NO: 23          moltype = AA  length = 3014
FEATURE                Location/Qualifiers
source                 1..3014
                       mol_type = protein
                       organism = Homo sapiens
SEQUENCE: 23
MAPPPPPVLP VLLLLAAAAA LPAMGLRAAA WEPRVPGGTR AFALRPGCTY AVGAACTPRA  60
PRELLDVGRD GRLAGRRRVS GAGRPLPLQV RLVARSAPTA LSRRLRARTH LPGCGARARL  120
CGTGARLCGA LCFPVPGGCA AAQHSALAAP TTLPACRCPP RPRPRCPGRP ICLPPGGSVR  180
LRLLCALRRA AGAVRVGLAL EAATAGTPSA SPSPSPPLPP NLPEARAGPA RRARRGTSGR  240
GSLKFPMPNY QVALFENEPA GTLILQLHAH YTIEGEEERV SYYMEGLFDE RSRGYFRIDS  300
ATGAVSTDSV LDRETKETHV LRVKAVDYST PPRSATTYIT VLVKDTNDHS PVFEQSEYRE  360
RVRENLEVGY EVLTIRASDR DSPINANLRY RVLGGAWDVF QLNESSGVVS TRAVLDREEA  420
AEYQLLVEAN DQGRNPGPLS ATATVYIEVE DENDNYPQFS EQNYVVQVPE DVGLNTAVLR  480
VQATDRDQGQ NAAIHYSILS GNVAGQFYLH SLSGILDVIN PLDFEDVQKY SLSIKAQDGG  540
RPPLINSSGV VSVQVLDVND NEPIFVSSPF QATVLENVPL GYPVVHIQAV DADSGENARL  600
HYRLVDTAST FLGGGSAGPK NPAPTPDFPF QIHNSSGWIT VCAELDREEV EHYSFGVEAV  660
DHGSPPMSSS TSVSITVLDV NDNDPVFTQP TYELRLNEDA AVGSSVLTLQ ARDRDANSVI  720
TYQLTGGNTR NRFALSSQRG GGLITLALPL DYKQEQQYVL AVTASDGTRS HTAHVLINVT  780
DANTHRPVFQ SSHYTVSVSE DRPVGTSIAT LSANDEDTGE NARITYVIQD PVPQFRIDPD  840
SGTMYTMMEL DYENQVAYTL TIMAQDNGIP QKSDTTTLEI LILDANDNAP QFLWDFYQGS  900
IFEDAPPSTS ILQVSATDRD SGPNGRLLYT FQGGDDGDGD FYIEPTSGVI RTQRRLDREN  960
VAVYNLWALA VDRGSPTPLS ASVEIQVTIL DINDNAPMFE KDELELFVEE NNPVGSVVAK  1020
IRANDPDEGP NAQIMYQIVE GDMRHFFQLD LLNGDLRAMV ELDFEVRREY VLVVQATSAP  1080
LVSRATVHIL LVDQNDNPPV LPDFQILFNN YVTNKSNSFP TGVIGCIPAH DPDVSDSLNY  1140
TFVQGNELRL LLLDPATGEL QLSRDLDNNR PLEALMEVSV SDGIHSVTAF CTLRVTIITD  1200
DMLTNSITVR LENMSQEKFL SPLLALFVEG VAAVLSTTKD DVFVFNVQND TDVSSNILNV  1260
TFSALLPGGV RGQFFPSEDL QEQIYLNRTL LTTISTQRVL PFDDNICLRE PCENYMKCVS  1320
```

```
VLRFDSSAPF LSSTTVLFRP IHPINGLRCR CPPGFTGDYC ETEIDLCYSD PCGANGRCRS  1380
REGGYTCECF EDFTGEHCEV DARSGRCANG VCKNGGTCVN LLIGGFHCVC PPGEYERPYC  1440
EVTTRSFPPQ SFVTFRGLRQ RFHFTISLTF ATQERNGLLL YNGRFNEKHD FIALEIVDEQ  1500
VQLTFSAGET TTTVAPKVPS GVSDGRWHSV QVQYYNKPNI GHLGLPHGPS GEKMAVVTVD  1560
DCDTTMAVRF GKDIGNYSCA AQGTQTGSKK SLDLTGPLLL GGVPNLPEDF PVHNRQFVGC  1620
MRNLSVDGKN VDMAGFIANN GTREGCAARR NFCDGRRCQN GGTCVNRWNM YLCECPLRFG  1680
GKNCEQAMPH PQLFSGESVV SWSDLNIIIS VPWYLGLMFR TRKEDSVLME ATSGGPTSFR  1740
LQILNNYLQF EVSHGPSDVE SVMLSGLRVT DGEWHHLLIE LKNVKEDSEM KHLVTMTLDY  1800
GMDQNKADIG GMLPGLTVRS VVVGGASEDK VSVRRGFRGC MQGVRMGGTP TNVATLNMNN  1860
ALKVRVKDGC DVDDPCTSSP CPPNSRCHDA WEDYSCVCDK GYLGINCVDA CHLNPCENMG  1920
ACVRSPGSPQ GYVCECGPSH YGPYCENKLD LPCPRGWWGN PVCGPCHCAV SKGFDPDCNK  1980
TNGQCQCKEN YYKLLAQDTC LPCDCFPHGS HSRTCDMATG QCACKPGVIG RQCNRCDNPF  2040
AEVTTLGCEV IYNGCPKAFE AGIWWPQTKF GQPAAVPCPK GSVGNAVRHC SGEKGWLPPE  2100
LFNCTTISFV DLRAMNEKLS RNETQVDGAR ALQLVRALRS ATQHTGTLFG NDVRTAYQLL  2160
GHVLQHESWQ QGFDLAATQD ADFHEDVIHS GSALLAPATR AAWEQIQRSE GGTAQLLRRL  2220
EGYFSNVARN VRRTYLRPFV IVTANMILAV DIFDKFNFTG ARVPRFDTIH EEFPRELESS  2280
VSFPADFFRP PEEKEGPLLR PAGRRTTPQT TRPGPGTERE APISRRRRHP DDAGQFAVAL  2340
VIIYRTLGQL LPERYDPDRR SLRLPHRPII NTPMVSTLVY SEGAPLPRPL ERPVLVEFAL  2400
LEVEERTKPV CVFWNHSLAV GGTGGWSARG CELLSRNRTH VACQCSHTAS FAVLMDISRR  2460
ENGEVLPLKI VTYAAVSLSL AALLVAFVLL SLVRMLRSNL HSIHKHLAVA LFLSQLVFVI  2520
GINQTENPFL CTVVAILLHY IYMSTFAWTL VESLHVYRML TEVRNIDTGP MRFYYVVGWG  2580
IPAIVTGLAV GLDPQGYGNP DFCWLSLQDT LIWSFAGPIG AVIIINTVTS VLSAKVSCQR  2640
KHHYYGKKGI VSLLRTAFLL LLLISATWLL GLLAVNRDAL SFHYLFAIFS GLQGPFVLLF  2700
HCVLNQEVRK HLKGVLGGRK LHLEDSATTR ATLLTRSLNC NTTFGDGPDM LRTDLGESTA  2760
SLDSIVRDEG IQKLGVSSGL VRGSHGEPDA SLMPRSCKDP PGHDSDSDSE LSLDEQSSSY  2820
ASSHSSDSED DGVGAEEKWD PARGAVHSTP KGDAVANHVP AGWPDQSLAE SDSEDPSGKP  2880
RLKVETKVSV ELHREEQGSH RGEYPPDQES GGAARLASSQ PPEQRKGILK NKVTYPPPLT  2940
LTEQTLKGRL REKLADCEQS PTSSRTSSLG SGGPDCAITV KSPGREPGRD HLNGVAMNVR  3000
TGSAQADGSD SEKP                                                     3014

SEQ ID NO: 24           moltype = AA  length = 449
FEATURE                 Location/Qualifiers
source                  1..449
                        mol_type = protein
                        organism = Homo sapiens
SEQUENCE: 24
MMKTLLLFVG LLLTWESGQV LGDQTVSDNE LQEMSNQGSK YVNKEIQNAV NGVKQIKTLI  60
EKTNEERKTL LSNLEEAKKK KEDALNETRE SETKLKELPG VCNETMMALW EECKPCLKQT  120
CMKFYARVCR SGSGLVGRQL EEFLNQSSPF YFWMNGDRID SLLENDRQQT HMLDVMQDHF  180
SRASSIIDEL FQDRFFTREP QDTYHYLPFS LPHRRPHFFF PKSRIVRSLM PFSPYEPLNF  240
HAMFQPFLEM IHEAQQAMDI HFHSPAFQHP PTEFIREGDD DRTVCREIRH NSTGCLRMKD  300
QCDKCREILS VDCSTNNPSQ AKLRRELDES LQVAERLTRK YNELLKSYQW KMLNTSSLLE  360
QLNEQFNWVS RLANLTQGED QYYLRVTTVA SHTSDSDVPS GVTEVVVKLF DSDPITVTVP  420
VEVSRKNPKF METVAEKALQ EYRKKHREE                                     449

SEQ ID NO: 25           moltype = AA  length = 612
FEATURE                 Location/Qualifiers
source                  1..612
                        mol_type = protein
                        organism = Homo sapiens
SEQUENCE: 25
LLLLGFLLVS LESTLSIPPW EAPKEHKYKA EEHTVVLTVT GEPCHFPFQY HRQLYHKCTH  60
KGRPGPQPWC ATTPNFDQDQ RWGYCLEPKK VKDHCSKHSP CQKGGTCVNM PSGPHCLCPQ  120
HLTGNHCQKE KCFEPQLLRF FHKNEIWYRT EQAAVARCQC KGPDAHCQRL ASQACRTNPC  180
LHGGRCLEVE GHRLCHCPVG YTGPFCDVDT KASCYDGRGL SYRGLARTTL SGAPCQPWAS  240
EATYRNVTAE QARNWGLGGH AFCRNPDNDI RPWCFVLNRD RLSWEYCDLA QCQTPTQAAP  300
PTPVSPRLHV PLMPAQPAPP KPQPTTRTPP QSQTPGALPA KREQPPSLTR NGPLSCGQRL  360
RKSLSSMTRV VGGLVALRGA HPYIAALYWG HSFCAGSLIA PCWVLTAAHC LQDRPAPEDL  420
TVVLGQERRN HSCEPCQTLA VRSYRLHEAF SPVSYQHDLA LLRLQEDADG SCALLSPYVQ  480
PVCLPSGAAR PSETTLCQVA GWGHQFEGAE EYASFLQEAQ VPFLSLERCS APDVHGSSIL  540
PGMLCAGFLE GGTDACQGDS GGPLVCEDQA AERRLTLQGI ISWGSGCGDR NKPGVYTDVA  600
YYLAWIREHT VS                                                       612

SEQ ID NO: 26           moltype = AA  length = 1744
FEATURE                 Location/Qualifiers
source                  1..1744
                        mol_type = protein
                        organism = Homo sapiens
SEQUENCE: 26
MRLLWGLIWA SSFFTLSLQK PRLLLFSPSV VHLGVPLSVG VQLQDVPRGQ VVKGSVFLRN  60
PSRNNVPCSP KVDFTLSSER DFALLSLQVP LKDAKSCGLH QLLRGPEVQL VAHSPWLKDS  120
LSRTTNIQGI NLLFSSRRGH LFLQTDQPIY NPGQRVRYRV FALDQKMRPS TDTITVMVEN  180
SHGLRVRKKE VYMPSSIFQD DFVIPDISEP GTWKISARFS DGLESNSSTQ FEVKKYVLPN  240
FEVKITPGKP YILTVPGHLD EMQLDIQARY IYGKPVQGVA YVRFGLLDED GKKTFFRGLE  300
SQTKLVNGQS HISLSKAEFQ DALEKLNMGI TDLQGLRLYV AAAIIESPGG EMEEAELTSW  360
YFVSSPFSLD LSKTKRHLVP GAPFLLQALV REMSGSPASG IPVKVSATVS SPGSVPEVQD  420
IQQNTDGSGQ VSIPIIIPQT ISELQLSVSA GSPHPAIARL TVAAPPSGGP GFLSIERPDS  480
RPPRVGDTLN LNLRAVGSGA TFSHYYYMIL SRGQIVFMNR EPKRTLTSVS VFVDHHLAPS  540
FYFVAFYYHG DHPVANSLRV DVQAGACEGK LELSVDGAKQ YRNGESVKLH LETDSLALVA  600
```

```
LGALDTALYA AGSKSHKPLN MGKVFEAMNS YDLGCGPGGG DSALQVFQAA GLAFSDGDQW  660
TLSRKRLSCP KEKTTRKKRN VNFQKAINEK LGQYASPTAK RCCQDGVTRL PMMRSCEQRA  720
ARVQQPDCRE PFLSCCQFAE SLRKKSRDKG QAGLQRALEI LQEEDLIDED DIPVRSFFPE  780
NWLWRVETVD RFQILTLWLP DSLTTWEIHG LSLSKTKGLC VATPVQLRVF REFHLHLRLP  840
MSVRRFEQLE LRPVLYNYLD KNLTVSVHVS PVEGLCLAGG GGLAQQVLVP AGSARPVAFS  900
VVPTAAAAVS LKVVARGSFE FPVGDAVSKV LQIEKEGAIH REELVYELNP LDHRGRTLEI  960
PGNSDPNMIP DGDFNSYVRV TASDPLDTLG SEGALSPGGV ASLLRLPRGC GEQTMIYLAP  1020
TLAASRYLDK TEQWSTLPPE TKDHAVDLIQ KGYMRIQQFR KADGSYAAWL SRDSSTWLTA  1080
FVLKVLSLAQ EQVGGSPEKL QETSNWLLSQ QQADGSFQDP CPVLDRSMQG GLVGNDETVA  1140
LTAFVTIALH HGLAVFQDEG AEPLKQRVEA SISKANSFLG EKASAGLLGA HAAAITAYAL  1200
TLTKAPVDLL GVAHNNLMAM AQETGDNLYW GSVTGSQSNA VSPTPAPRNP SDPMPQAPAL  1260
WIETTAYALL HLLLHEGKAE MADQASAWLT RQGSFQGGFR STQDTVIALD ALSAYWIASH  1320
TTEERGLNVT LSSTGRNGFK SHALQLNNRQ IRGLEEELQF SLGSKINVKV GGNSKGTLKV  1380
LRTYNVLDMK NTTCQDLQIE VTVKGHVEYT MEANEDYEDY EYDELPAKDD PDAPLQPVTP  1440
LQLFEGRRNR RRREAPKVVE EQESRVHYTV CIWRNGKVGL SGMAIADVTL LSGFHALRAD  1500
LEKLTSLSDR YVSHFETEGP HVLLYFDSVP TSRECVGFEA VQEVPVGLVQ PASATLYDYY  1560
NPERRCSVFY GAPSKSRLLA TLCSAEVCQC AEGKCPRQRR ALERGLQDED GYRMKFACYY  1620
PRVEYGFQVK VLREDSRAAF RLFETKITQV LHFTKDVKAA ANQMRNFLVR ASCRLRLEPG  1680
KEYLIMGLDG ATYDLEGHPQ YLLDSNSWIE EMPSERLCRS TRQRAACAQL NDFLQEYGTQ  1740
GCQV                                                              1744

SEQ ID NO: 27          moltype = AA  length = 559
FEATURE                Location/Qualifiers
source                 1..559
                       mol_type = protein
                       organism = Homo sapiens
SEQUENCE: 27
MSACRSFAVA ICILEISILT AQYTTSYDPE LTESSGSASH IDCRMSPWSE WSQCDPCLRQ  60
MFRSRSIEVF GQFNGKRCTD AVGDRRQCVP TEPCEDAEDD CGNDFQCSTG RCIKMRLRCN  120
GDNDCGDFSD EDDCESEPRP PCRDRVVEES ELARTAGYGI NILGMDPLST PFDNEFYNGL  180
CNRDRDGNTL TYYRRPWNVA SLIYETKGEK NFRTEHYEEQ IEAFKSIIQE KTSNFNAAIS  240
LKFTPTETNK AEQCCEETAS SISLHGKGSF RFSYSKNETY QLFLSYSSKK EKMFLHVKGE  300
IHLGRFVMRN RDVVLTTTFV DDIKALPTTY EKGEYFAFLE TYGTHYSSSG SLGGLYELIY  360
VLDKASMKRK GVELKDIKRC LGYHLDVSLA FSEISVGAEF NKDDCVKRGE GRAVNITSEN  420
LIDDVVSLIR GGTRKYAFEL KEKLLRGTVI DVTDFVNWAS SINDAPVLIS QKLSPIYNLV  480
PVKMKNAHLK KQNLERAIED YINEFSVRKC HTCQNGGTVI LMDGKCLCAC PFKFEGIACE  540
ISKQKISEGL PALEFPNEK                                              559

SEQ ID NO: 28          moltype = AA  length = 1231
FEATURE                Location/Qualifiers
source                 1..1231
                       mol_type = protein
                       organism = Homo sapiens
SEQUENCE: 28
MRLLAKIICL MLWAICVAED CNELPPRRNT EILTGSWSDQ TYPEGTQAIY KCRPGYRSLG  60
NIIMVCRKGE WVALNPLRKC QKRPCGHPGD TPFGTFTLTG GNVFEYGVKA VYTCNEGYQL  120
LGEINYRECD TDGWTNDIPI CEVVKCLPVT APENGKIVSS AMEPDREYHF GQAVRFVCNS  180
GYKIEGDEEM HCSDDGFWSK EKPKCVEISC KSPDVINGSP ISQKIIYKEN ERFQYKCNMG  240
YEYSERGDAV CTESGWRPLP SCEEKSCDNP YIPNGDYSPL RIKHRTGDEI TYQCRNGFYP  300
ATRGNTAKCT STGWIPAPRC TLKPCDYPDI KHGGLYHENM RRPYFPVAVG KYYSYYCDEH  360
FETPSGSYWD HIHCTQDGWS PAVPCLRKCY FPYLENGYNQ NYGRKFVQGK SIDVACHPGY  420
ALPKAQTTVT CMENGWSPTP RCIRVKTCSK SSIDIENGFI SESQYTYALK EKAKYQCKLG  480
YVTADGETSG SITCGKDGWS AQPTCIKSCD IPVFMNARTK NDFTWFKLND TLDYECHDGY  540
ESNTGSTTGS IVCGYNGWSD LPICYERECE LPKIDVHLVP DRKKDQYKVG EVLKFSCKPG  600
FTIVGPNSVQ CYHFGLSPDL PICKEQVQSC GPPPELLNGN VKEKTKEEYG HSEVVEYYCN  660
PRFLMKGPNK IQCVDGEWTT LPVCIVEEST CGDIPELEHG WAQLSSPPYY YGDSVEFNCS  720
ESFTMIGHRS ITCIHGVWTQ LPQCVAIDKL KKCKSSNLII LEEHLKNKKE FDHNSNIRYR  780
CRGKEGWIHT VCINGRWDPE VNCSMAQIQL CPPPPQIPNS HNMTTTLNYR DGEKVSVLCQ  840
ENYLIQEGEE ITCKDGRWQS IPLCVEKIPC SQPPQIEHGT INSSRSSQES YAHGTKLSYT  900
CEGGFRISEE NETTCYMGKW SSPPQCEGLP CKSPPEISHG VVAHMSDSYQ YGEEVTYKCF  960
EGFGIDGPAI AKCLGEKWSH PPSCIKTDCL SLPSFENAIP MGEKKDVYKA GEQVTYTCAT  1020
YYKMDGASNV TCINSRWTGR PTCRDTSCVN PPTVQNAYIV SRQMSKYPSG ERVRYQCRSP  1080
YEMFGDEEVM CLNGNWTEPP QCKDSTGKCG PPPPIDNGDI TSFPLSVYAP ASSVEYQCQN  1140
LYQLEGNKRI TCRNGQWSEP PKCLHPCVIS REIMENYNIA LRWTAKQKLY SRTGESVEFV  1200
CKRGYRLSSR SHTLRTTCWD GKLEYPTCAK R                                1231

SEQ ID NO: 29          moltype = AA  length = 330
FEATURE                Location/Qualifiers
source                 1..330
                       mol_type = protein
                       organism = Homo sapiens
SEQUENCE: 29
MWLLVSVILI SRISSVGGEA TFCDFPKINH GILYDEEKYK PFSQVPTGEV FYYSCEYNFV  60
SPSKSFWTRI TCTEEGWSPT PKCLRLCFFP FVENGHSESS GQTHLEGDTV QIICNTGYRL  120
QNNENNISCV ERGWSTPPKC RSTDTSCVNP PTVQNAHILS RQMSKYPSGE RVRYECRSPY  180
EMFGDEEVMC LNGNWTEPPQ CKDSTGKCGP PPPIDNGDIT SFPLSVYAPA SSVEYQCQNL  240
YQLEGNKRIT CRNGQWSEPP KCLHPCVISR EIMENYNIAL RWTAKQKLYL RTGESAEFVC  300
KRGYRLSSRS HTLRTTCWDG KLEYPTCAKR                                  330
```

-continued

```
SEQ ID NO: 30          moltype = AA  length = 1782
FEATURE                Location/Qualifiers
source                 1..1782
                       mol_type = protein
                       organism = Homo sapiens
SEQUENCE: 30
MSRGFWLAEP LAGTGPHPAP VAADSRGCSS VPRRHAPSRL SVSTPSRGPG ARMVGELRYR  60
EFRVPLGPGL HAYPDELIRQ RVGHDGHPEY QIRWLILRRG DEGDGGSGQV DCKAEHILLW  120
MSKDEIYANC HKMLGEDGQV IGPSQESAGE VGALDKSVLE EMETDVKSLI QRALRQLEEC  180
VGTIPPAPLL HTVHVLSAYA SIEPLTGVFK DPRVLDLLMH MLSSPDYQIR WSAGRMIQAL  240
SSHDAGEGQC GEEGKAGEGL GRLRDSQDTV AGASDLIRTR TQILLSLSQQ EAIEKHLDFD  300
SRCALLALFA QATLSEHPMS FEGIQLPQVP GRVLFSLVKR YLHVTSLLDQ LNDSAAEPGA  360
QNTSAPEELS GERGQLELEF SMAMGTLISE LVQAMRWDQA SDRPRSSARS PGSIFQPQLA  420
DVSPGLPAAQ AQPSFRRSRR FRPRSEFASG NTYALYVRDT LQPGMRVRML DDYEEISAGD  480
EGEFRQSNNG VPPVQVFWES TGRTYWVHWH MLEILGFEED IEDMVEADEY QGAVASRVLG  540
RALPAWRWRP MTELYAVPYV LPEDEDTEEC EHLTLAEWWE LLFFIKKLDG PDHQEVLQIL  600
QENLDGEILD DEILAELAVP IELAQDLLLT LPQRLNDSAL RDLINCHVYK KYGPEALAGN  660
QAYPSLLEAQ EDVLLLDAQA QAKDSEDAAK VEAKEPPSQS PNTPLQRLVE GYGPAGKILL  720
DLEQALSSEG TQENKVKPLL LQLQRQPQPF LALMQSLDTP ETNRTLHLTV LRILKQLVDF  780
PEALLLPWHE AVDACMACLR SPNTDREVLQ ELIFFLHRLT SVSRDYAVVL NQLGARDAIS  840
KALEKHLGKL ELAQELRDMV FKCEKHAHLY RKLITNILGG CIQMVLGQIE DHRRTHQPIN  900
IPFFDVFLRY LCQGSSVEVK EDKCWEKVEV SSNPHRASKL TDHNPKTYWE SNGSAGSHYI  960
TLHMRRGILI RQLTLLVASE DSSYMPARVV VCGGDSTSSL HTELNSVNVM PSASRVILLE  1020
NLTRFWPIIQ IRIKRCQQGG IDTRIRGLEI LGPKPTFWPV FREQLCRHTR LFYMVRAQAW  1080
SQDMAEDRRS LLHLSSRLNG ALRQEQNFAD RFLPDDEAAQ ALGKTCWEAL VSPVVQNITS  1140
PDEDGISPLG WLLDQYLECQ EAVFNPQSRG PAFFSRVRRL THLLVHVEPC EAPPPVVATP  1200
RPKGRNRSHD WSSLATRGLP SSIMRNLTRC WRAVVEKQVN NFLTSSWRDD DFVPRYCEHF  1260
NILQNSSSEL FGPRAAFLLA LQNGCAGALL KLPFLKAAHV SEQFARHIDQ QIQGSRIGGA  1320
QEMERLAQLQ QCLQAVLIFS GLEIATTFEH YYQHYMADRL LGVVSSWLEG AVLEQIGPCF  1380
PNRLPQQMLQ SLSTSKELQR QFHVYQLQQL DQELLKLEDT EKKIQVGLGA SGKEHKSEKE  1440
EEAGAAAVVD VAEGEEEEEE NEDLYYEGAM PEVSVLVLSR HSWPVASICH TLNPRTCLPS  1500
YLRGTLNRYS NFYNKSQSHP ALERGSQRRL QWTWLGWAEL QFGNQTLHVS TVQMWLLLYL  1560
NDLKAVSVES LLAFSGLSAD MLNQAIGPLT SSRGPLDLHE QKDIPGGVLK IRDGSKEPRS  1620
RWDIVRLIPP QTYLQAEGED GQNLEKRRNL LNCLIVRILK AHGDEGLHID QLVCLVLEAW  1680
QKGPCPPRGL VSSLGKGSAC SSTDVLSCIL HLLGKGTLRR HDDRPQVLSY AVPVTVMEPH  1740
TESLNPGSSG PNPPLTFHTL QIRSRGVPYA SCTATQSFST FR                    1782

SEQ ID NO: 31          moltype = AA  length = 894
FEATURE                Location/Qualifiers
source                 1..894
                       mol_type = protein
                       organism = Homo sapiens
SEQUENCE: 31
MALASAAPGS IFCKQLLFSL LVLTLLCDAC QKVYLRVPSH LQAETLVGKV NLEECLKSAS  60
LIRSSDPAFR ILEDGSIYTT HDLILSSERK SFSIFLSDGQ RREQQEIKVV LSARENKSPK  120
KRHTKDTALK RSKRRWAPIP ASLMENSLGP FPQHVQQIQS DAAQNYTIFY SISGPGVDKE  180
PFNLFYIEKD TGDIFCTRSI DREKYEQFAL YGYATTADGY APEYPLPLII KIEDDNDNAP  240
YFEHRVTIFT VPENCRSGTS VGKVTATDLD EPDTLHTRLK YKILQQIPDH PKHFSIHPDT  300
GVITTTTPFL DREKCDTYQL IMEVRDMGGQ PFGLFNTGTI TISLEDENDN PPSFTETSYV  360
TEVEENRIDV EILRMKVQDQ DLPNTPHSKA VYKILQGNEN GNFIISTDPN TNEGVLCVVK  420
PLNYEVNRQV ILQVGVINEA QFSKAASSQT PTMCTTTVTV KIIDSDEGPE CHPPVKVIQS  480
QDGFPAGQEL LGYKALDPEI SSGEGLRYQK LGDEDNWFEI NQHTGDLRTL KVLDRESKFV  540
KNNQYNISVV AVDAVGRSCT GTLVVHLDDY NDHAPQIDKE VTICQNNEDF AVLKPVDPDG  600
PENGPPFQFF LDNSASKNWN IEEKDGKTAI LRQRQNLDYN YYSVPIQIKD RHGLVATHML  660
TVRVCDCSTP SECRMKDKST RDVRPNVILG RWAILAMVLG SVLLLCILFT CFCVTAKRTV  720
KKCFPEDIAQ QNLIVSNTEG PGEEVTEANI RLPMQTSNIC DTSMSVGTVG GQGIKTQQSF  780
EMVKGGYTLD SNKGGGHQTL ESVKGVGQGD TGRYAYTDWQ SFTQPRLGEK VYLCGQDEEH  840
KHCEDYVCSY NYEGKGSLAG SVGCCSDRQE EEGLEFLDHL EPKFRTLAKT CIKK        894

SEQ ID NO: 32          moltype = AA  length = 824
FEATURE                Location/Qualifiers
source                 1..824
                       mol_type = protein
                       organism = Homo sapiens
SEQUENCE: 32
MRGLGLWLLG AMMLPAIAPS RPWALMEQYE VVLPWRLPGP RVRRALPSHL GLHPERVSYV  60
LGATGHNFTL HLRKNRDLLG SGYTETYTAA NGSEVTEQPR GQDHCFYQGH VEGYPDSAAS  120
LSTCAGLRGF FQVGSDLHLI EPLDEGGEGG RHAVYQAEHL LQTAGTCGVS DDSLGSLLGP  180
RTAAVFRPRP GDSLPSRETR YVELYVVVDN AEFQMLGSEA AVRHRVLEVV NHVDKLYQKL  240
NFRVVLVGLE IWNSQDRFHV SPDPSVTLEN LLTWQARQRT RRHLHDNVQL ITGVDFTGTT  300
VGFARVSAMC SHSSGAVNQD HSKNPVGVAC TMAHEMGHNL GMDHDENVQG CRCQERFEAG  360
RCIMAGSIGS SFPRMFSDCS QAYLESFLER PQSVCLANAP DLSHLVGGPV CGNLFVERGE  420
QCDCGPPEDC RNRCCNSTTC QLAEGAQCAH GTCCQECKVK PAGELCRPKK DMCDLEEFCD  480
GRHPECPEDA FQENGTPCSG GYCYNGACPT LAQQCQAFWG PGGQAAEESC FSYDILPGCK  540
ASRYRADMCG VLQCKGGQQP LGRAICIVDV CHALTTEDGT AYEPVPEGTR CGPEKVCWKG  600
RCQDLHVYRS SNCSAQCHNH GVCNHKQECH CHAGWAPPHC AKLLTEVHAA SGSLPVFVVV  660
VLVLLAVVLV TLAGIIVYRK ARSRILSRNV APKTTMGRSN PLFHQAASRV PAKGGAPAPS  720
RGPQELVPTT HPGQPARHPA SSVALKRPPP APPVTVSSPP FPVPVYTRQA PKQVIKPTFA  780
PPVPPVKPGA GAANPGPAEG AVGPKVALKP PIQRKQGAGA PTAP                  824
```

```
SEQ ID NO: 33          moltype = AA  length = 1401
FEATURE                Location/Qualifiers
source                 1..1401
                       mol_type = protein
                       organism = Homo sapiens
SEQUENCE: 33
MDGDSSSSSG GSGPAPGPGP EGEQRPEGEP LAPDGGSPDS TQTKAVPPEA SPERSCSLHS  60
CPLEDPSSSS GPPPTTSTLQ PVGPSSPLAP AHFTYPRALQ EYQGGSSLPG LGDRAALCSH  120
GSSLSPSPAP SQRDGTWKPP AVQHHVVSVR QERAFQMPKS YSQLIAEWPV AVLMLCLAVI  180
FLCTLAGLLG ARLPPDFSKPL LGFEPRDTDI GSKLVVWRAL QALTGPRKLL FLSPDLELNS  240
SSSHNTLRPA PRGSAQESAV RPRRMVEPLE DRRQENFFCG PPEKSYAKLV FMSTSSGSLW  300
NLHAIHSMCR MEQDQIRSHT SFGALCQRTA ANQCCPSWSL GNYLAVLSNR SSCLDTTQAD  360
AARTLALLRT CALYYHSGAL VPSCLGPGQN KSPRCAQVPT KCSQSSAIYQ LLHFLLDRDF  420
LSPQTTDYQV PSLKYSLLFL PTPKGASLMD IYLDRLATPW GLADNYTSVT GMDLGLKQEL  480
LRHFLVQDTV YPLLALVAIF FGMALYLRSL FLTLMVLLGV LGSLLVAFFL YQVAFRMAYF  540
PFVNLAALLL LSSVCANHTL IFFDLWRLSK SQLPSGGLAQ RVGRTMHHFG YLLLVSGLTT  600
SAAFYASYLS RLPAVRCLAL FMGTAVLVHL ALTLVWLPAS AVLHERYLAR GCARRARGRW  660
EGSAPRRLLL ALHRRLRGLR RAAGTSRLL FQRLLPCGVI KFRYIWICWF AALAAGGAYI  720
AGVSPRLRLP TLPPPGGQVF RPSHPFERFD AEYRQLFLFE QLPQGEGGHM PVVLVWGVLP  780
VDTGDPLDPR SNSSLVRDPA FSASGPEAQR WLLALCHRAR NQSFFDTLQE GWPTLCFVET  840
LQRWMESPSC ARLGPDLCCG HSDFPWAPQF FLHCLKMMAL EQGPDGTQDL GLRFDAHGSL  900
AALVLQFQTN FRNSPDYNQT QLFYNEVSHW LAAELGMAPP GLRRGWFTSR LELYSLQHSL  960
STEPAVVLGL ALALAFATLL LGTWNVPLSL FSVAAVAGTV LLTVGLLVLL EWQLNTAEAL  1020
FLSASVGLSV DFTVNYCISY HLCPHPDRLS RVAFSLRQTS CATAVGAAAL FAAGVLMLPA  1080
TVLLYRKLGI ILMMVKCVSC GFASFFFQSL CCFFGPEKNC GQILWPCAHL PWDAGTGDPG  1140
GEKAGRPRPG SVGGMPGSCS EQYELQPLAR RRSPSFDTST ATSKLSHRPS VLSEDLQLHD  1200
GPCCSRPPPA PASPRELLLD HQAVFSQCPA LQTSSPYKQA GPSPKTRARQ DSQGEEAEPL  1260
PASPEAPAHS PKAKAADPPD GFCSSASTLE GLSVSDETCL STSEPSARVP DSVGVSPDDL  1320
DDTGQPVLER GQLNGKRDTL WLALRETVYD PSLPASHHSS LSWKGRGGPG DGSPVVLPNS  1380
QPDLPDVWLR RPSTHTSGYS S                                          1401

SEQ ID NO: 34          moltype = AA  length = 434
FEATURE                Location/Qualifiers
source                 1..434
                       mol_type = protein
                       organism = Homo sapiens
SEQUENCE: 34
MSILKIHARE IFDSRGNPTV EVDLFTSKGL FRAAVPSGAS TGIYEALELR DNDKTRYMGK  60
GVSKAVEHIN KTIAPALVSK KLNVTEQEKI DKLMIEMDGT ENKSKFGANA ILGVSLAVCK  120
AGAVEKGVPL YRHIADLAGN SEVILPVPAF NVINGGSHAG NKLAMQEFMI LPVGAANFRE  180
AMRIGAEVYH NLKNVIKEKY GKDATNVGDE GGFAPNILEN KEGLELLKTA IGKAGYTDKV  240
VIGMDVAASE FFRSGKYDLD FKSPDDPSRY ISPDQLADLY KSFIKDYPVV SIEDPFDQDD  300
WGAWQKFTAS AGIQVVGDDL TVTNPKRIAK AVNEKSCNCL LLKVNQIGSV TESLQACKLA  360
QANGWGVMVS HRSGETEDTF IADLVVGLCT GQIKTGAPCR SERLAKYNQL LRIEEELGSK  420
AKFAGRNFRN PLAK                                                  434

SEQ ID NO: 35          moltype = AA  length = 135
FEATURE                Location/Qualifiers
source                 1..135
                       mol_type = protein
                       organism = Homo sapiens
SEQUENCE: 35
MATVQQLEGR WRLVDSKGFD EYMKELGVGI ALRKMGAMAK PDCIITCDGK NLTIKTESTL  60
KTTQFSCTLG EKFEETTADG RKTQTVCNFT DGALVQHQEW DGKESTITRK LKDGKLVVEC  120
VMNNVTCTRI YEKVE                                                 135

SEQ ID NO: 36          moltype = AA  length = 1322
FEATURE                Location/Qualifiers
source                 1..1322
                       mol_type = protein
                       organism = Homo sapiens
SEQUENCE: 36
MDVFSFVKIA KLSSHRTKSS GWPPPSGTWG LSQVPPYGWE MTANRDGRDY FINHMTQAIP  60
FDDPRLESCQ IIPPAPRKVE MRRDPVLGFG FVAGSEKPVV VRSVTPGGPS EGKLIPGDQI  120
VMINDEPVSA APRERVIDLV RSCKESILLT VIQPYPSPKS AFISAAKKAR LKSNPVKVRF  180
SEEVIINGQV SETVKDNSLL FMPNVLKVYL ENGQTKSFRF DCSTSIKDVI LTLQEKLSIK  240
GIEHFSLMLE QRTEGAGTKL LLLHEQETLT QVTQRPSSHK MRCLFRISFV PKDPIDLLRR  300
DPVAFEYLYV QSCNDVVQER FGPELKYDIA LRLAALQMYI ATVTTKQTQK ISLKYIEKEW  360
GLETFLPSAV LQSMKEKNIK KALSHLVKAN QNLVPPGKKL SALQAKVHYL KFLSDLRLYG  420
GRVFKATLVQ AEKRSEVTLL VGPRYGISHV INTKTNLVAL LADFSHVNRI EMFSEEESLV  480
RVELHVLDVK PITLLMESSD AMNLACLTAG YYRLLVDSRR SIFNMANKKN TATQETGPEN  540
KGKHNLLGPD WNCIPQMTTF IGEGEQEAQI TYIDSKQKTV EITDSTMCPK EHRHLYIDNA  600
YSSDGLNQQL SQPGEAPCEA DYRSLAQRSL LTLSGPETLK KAQESPRGAK VSFIFGDFAL  660
DDGISPPTLG YETLLDEGPE MLEKQRNLYI GSANDMKGLD LTPEAEGIQF VENSVYANIG  720
DVKSFQAAEG IEEPLLHDIC YAENTDDAED EDEVSCEEDL VVGEMNQPAI LNLSGSSDDI  780
IDLTSLPPPE GDDNEDDFLL RSLNMAIAAP PPGFRDSSDE EDSQSQAASF PEDKEKGSSL  840
QNDEIPVSLI DAVPTSAEGK CEKGLDNAVV STLGALEALS VSEEQQTSDN SGVAILRAYS  900
PESSSDSGNE TNSSEMTESS ELATAQKQSE NLSRMFLATH EGYHPLAEEQ TEFPASKTPA  960
```

```
GGLPPKSSHA LAARPATDLP PKVVPSKQLL HSDHMEMEPE TMETKSVTDY FSKLHMGSVA  1020
YSCTSKRKSK LADGEGKAPP NGNTTGKKQQ GTKTAEMEEE ASGKFGTVSS RDSQHLSTFN  1080
LERTAFRKDS QRWYVATEGG MAEKSGLEAA TGKTFPRASG LGAREAEGKE EGAPDGETSD  1140
GSGLGQGDRF LTDVTCASSA KDLDNPEDAD SSTCDHPSKL PEADESVARL CDYHLAKRMS  1200
SLQSEGHFSL QSSQGSSVDA GCGTGSSGSA CATPVESPLC PSLGKHLIPD ASGKGVNYIP  1260
SEERAPGLPN HGATFKELHP QTEGMCPRMT VPALHTAINT EPLFGTLRDG CHRLPKIKET  1320
TV                                                                 1322

SEQ ID NO: 37          moltype = AA  length = 382
FEATURE                Location/Qualifiers
source                 1..382
                       mol_type = protein
                       organism = Homo sapiens
SEQUENCE: 37
MGLLLPLALC ILVLCCGAMS PPQLALNPSA LLSRGCNDSD VLAVAGFALR DINKDRKDGY  60
VLRLNRVNDA QEYRRGGLGS LFYLTLDVLE TDCHVLRKKA WQDCGMRIFF ESVYGQCKAI  120
FYMNNPSRVL YLAAYNCTLR PVSKKKIYMT CPDCPSSIPT DSSNHQVLEA ATESLAKYNN  180
ENTSKQYSLF KVTRASSQWV VGPSYFVEYL IKESPCTKSQ ASSCSLQSSD SVPVGLCKGS  240
LTRTHWEKFV SVTCDFFESQ APATGSENSA VNQKPTNLPK VEESQQKNTP PTDSPSKAGP  300
RGSVQYLPDL DDKNSQEKGP QEAFPVHLDL TTNPQGETLD ISFLFLEPME EKLVVLPFPK  360
EKARTAECPG PAQNASPLVL PP                                           382

SEQ ID NO: 38          moltype = AA  length = 2871
FEATURE                Location/Qualifiers
source                 1..2871
                       mol_type = protein
                       organism = Homo sapiens
SEQUENCE: 38
MRRGRLLEIA LGFTVLLASY TSHGADANLE AGNVKETRAS RAKRRGGGGH DALKGPNVCG  60
SRYNAYCCPG WKTLPGGNQC IVPICRHSCG DGFCSRPNMC TCPSGQIAPS CGSRSIQHCN  120
IRCMNGGSCS DDHCLCQKGY IGTHCGQPVC ESGCLNGGRC VAPNRCACTY GFTGPQCERD  180
YRTGPCFTVI SNQMCQGQLS GIVCTKTLCC ATVGRAWGHP CEMCPAQPHP CRRGFIPNIR  240
TGACQDVDEC QAIPGLCQGG NCINTVGSFE CKCPAGHKLN EVSQKCEDID ECSTIPGICE  300
GGECTNTVSS YFCKCPPGFY TSPDGTRCID VRPGYCYTAL TNGRCSNQLP QSITKMQCCC  360
DAGRCWSPGV TVAPEMCPIR ATEDFNKLCS VPMVIPGRPE YPPPPLGPIP PVLPVPPGFP  420
PGPQIPVPRP PVEYLYPSRE PPRVLPVNVT DYCQLVRYLC QNGRCIPTPG SYRCECNKGF  480
QLDLRGECID VDECEKNPCA GGECINNQGS YTCQCRAGYQ STLTRTECRD IDECLQNGRI  540
CNNGRCINTD GSFHCVCNAG FHVTRDGKNC EDMDECSIRN MCLNGMCINE DGSFKCICKP  600
GFQLASDGRY CKDINECETP GICMNGRCVN TDGSYRCECF PGLAVGLDGR VCVDTHMRST  660
CYGGYKRGQC IKPLFGAVTK SECCCASTEY AFGEPCQPCP AQNSAEYQAL CSSGPGMTSA  720
GSDINECALD PDICPNGICE NLRGTYKCIC NSGYEVDSTG KNCVDINECV LNSLLCDNGQ  780
CRNTPGSFVC TCPKGFIYKP DLKTCEDIDE CESSPCINGV CKNSPGSFIC ECSSESTLDP  840
TKTICIETIK GTCWQTVIDG RCEININGAT LKSQCCSSLG AAWGSPCTLC QVDPICGKGY  900
SRIKGTQCED IDECEVFPGV CKNGLCVNTR GSFKCQCPSG MTLDATGRIC LDIRLETCFL  960
RYEDEECTLP IAGRHRMDAC CCSVGAAWGT EECEECPMRN TPEYEELCPR GPGFATKEIT  1020
NGKPFFKDIN ECKMIPSLCT HGKCRNTIGS FKCRCDSGFA LDSEERNCTD IDECRISPDL  1080
CGRGQCVNTP GDFECKCDEG YESGFMMMKN CMDIDECQRD PLLCRGGVCH NTEGSYRCEC  1140
PPGHQLSPNI SACIDINECE LSAHLCPNGR CVNLIGKYQC ACNPGYHSTP DRLFCVDIDE  1200
CSIMNGGCET FCTNSEGSYE CSCQPGFALM PDQRSCTDID ECEDNPNICD GGQCTNIPGE  1260
YRCLCYDGFM ASEDMKTCVD VNECDLNPNI CLSGTCENTK GSFICHCDMG YSGKKGKTGC  1320
TDINECEIGA HNCGKHAVCT NTAGSFKCSC SPGWIGDGIK CTDLDECSNG THMCSQHADC  1380
KNTMGSYRCL CKEGYTGDGF TCTDLDECSE NLNLCGNGQC LNAPGGYRCE CDMGFVPSAD  1440
GKACEDIDEC SLPNICVFGT CHNLPGLFRC ECEIGYELDR SGGNCTDVNE CLDPTTCISG  1500
NCVNTPGSYI CDCPPDFELN PTRVGCVDTR SGNCYLDIRP RGDNGDTACS NEIGVGVSKA  1560
SCCCSLGKAW GTPCEMCPAV NTSEYKILCP GGEGFRPNPI TVILEDIDEC QELPGLCQGG  1620
KCINTFGSFQ CRCPTGYYLN EDTRVCDDVN ECETPGICGP GTCYNTVGNY TCICPPDYMQ  1680
VNGGNNCMDM RRSLCYRNYY ADNQTCDGEL LFNMTKKMCC CSYNIGRAWN KPCEQCPIPS  1740
TDEFATLCGS QRPGFVIDIY TGLPVDIDEC REIPGVCENG VCINMVGSFR CECPVGFFYN  1800
DKLLVCEDID ECQNGPVCQR NAECINTAGS YRCDCKPGYR FTSTGQCNDR NECQEIPNIC  1860
SHGQCIDTVG SFYCLCHTGF KTNDDQTMCL DINECERDAC GNGTCRNTIG SFNCRCNHGF  1920
ILSHNNDCID VDECASGNGN LCRNGQCINT VGSFQCQCNE GYEVAPDGRT CVDINECLLE  1980
PRKCAPGTCQ NLDGSYRCIC PPGYSLQNEK CEDIDECVEE PEICALGTCS NTEGSFKCLC  2040
PEGFSLSSSG RRCQDLRMSY CYAKFEGGKC SSPKSRNHSK QECCCALKGE GWGDPCELCP  2100
TEPDEAFRQI CPYGSGIIVG PDDSAVDMDE CKEPDVCKHG QCINTDGSYR CECPFGYILA  2160
GNECVDTDEC SVGNPCGNGT CKNVIGGFEC TCEEGFEPGP MMTCEDINEC AQNPLLCAFR  2220
CVNTYGSYEC KCPVGYVLRE DRRMCKDEDE CEEGKHDCTE KQMECKNLIG TYMCICGPGY  2280
QRRPDGEGCV DENECQTKPG ICENGRCLNT RGSYTCECND GFTASPNQDE CLDNREGYCF  2340
TEVLQNMCQI GSSNRNPVTK SECCCDGGRG WGPHCEICPF QGTVAFKKLC PHGRGFMTNG  2400
ADIDECKVIH DVCRNGECVN DRGSYHCICK TGYTPDITGT SCVDLNECNQ APKPCNFICK  2460
NTEGSYQCSC PKGYILQEDG RSCKDLDECA TKQHNCQFLC VNTIGGFTCK CPPGFTQHHT  2520
SCIDNNECTS DINLCGSKGI CQNTPGSFTC ECQRGFSLDQ TGSSCEDVDE CEGNHRCQHG  2580
CQNIIGGYRC SCPQGYLQHY QWNQCVDENE CLSAHICGGA SCHNTLGSYK CMCPAGFQYE  2640
QFSGGCQDIN ECGSAQAPCS YGCSNTEGGY LCGCPPGYFR IGQGHCVSGM GMGRGNPEPP  2700
VSGEMDDNSL SPEACYECKI NGYPKRGRKR RSTNETDASN IEDQSETEAN VSLASWDVEK  2760
TAIFAFNISH VSNKVRILEL LPALTTLTNH NRYLIESGNE DGFFKINQKE GISYLHFTKK  2820
KPVAGTYSLQ ISSTPLYKKK ELNQLEDKYD KDYLSGELGD NLKMKIQVLL H            2871

SEQ ID NO: 39          moltype = AA  length = 136
FEATURE                Location/Qualifiers
```

```
source                  1..136
                        mol_type = protein
                        organism = Homo sapiens
SEQUENCE: 39
MSNVPHKSSL PEGIRPGTVL RIRGLVPPNA SRFHVNLLCG EEQGSDAALH FNPRLDTSEV  60
VFNSKEQGSW GREERGPGVP FQRGQPFEVL IIASDDGFKA VVGDAQYHHF RHRLPLARVR  120
LVEVGGDVQL DSVRIF                                                 136

SEQ ID NO: 40           moltype = AA  length = 188
FEATURE                 Location/Qualifiers
source                  1..188
                        mol_type = protein
                        organism = Homo sapiens
SEQUENCE: 40
MANSGCKDVT GPDEESFLYF AYGSNLLTER IHLRNPSAAF FCVARLQDFK LDFGNSQGKT  60
SQTWHGGIAT IFQSPGDEVW GVVWKMNKSN LNSLDEQEGV KSGMYVVIEV KVATQEGKEI  120
TCRSYLMTNY ESAPPSPQYK KIICMGAKEN GLPLEYQEKL KAIEPNDYTG KVSEEIEDII  180
KKGETQTL                                                          188

SEQ ID NO: 41           moltype = AA  length = 226
FEATURE                 Location/Qualifiers
source                  1..226
                        mol_type = protein
                        organism = Homo sapiens
SEQUENCE: 41
MARLLQASCL LSLLLAGFVS QSRGQEKSKM DCHGGISGTI YEYGALTIDG EEYIPFKQYA  60
GKYVLFVNVA SYUGLTGQYI ELNALQEELA PFGLVILGFP CNQFGKQEPG ENSEILPTLK  120
YVRPGGGFVP NFQLFEKGDV NGEKEQKFYT FLKNSCPPTS ELLGTSDRLF WEPMKVHDIR  180
WNFEKFLVGP DGIPIMRWHH RTTVSNVKMD ILSYMRRQAA LGVKRK                226

SEQ ID NO: 42           moltype = AA  length = 189
FEATURE                 Location/Qualifiers
source                  1..189
                        mol_type = protein
                        organism = Homo sapiens
SEQUENCE: 42
MALLSRPALT LLLLLMAAVV RCQEQAQTTD WRATLKTIRN GVHKIDTYLN AALDLLGGED  60
GLCQYKCSDG SKPFPRYGYK PSPPNGCGSP LFGVHLNIGI PSLTKCCNQH DRCYETCGKS  120
KNDCDEEFQY CLSKICRDVQ KTLGLTQHVQ ACETTVELLF DSVIHLGCKP YLDSQRAACR  180
CHYEEKTDL                                                         189

SEQ ID NO: 43           moltype = AA  length = 406
FEATURE                 Location/Qualifiers
source                  1..406
                        mol_type = protein
                        organism = Homo sapiens
SEQUENCE: 43
MSALGAVIAL LLWGQLFAVD SGNDVTDIAD DGCPKPPEIA HGYVEHSVRY QCKNYYKLRT  60
EGDGVYTLND KKQWINKAVG DKLPECEADD GCPKPPEIAH GYVEHSVRYQ CKNYYKLRTE  120
GDGVYTLNNE KQWINKAVGD KLPECEAVCG KPKNPANPVQ RILGGHLDAK GSFPWQAKMV  180
SHHNLTTGAT LINEQWLLTT AKNLFLNHSE NATAKDIAPT LTLYVGKKQL VEIEKVVLHP  240
NYSQVDIGLI KLKQKVSVNE RVMPICLPSK DYAEVGRVGY VSGWGRNANF KFTDHLKYVM  300
LPVADQDQCI RHYEGSTVPE KKTPKSPVGV QPILNEHTFC AGMSKYQEDT CYGDAGSAFA  360
VHDLEEDTWY ATGILSFDKS CAVAEYGVYV KVTSIQDWVQ KTIAEN                406

SEQ ID NO: 44           moltype = AA  length = 525
FEATURE                 Location/Qualifiers
source                  1..525
                        mol_type = protein
                        organism = Homo sapiens
SEQUENCE: 44
MKALIAALLL ITLQYSCAVS PTDCSAVEPE AEKALDLINK RRRDGYLFQL LRIADAHLDR  60
VENTTVYYLV LDVQESDCSV LSRKYWNDCE PPDSRRPSEI VIGQCKVIAT RHSHESQDLR  120
VIDFNCTTSS VSSALANTKD SPVLIDFFED TERYRKQANK ALEKYKEEND DFASFRVDRI  180
ERVARVRGGE GTGYFVDFSV RNCPRHHFPR HPNVFGFCRA DLFYDVEALD LESPKNLVIN  240
CEVFDPQEHE NINGVPPHLG HPFHWGGHER SSTTKPPFKP HGSRDHHHPH KPHEHGPPPP  300
PDERDHSHGP PLPQGPPPLL PMSCSSCQHA TFGTNGAQRH SHNNNSSDLH PHKHHSHEQH  360
PHGHHPHAHH PHEHDTHRQH PHGHHPHGHH PHGHHPHGHH PHGHHPHCHD FQDYGPCDPP  420
PHNQGHCCHG HGPPPGHLRR RGPGKGPRPF HCRQIGSVYR LPPLRKGEVL PLPEANFPSF  480
PLPHHKHPLK PDNQPFPQSV SESCPGKFKS GFPQVSMFFT HTFPK                 525

SEQ ID NO: 45           moltype = AA  length = 3972
FEATURE                 Location/Qualifiers
source                  1..3972
                        mol_type = protein
                        organism = Homo sapiens
SEQUENCE: 45
MAHSCRWRFP ARPGTTGGGG GGGRRGLGGA PRQRVPALLL PPGPPVGGGG PGAPPSPPAV  60
AAAAAAAGSS GAGVPGGAAA ASAASSSSAS SSSSSSSSAS SGPALLRVGP GFDAALQVSA  120
```

```
AIGTNLRRFR AVFGESGGGG GSGEDEQFLG FGSDEEVRVR SPTRSPSVKT SPRKPRGRPR  180
SGSDRNSAIL SDPSVFSPLN KSETKSGDKI KKKDSKSIEK KRGRPPTFPG VKIKITHGKD  240
ISELPKGNKE DSLKKIKRTP SATFQQATKI KKLRAGKLSP LKSKFKTGKL QIGRKGVQIV  300
RRRGRPPSTE RIKTPSGLLI NSELEKPQKV RKDKEGTPPL TKEDKTVVRQ SPRRIKPVRI  360
IPSSKRTDAT IAKQLLQRAK KGAQKKIEKE AAQLQGRKVK TQVKNIRQFI MPVVSAISSR  420
IIKTPRRFIE DEDYDPPIKI ARLESTPNSR FSAPSCGSSE KSSAASQHSS QMSSDSSRSS  480
SPSVDTSTDS QASEEIQVLP EERSDTPEVH PPLPISQSPE NESNDRRSRR YSVSERSFGS  540
RTTKKLSTLQ SAPQQQTSSS PPPPLLTPPP PLQPASSISD HTPWLMPPTI PLASPFLPAS  600
TAPMQGKRKS ILREPTFRWT SLKHSRSEPQ YFSSAKYAKE GLIRKPIFDN FRPPPLTPED  660
VGFASGFSAS GTAASARLFS PLHSGTRFDM HKRSPLLRAP RFTPSEAHSR IFESVTLPSN  720
RTSAGTSSSG VSNRKRKRKV FSPIRSEPRS PSHSMRTRSG RLSSSELSPL TPPSSVSSSL  780
SISVSPLATS ALNPTFTFPS HSLTQSGESA EKNQRPRKQT SAPAEPFSSS SPTPLFPWFT  840
PGSQTERGRN KDKAPEELSK DRDADKSVEK DKSRERDRER EKENKRESRK EKRKKGSEIQ  900
SSSALYPVGR VSKEKVVGED VATSSSAKKA TGRKKSSSHD SGTDITSVTL GDTTAVKTKI  960
LIKKGRGNLE KTNLDLGPTA PSLEKEKTLC LSTPSSSTVK HSTSSIGSML AQADKLPMTD  1020
KRVASLLKKA KAQLCKIEKS KSLKQTDQPK AQGQESDSSE TSVRGPRIKH VCRRAAVALG  1080
RKRAVFPDDM PTLSALPWEE REKILSSMGN DDKSSIAGSE DAEPLAPPIK PIKPVTRNKA  1140
PQEPPVKKGR RSRRCGQCPG CQVPEDCGVC TNCLDKPKFG GRNIKKQCCK MRKCQNLQWM  1200
PSKAYLQKQA KAVKKKEKKS KTSEKKDSKE SSVVKNVVDS SQKPTPSARE DPAPKKSSSE  1260
PPPRKPVEEK SEEGNVSAPG PESKQATTPA SRKSSKQVSQ PALVIPPQPP TTGPPRKEVP  1320
KTTPSEPKKK QPPPPESGPE QSKQKKVAPR PSIPVKQKPK EKEKPPPVNK QENAGTLNIL  1380
STLSNGNSSK QKIPADGVHR IRVDFKEDCE AENVWEMGGL GILTSVPITP RVVCFLCASS  1440
GHVEFVYCQV CCEPFHKFCL EENERPLEDQ LENWCCRRCK FCHVCGRQHQ ATKQLLECNK  1500
CRNSYHPECL GPNYPTKPTK KKKVWICTKC VRCKSCGSTT PGKGWDAQWS HDFSLCHDCA  1560
KLFAKGNFCP LCDKCYDDDD YESKMMQCGK CDRWVHSKCE NLSGTEDEMY EILSNLPESV  1620
AYTCVNCTER HPAEWRLALE KELQISLKQV LTALLNSRTT SHLLRYRQAA KPPDLNPETE  1680
ESIPSRSSPE GPDPPVLTEV SKQDDQQPLD LEGVKRKMDQ GNYTSVLEFS DDIVKIIQAA  1740
INSDGGQPEI KKANSMVKSF FIRQMERVFP WFSVKKSRFW EPNKVSSNSG MLPNAVLPPS  1800
LDHNYAQWQE REENSHTEQP PLMKKIIPAP KPKGPGEPDS PTPLHPPTPP ILSTDRSRED  1860
SPELNPPPGI EDNRQCALCL TYGDDSANDA GRLLYIGQNE WTHVNCALWS AEVFEDDDGS  1920
LKNVHMAVIR GKQLRCEFCQ KPGATVGCCL TSCTSNYHFM CSRAKNCVFL DDKKVYCQRH  1980
RDLIKGEVVP ENGFEVFRRV FVDFEGISLR RKFLNGLEPE NIHMMIGSMT IDCLGILNDL  2040
SDCEDKLFPI GYQCSRVYWS TTDARKRCVY TCKIVECRPP VVEPDINSTV EHDENRTIAH  2100
SPTSFTESSS KESQNTAEII SPPSPDRPPH SQTSGSCYYH VISKVPRIRT PSYSPTQRSP  2160
GCRPLPSAGS PTPTTHEIVT VGDPLLSSGL RSIGSRRHST SSLSPQRSKL RIMSPMRTGN  2220
TYSRNNVSSV STTGTATDLE SSAKVVDHVL GPLNSSTSLG QNTSTSSNLQ RTVVTVGNKN  2280
SHLDGSSSSE MKQSSASDLV SKSSSLKGEK TKVLSSKSSE GSAHNVAYPG IPKLAPQVHN  2340
TTSRELNVSK IGSFAEPSSV SFSSKEALSF PHLHLRGQRN DRDQHTDSTQ SANSSPDEDT  2400
EVKTLKLSGM SNRSSIINEH MGSSSRDRRQ KGKKSCKETF KEKHSSKSFL EPGQVTTGEE  2460
GNLKPEFMDE VLTPEYMGQR PCNNVSSDKI GDKGLSMPGV PKAPPMQVEG SAKELQAPRK  2520
RTVKVTLTPL KMENESQSKN ALKESSPASP LQIESTSPTE PISASENPGD GPVAQPSPNN  2580
TSCQDSQSNN YQNLPVQDRN LMLPDGPKPQ EDGSFKRRYP RRSARARSNM FFGLTPLYGV  2640
RSYGEEDIPF YSSSTGKKRG KRSAEGQVDG ADDLSTSDED DLYYYNFTRT VISSGGEERL  2700
ASHNLFREEE QCDLPKISQL DGVDDGTESD TSVTATTRKS SQIPKRNGKE NGTENLKIDR  2760
PEDAGEKEHV TKSSVGHKNE PKMDNCHSVS RVKTQGQDSL EAQLSSLESS RRVHTSTPSD  2820
KNLLDTYNTE LLKSDSDNNN SDDCGNILPS DIMDFVLKNT PSMQALGESP ESSSSELLNL  2880
GEGLGLDSNR EKDMGLFEVF SQQLPTTEPV DSSVSSSISA EEQFELPLEL PSDLSVLTTR  2940
SPTVPSQNPS RLAVISDSGE KRVTITEKSV ASSESDPALL SPGVDPTPEG HMTPDHFIQG  3000
HMDADHISSP PCGSVEQGHG NNQDLTRNSS TPGLQVPVSP TVPIQNQKYV PNSTDSPGPS  3060
QISNAAVQTT PPHLKPATEK LIVVNQNMQP LYVLQTLPNG VTQKIQLTSS VSSTPSVMET  3120
NTSVLGPMGG GLTLTTGLNP SLPTSQSLFP SASKGLLPMS HHQHLHSFPA ATQSSFPPNI  3180
SNPPSGLLIG VQPPPDPQLL VSESSQRTDL STTVATPSSG LKKRPISRLQ TRKNKKLAPS  3240
STPSNIAPSD VVSNMTLINF TPSQLPNHPS LLDLGSLNTS SHRTVPNIIK RSKSSIMYFE  3300
PAPLLPQSVG GTAATAAGTS TISQDTSHLT SGSVSGLASS SSVLNVVSMQ TTTTPTSSAS  3360
VPGHVTLTNP RLLGTPDIGS ISNLLIKASQ QSLGIQDQPV ALPPSSGMFP QLGTSQTPST  3420
AAITAASSIC VLPSTQTTGI TAASPSGEAD EHYQLQHVNQ LLASKTGIHS SQRDLDSASG  3480
PQVSNFTQTV DAPNSMGLEQ NKALSSAVQA SPTSPGGSPS SPSSGQRSAS PSVPGPTKPK  3540
PKTKRFQLPL DKGNGKKHKV SHLRTSSSEA HIPDQETTSL TSGTGTPGAE AEQQDTASVE  3600
QSSQKECGQP AGQVAVLPEV QVTQNPANEQ ESAEPKTVEE EESNFSSPLM LWLQQEQKRK  3660
ESITEKKPKK GLVFEISSDD GFQICAESIE DAWKSLTDKV QEARSNARLK QLSFAGVNGL  3720
RMLGILHDAV VFLIEQLSGA KHCRNYKFRF HKPEEANEPP LNPHGSARAE VHLRKSAFDM  3780
FNFLASKHRQ PPEYNPNDEE EEVQLKSAR RATSMDLPMP MRFRHLKKTS KEAVGVYRSP  3840
IHGRGLFCKR NIDAGEMVIE YAGNVIRSIQ TDKREKYYDS KGIGCYMFRI DDSEVVDATM  3900
HGNAARFINH SCEPNCYSRV ININDGQKHIV IFAMRKIYRG EELTYDYKFP IEDASNKLPC  3960
NCGAKKCRKF LN                                                       3972
```

```
SEQ ID NO: 46           moltype = AA  length = 638
FEATURE                 Location/Qualifiers
source                  1..638
                        mol_type = protein
                        organism = Homo sapiens
SEQUENCE: 46
MILFKQATYF ISLFATVSCG CLTQLYENAF FRGGDVASMY TPNAQYCQMR CTFHPRCLLF  60
SFLPASSIND MEKRFGCFLK DSVTGTLPKV HRTGAVSGHS LKQCGHQISA CHRDIYKGVD  120
MRGVNFNVSK VSSVEECQKR CTSNIRCQFF SYATQTFHKA EYRNNCLLKY SPGGTPTAIK  180
VLSNVESGFS LKPCALSEIG CHMNIFQHLA FSDVDVARVL TPDAFVCRTI CTYHPNCLFF  240
TFYTNVWKIE SQRNVCLLKT SESGTPSSST PQENTISGYS LLTCKRTLPE PCHSKIYPGV  300
DFGGEELNVT FVKGVNVCQE TCTKMIRCQF FTYSLLPEDC KEEKCKCFLR LSMDGSPTRI  360
AYGTQGSSGY SLRLCNTGDN SVCTTKTSTR IVGGTNSSWG EWPWQVSLQV KLTAQRHLCG  420
```

```
GSLIGHQWVL TAAHCFDGLP LQDVWRIYSG ILNLSDITKD TPFSQIKEII IHQNYKVSEG  480
NHDIALIKLQ APLNYTEFQK PICLPSKGDT STIYTNCWVT GWGFSKEKGE IQNILQKVNI  540
PLVTNEECQK RYQDYKITQR MVCAGYKEGG KDACKGDSGG PLVCKHNGMW RLVGITSWGE  600
GCARREQPGV YTKVAEYMDW ILEKTQSSDG KAQMQSPA                        638

SEQ ID NO: 47           moltype = AA  length = 3333
FEATURE                 Location/Qualifiers
source                  1..3333
                        mol_type = protein
                        organism = Homo sapiens
SEQUENCE: 47
MAAAARPRGR ALGPVLPPTP LLLLVLRVLP ACGATARDPG AAAGLSLHPT YFNLAEAARI  60
WATATCGERG PGEGRPQPEL YCKLVGGPTA PGSGHTIQGQ FCDYCNSEDP RKAHPVTNAI  120
DGSERWWQSP PLSSGTQYNR VNLTLDLGQL FHVAYILIKF ANSPRPDLWV LERSVDFGST  180
YSPWQYFAHS KVDCLKEFGR EANMAVTRDD DVLCVTEYSR IVPLENGEVV VSLINGRPGA  240
KNFTFSHTLR EFTKATNIRL RFLRTNTLLG HLISKAQRDP TVTRRYYYSI KDISIGGQCV  300
CNGHAEVCNI NNPEKLFRCE CQHHTCGETC DRCCTGYNQR RWRPAAWEQS HECEACNCHG  360
HASNCYYDPD VERQQASLNT QGIYAGGGVC INCQHNTAGV NCEQCAKGYY RPYGVPVDAP  420
DGCIPCSCDP EHADGCEQGS GRCHCKPNFH GDNCEKCAIG YYNFPFCLRI PIFPVSTPSS  480
EDPVAGDIKG CDCNLEGVLP EICDAHGRCL CRPGVEGPRC DTCRSGFYSF PICQACWCSA  540
LGSYQMPCSS VTGQCECRPG VTGQRCDRCL SGAYDFPHCQ GSSSACDPAG TINSNLGYCQ  600
CKLHVEGPTC SRCKLLYWNL DKENPSGCSE CKCHKAGTVS GTGECRQGDG DCHCKSHVGG  660
DSCDTCEDGY FALEKSNYFG CQGCQCDIGG ALSSMCSGPS GVCQCREHVV GKVCQRPENN  720
YYFPDLHHMK YEIEDGSTPN GRDLRPGFDP LAFPEFSWRG YAQMTSVQND VRITLNVGKS  780
SGSLFRVILR YVNPGTEAVS GHITIYPSWG AAQSKEIIFL PSKEPAFVTV PGNGFADPFS  840
ITPGIWVACI KAEGVLLDYL VLLPRDYYEA SVLQLPVTEP CAYAGPPQEN CLLYQHLPVT  900
RFPCTLACEA RHFLLDGEPR PVAVRQPTPA HPVMVDLSGR EVELHLRLRI PQVGHYVVVV  960
EYSTEAAQLF VVDVNVKSSG SVLAGQVNIY SCNYSVLCRS AVIDHMSRIA MYELLADADI  1020
QLKGHMARFL LHQVCIIPIE EFSAEYVRPQ VHCIASYGRF VNQSATCVSL AHETPPTALI  1080
LDVLSGRPFP HLPQQSSPSV DVLPGVTLKA PQNQVTLRGR VPHLGRYVFV IHFYQAAHPT  1140
FPAQVSVDGG WPRAGSFHAS FCPHVLGCRD QVIAEGQIEF DISEPEVAAT VKVPEGKSLV  1200
LVRVLVVPAE NYDYQILHKK SMDKSLEFIT NCGKNSFYLD PQTASRFCKN SARSLVAFYH  1260
KGALPCECHP TGATGPHCSP EGGQCPCQPN VIGRQCTRCA TGHYGFPRCK PCSCGRRLCE  1320
EMTGQCRCPP RTVRPQCEVC ETHSFSFHPM AGCEGCNCSR RGTIEAAMPE CDRDSGQCRC  1380
KPRITGRQCD RCASGFYRFP ECVPCNCNRD GTEPGVCDPG TGACLCKENV EGTECNVCRE  1440
GSFHLDPANL KGCTSCFCFG VNNQCHSSHK RRTKFVDMLG WHLETADRVD IPVSFNPGSN  1500
SMVADLQELP ATIHSASWVA PTSYLGDKVS SYGGYLTYQA KSFGLPGDMV LLEKKPDVQL  1560
TGQHMSIIYE ETNTPRPDRL HHGRVHVVEG NFRHASSRAP VSREELMTVL SRLADVRIQG  1620
LYFTETQRLT LSEVGLEEAS DTGSGRIALA VEICACPPAY AGDSCQGCSP GYYRDHKGLY  1680
TGRCVPCNCN GHSNQCQDGS GICVNCQHNT AGEHCERCQE GYYGNAVHGS CRACPCPHTN  1740
SFATGCVVNG GDVRCSCKAG YTGTQCERCA PGYFGNPQKF GGSCQPCSCN SNGQLGSCHP  1800
LTGDCINQEP KDSSPAEECD DCDSCVMTLL NDLATMGEQL RLVKSQLQGL SASAGLLEQM  1860
RHMETQAKDL RNQLLNYRSA ISNHGSKIEG LERELTDLNQ EFETLQEKAQ VNSRKAQTLN  1920
NNVNRATQSA KELDVKIKNV IRNVHILLKQ ISGTDGEGNN VPSGDFSREW AEAQRMMREL  1980
RNRNFGKHLR EAEADKRESQ LLLNRIRTWQ KTHQGENNGL ANSIRDSLNE YEAKLSDLRA  2040
RLQEAAAQAK QANGLNQENE RALGAIQRQV KEINSLQSDF TKYLTTADSS LLQTNIALQL  2100
MEKSQKEYEK LAASLNEARQ ELSDKVRELS RSAGKTSLVE EAEKHARSLQ ELAKQLEEIK  2160
RNASGDELVR CAVDAATAYE NILNAIKAAE DAANRAASAS ESALQTVIKE DLPRKAKTLS  2220
SNSDKLLNEA KMTQKKLKQE VSPALNNLQQ TLNIVTVQKE VIDTNLTTLR DGLHGIQRGD  2280
IDAMISSAKS MVRKANDITD EVLDGLNPIQ TDVERIKDTY GRTQNEDFKK ALTDADNSVN  2340
KLTNKLPDLW RKIESINQQL LPLGNISDNM DRIRELIQQA RDAASKVAVP MRFNGKSGVE  2400
VRLPNDLEDL KGYTSLSLFL QRPNSRENGG TENMFVMYLG NKDASRDYIG MAVVDGQLTC  2460
VYNLGDREAE LQVDQILTKS ETKEAVMDRV KFQRIYQFAR LNYTKGATSS KPETPGVYDM  2520
DGRNSNTLLN LDPENVVFYV GGYPPDFKLP SRLSFPPYKG CIELDDLNEN VLSLYNFKKT  2580
FNLNTTEVEP CRRRKEESDK NYFEGTGYAR VPTQPHAPIP TFGQTIQTTV DRGLLFFAEN  2640
GDRFISLNIE DGKLMVRYKL NSELPKERGV GDAINNGRDH SIQIKIGKLQ KRMWINVDVQ  2700
NTIIDGEVFD FSTYYLGGIP IAIRERFNIS TPAFRGCMKN LKKTSGVVRL NDTVGVTKKC  2760
SEDWKLVRSA SFSRGGQLSF TDLGLPPTDH LQASFGFQTF QPSGILLDHQ TWTRNLQVTL  2820
EDGYIELSTS DSGGPIFKSP QTYMDGLLHY VSVISDNSGL RLLIDDQLLR NSKRLKHISS  2880
SRQSLRLGGS NFEGCISNVF VQRLSLSPEV LDLTSNSLKR DVSLGGCSLN KPPFLMLLKG  2940
STRFNKTKTF RINQLLQDTP VASPRSVKVW QDACSPLPKT QANHGALQFG DIPTSHLLFK  3000
LPQELLKPRS QFAVDMQTTS SRGLVFHTGT KNSFMALYLS KGRLVFALGT DGKKLRIKSK  3060
EKCNDGKWHT VVFGHDGEKG RLVVDGLRAR EGSLPGNSTI SIRAPVYLGS PPSGKPKSLP  3120
TNSFVGCLKN FQLDSKPLYT PSSSFGVSSC LGGPLEKGIY FSEEGGHVVL AHSVLLGPEF  3180
KLVFSIRPRS LTGILIHIGS QPGKHLCVYL EAGKVTASMD SGAGGTSTSV TPKQSLCDGQ  3240
WHSVAVTIKQ HILHLELDTD SSYTAGQIPF PPASTQEPLH LGGAPANLTT LRIPVWKSFF  3300
GCLRNIHVNH IPVPVTEALE VQGPVSLNGC PDQ                              3333

SEQ ID NO: 48           moltype = AA  length = 347
FEATURE                 Location/Qualifiers
source                  1..347
                        mol_type = protein
                        organism = Homo sapiens
SEQUENCE: 48
MSSWSRQRPK SPGGIQPHVS RTLFLLLLLA ASAWGVTLSP KDCQVFRSDH GSSISCQPPA  60
EIPGYLPADT VHLAVEFFNL THLPANLLQG ASKLQELHLS SNGLESLSPE FLRPVPQLRV  120
LDLTRNALTG LPPGLFQASA TLDTLVLKEN QLEVLEVSWL HGLKALGHLD LSGNRLRKLP  180
PGLLANFTLL RTLDLGENQL ETLPPDLLRG PLQLERLHLE GNKLQVLGKD LLLPQPDLRY  240
LFLNGNKLAR VAAGAFQGLR QLDMLDLSNN SLASVPEGLW ASLGQPNWDM RDGFDISGNP  300
```

```
WICDQNLSDL YRWLQAQKDK MFSQNDTRCA GPEAVKGQTL LAVAKSQ             347

SEQ ID NO: 49          moltype = AA  length = 4655
FEATURE                Location/Qualifiers
source                 1..4655
                       mol_type = protein
                       organism = Homo sapiens
SEQUENCE: 49
MDRGPAAVAC TLLLALVACL APASGQECDS AHFRCGSGHC IPADWRCDGT KDCSDDADEI  60
GCAVVTCQQG YFKCQSEGQC IPNSWVCDQD QDCDDGSDER QDCSQSTCSS HQITCSNGQC  120
IPSEYRCDHV RDCPDGADEN DCQYPTCEQL TCDNGACYNT SQKCDWKVDC RDSSDEINCT  180
EICLHNEFSC GNGECIPRAY VCDHDNDCQD GSDEHACNYP TCGGYQFTCP SGRCIYQNWV  240
CDGEDDCKDN GDEDGCESGP HDVHKCSPRE WSCPESGRCI SIYKVCDGIL DCPGREDENN  300
TSTGKYCSMT LCSALNCQYQ CHETPYGGAC FCPPGYIINH NDSRTCVEFD DCQIWGICDQ  360
KCESRPGRHL CHCEEGYILE RGQYCKANDS FGEASIIFSN GRDLLIGDIH GRSFRILVES  420
QNRGVAVGVA FHYHLQRVFW TDTVQNKVFS VDINGLNIQE VLNVSVETPE NLAVDWVNNK  480
IYLVETKVNR IDMVNLDGSY RVTLITENLG HPRGIAVDPT VGYLFFSDWE SLSGEPKLER  540
AFMDGSNRKD LVKTKLGWPA GVTLDMISKR VYWVDSRFDY IETVTYDGIQ RKTVVHGGSL  600
IPHPFGVSLF EGQVFFTDWT KMAVLKANKF TETNPQVYYQ ASLRPYGVTV YHSLRQPYAT  660
NPCKDNNGGC EQVCVLSHRT DNDGLGFRCK CTFGFQLDTD ERHCIAVQNF LIFSSQVAIR  720
GIPFTLSTQE DVMVPVSGNP SFFVGIDFDA QDSTIFFSDM SKHMIFKQKI DGTGREILAA  780
NRVENVESLA FDWISKNLYW TDSHYKSISV MRLADKTRRT VVQYLNNPRS VVVHPFAGYL  840
FFTDWFRPAK IMRAWSDGSH LLPVINTTLG WPNGLAIDWA ASRLYWVDAY FDKIEHSTFD  900
GLDRRRLGHI EQMTHPFGLA IFGEHLFFTD WRLGAIIRVR KADGGEMTVI RSGIAYILHL  960
KSYDVNIQTG SNACNQPTHP NGDCSHFCFP VPNFQRVCGC PYGMRLASNH LTCEGDPTNE  1020
PPTEQCGLFS FPCKNGRCVP NYYLCDGVDD CHDNSDEQLC GTLNNTCSSS AFTCGHGECI  1080
PAHWRCDKRN DCVDGSDEHN CPTHAPASCL DTQYTCDNHQ CISKNWVCDT DNDCGDGSDE  1140
KNCNSTETCQ PSQFNCPNHR CIDLSFVCDG DKDCVDGSDE VGCVLNCTAS QFKCASGDKC  1200
IGVTNRCDGV FDCSDNSDEA GCPTRPPGMC HSDEFQCQED GICIPNFWEC DGHPDCLYGS  1260
DEHNACVPKT CPSSYFHCDN GNCIHRAWLC DRDNDCGDMS DEKDCPTQPF RCPSWQWQCL  1320
GHNICVNLSV VCDGIFDCPN GTDESPLCNG NSCSDFNGGC THECVQEPFG AKCLCPLGFL  1380
LANDSKTCED IDECDILGSC SQHCYNMRGS FRCSCDTGYM LESDGRTCKV TASESLLLLV  1440
ASQNKIIADS VTSQVHNIYS LVENGSYIVA VDFDSISGRI FWSDATQGKT WSAFQNGTDR  1500
RVVFDSSIIL TETIAIDWVG RNLYWTDYAL ETIEVSKIDG SHRTVLISKN LTNPRGLALD  1560
PRMNEHLLFW SDWGHHPRIE RASMDGSMRT VIVQDKIFWP CGLTIDYPNR LLYFMDSYLD  1620
YMDFCDYNGH HRRQVIASDL IIRHPYALTL FEDSVYWTDR ATRRVMRANK WHGGNQSVVM  1680
YNIQWPLGIV AVHPSKQPNS VNPCAFSRCS HLCLLSSQGP HFYSCVCPSG WSLSPDLLNC  1740
LRDDQPFLIT VRQHIIFGIS LNPEVKSNDA MVPIAGIQNG LDVEFDDAEQ YIYWVENPGE  1800
IHRVKTDGTN RTVFASISMV GPSMNLALDW ISRNLYSTNP RTQSIEVLTL HGDIRYRKTL  1860
IANDGTALGV GFPIGITVDP ARGKLYWSDQ GTDSGVPAKI ASANMDGTSV KTLFTGNLEH  1920
LECVTLDIEE QKLYWAVTGR GVIERGNVDG TDRMILVHQL SHPWGIAVHD SFLYYTDEQY  1980
EVIERVDKAT GANKIVLRDN VPNLRGLQVY HRRNAAESSN GCSNNMNACQ QICLPVPGGL  2040
FSCACATGFK LNPDNRSCSP YNSFIVVSML SAIRGFSLEL SDHSETMVPV AGQGRNALHV  2100
DVDVSSGFIY WCDFSSSVAS DNAIRRIKPD GSSLMNIVTH GIGENGVRGI AVDWVAGNLY  2160
FTNAFVSETL IEVLRINTTY RRVLLKVTVD MPRHIVVDPK NRYLFWADYG QRPKIERSFL  2220
DCTNRTVLVS EGIVTPRGLA VDRSDGYVYW VDDSLDIIAR IRINGENSEV IRYGSRYPTP  2280
YGITVFENSI IWVDRNLKKI FQASKEPENT EPPTVIRDNI NWLRDVTIFD KQVQPRSPAE  2340
VNNNPCLENN GGCSHLCFAL PGLHTPKCDC AFGTLQSDGK NCAISTENFL IFALSNSLRS  2400
LHLDPENHSP PFQTINVERT VMSLDYDSVS DRIYFTQNLA SGVGQISYAT LSSGIHTPTV  2460
IASGIGTADG IAFDWITRRI YYSDYLNQMI NSMAEDGSNR TVIARVPKPR AIVLDPCQGY  2520
LYWADWDTHA KIERATLGGN FRVPIVNSSL VMPSGLTLDY EEDLLYWVDA SLQRIERSTL  2580
TGVDREVIVN AAVHAFGLTL YGQYIYWTDL YTQRIYRANK YDGSGQIAMT TNLLSQPRGI  2640
NTVVKNQKQQ CNNPCEQFNG GCSHICAPGP NGAECQCPHE GNWYLANNRK HCIVDNGERC  2700
GASSFTCSNG RCISEEWKCD NDNDCGDGSD EMESVCALHT CSPTAFTCAN GRCVQYSYRC  2760
DYYNDCGDGS DEAGCLFRDC NATTEFMCNN RRCIPREFIC NGVDNCHDNN TSDEKNCPDR  2820
TCQSGYTKCH NSNICIPRVY LCDGDNDCGD NSDENPTYCT THTCSSSEFQ CASGRCIPQH  2880
WYCDQETDCF DASDEPASCG HSERTCLADE FKCDGGRCIP SEWICDGDND CGDMSDEDKR  2940
HQCQNQNCSD SEFLCVNDRP PDRRCIPQSW VCDGDVDCTD GYDENQNCTR RTCSENEFTC  3000
GYGLCIPKIF RCDRHNDCGD YSDERGCLYQ TCQQNQFTCQ NGRCISKTFV CDEDNDCGDG  3060
SDELMHLCHT PEPTCPPHEF KCDNGRCIEM MKLCNHLDDC LDNSDEKGCG INECHDPSIS  3120
GCDHNCTDTL TSFYCSCRPG YKLMSDKRTC VDIDECTEMP FVCSQKCENV IGSYICKCAP  3180
GYLREPDGKT CRQNSNIEPY LIFSNRYYLR NLTIDGYFYS LILEGLDNVV ALDFDRVEKR  3240
LYWIDTQRQV IERMFLNKTN KETIINHRLP AAESLAVDWV SRKLYWLDAR LDGLFVSDLN  3300
GGHRRMLAQH CVDANNTFCF DNPRGLALHP QYGYLYWADW GHRAYIGRVG MDGTNKSVII  3360
STKLEWPNGI TIDYTNDLLY WADAHLGYIE YSDLEGHHRH TVYDGALPHP FAITIFEDTI  3420
YWTDWNTRTV EKGNKYDGSN RQTLVNTTHR PFDIHVYHPY RQPIVSNPCG TNNGGCSHLC  3480
LIKPGGKGFT CECPDDFRTL QLSGSTYCMP MCSSTQFLCA NNEKCIPIWW KCDGQKDCSD  3540
GSDELALCPQ RFCRLGQFQC SDGNCTSPQT LCNAHQNCPD GSDEDRLLCE NHHCDSNEWQ  3600
CANKRCIPES WQCDTFNDCE DNSDEDSSHC ASRTCRPGQF RCANGRCIPQ AWKCDVDNDC  3660
GDHSDEPIEE CMSSAHLCDN FTEFSCKTNY RCIPKWAVCN GVDDCRDNSD EQGCEERTCH  3720
PVGDFRCKNH HCIPLRWQCD GQNDCGDNSD EENCAPRECT ESEFRCVNQQ CIPSRWICDH  3780
YNDCGDNSDE RDCEMRTCHP EYFQCTSGHC VHSELKCDGS ADCLDASDEA DCPTRFPDGA  3840
YCQATMFECK NHVCIPPYWK CDGDDDCGDG SDEELHLCLD VPCNSPNRFR CDNNRCIYSH  3900
EVCNGVDDCG DGTDETEEHC RKPTPKPCTE YEYKCGNGHC IPHDNVCDDA DDCGDWSDEL  3960
GCNKGKERTC AENICEQNCT QLNEGGFICS CTAGFETNVF DRTSCLDINE CEQFGTCPQH  4020
CRNTKGSYEC VCADGFTSMS DRPGKRCAAE GSSPLLLLPD NVRIRKYNLS SERFSEYLQD  4080
EEYIQAVDYD WDPKDIGLSV VYYTVRGEGS RFGAIKRAYI PNFESGRNNL VQEVDLKLKY  4140
VMQPDGIAVD WVGRHIYWSD VKNKRIEVAK LDGRYRKWLI STDLDQPAAI AVNPKLGLMF  4200
WTDWGKEPKI ESAWMNGEDR NILVFEDLGW PTGLSIDYLN NDRIYWSDFK EDVIETIKYD  4260
```

```
GTDRRVIAKE AMNPYSLDIF EDQLYWISKE KGEVWKQNKF GQGKKEKTLV VNPWLTQVRI  4320
FHQLRYNKSV PNLCKQICSH LCLLRPGGYS CACPQGSSFI EGSTTECDAA IELPINLPPP  4380
CRCMHGGNCY FDETDLPKCK CPSGYTGKYC EMAFSKGISP GTTAVAVLLT ILLIVVIGAL  4440
AIAGFFHYRR TGSLLPALPK LPSLSSLVKP SENGNGVTFR SGADLNMDIG VSGFGPETAI  4500
DRSMAMSEDF VMEMGKQPII FENPMYSARD SAVKVVQPIQ VTVSENVDNK NYGSPINPSE  4560
IVPETNPTSP AADGTQVTKW NLFKRKSKQT TNFENPIYAQ MENEQKESVA ATPPPSPSLP  4620
AKPKPPSRRD PTPTYSATED TFKDTANLVK EDSEV                            4655

SEQ ID NO: 50           moltype = AA  length = 61
FEATURE                 Location/Qualifiers
source                  1..61
                        mol_type = protein
                        organism = Homo sapiens
SEQUENCE: 50
MDPNCSCSPV GSCACAGSCK CKECKCTSCK KSCCSCCPVG CAKCAQGCIC KGTSDKCSCC  60
A                                                                 61

SEQ ID NO: 51           moltype = AA  length = 1140
FEATURE                 Location/Qualifiers
source                  1..1140
                        mol_type = protein
                        organism = Homo sapiens
SEQUENCE: 51
MVISLNSCLS FICLLLCHWI GTASPLNLED PNVCSHWESY SVTVQESYPH PFDQIYYTSC  60
TDILNWFKCT RHRVSYRTAY RHGEKTMYRR KSQCCPGFYE SGEMCVPHCA DKCVHGRCIA  120
PNTCQCEPGW GGTNCSSACD GDHWGPHCTS RCQCKNGALC NPITGACHCA AGFRGWRCED  180
RCEQGTYGND CHQRCQCQNG ATCDHVTGEC RCPPGYTGAF CEDLCPPGKH GPQCEQRCPC  240
QNGGVCHHVT GECSCPSGWM GTVCGQPCPE GRFGKNCSQE CQCHNGGTCD AATGQCHCSP  300
GYTGERCQDE CPVGTYGVLC AETCQCVNGG KCYHVSGACL CEAGFAGERC EARLCPEGLY  360
GIKCDKRCPC HLENTHSCHP MSGECACKPG WSGLYCNETC SPGFYGEACQ QICSCQNGAD  420
CDSVTGKCTC APGFKGIDCS TPCPLGTYGI NCSSRCGCKN DAVCSPVDGS CTCKAGWHGV  480
DCSIRCPSGT WGFGCNLTCQ CLNGGACNTL DGTCTCAPGW RGEKCELPCQ DGTYGLNCAE  540
RCDCSHADGC HPTTGHCRCL PGWSGVHCDS VCAEGRWGPN CSLPCYCKNG ASCSPDDGIC  600
ECAPGFRGTT CQRICSPGFY GHRCSQTCPQ CVHSSGPCHH ITGLCDCLPG FTGALCNEVC  660
PSGRFGKNCA GICTCTNNGT CNPIDRSCQC YPGWIGSDCS QPCPPAHWGP NCIHTCNCHN  720
GAFCSAYDGE CKCTPGWTGL YCTQRCPLGF YGKDCALICQ CQNGADCDHI SGQCTCRTGF  780
MGRHCEQKCP SGTYGYGCRQ ICDCLNNSTC DHITGTCYCS PGWKGARCDQ AGVIIVGNLN  840
SLSRTSTALP ADSYQIGAIA GIIILVLVVL FLLALFIIYR HKQKGKESSM PAVTYTPAMR  900
VVNADYTISG TLPHSNGGNA NSHYFTNPSY HTLTQCATSP HVNNRDRMTV TKSKNNQLFV  960
NLKNVNPGKR GPVGDCTGTL PADWKHGGYL NELGAFGLDR SYMGKSLKDL GKNSEYNSSN  1020
CSLSSSENPY ATIKDPPVLI PKSSECGYVE MKSPARRDSP YAEINNSTSA NRNVYEVEPT  1080
VSVVQGVFSN NGRLSQDPYD LPKNSHIPCH YDLLPVRDSS SSPKQEDSGG SSSNSSSSSE  1140

SEQ ID NO: 52           moltype = AA  length = 2385
FEATURE                 Location/Qualifiers
source                  1..2385
                        mol_type = protein
                        organism = Homo sapiens
SEQUENCE: 52
MPVLGVASKL RQPAVGSKPV HTALPIPNLG TTGSQHCSSR PLELTETESS MLSCQLALKS  60
TCEFGEKKPL QGKAKEKEDS KIYTDWANHY LAKSGHKRLI KDLQQDIADG VLLAEIIQII  120
ANEKVEDING CPRSQSQMIE NVDVCLSFLA ARGVNVQGLS AEEIRNGNLK AILGLFFSLS  180
RYKQQQHHQQ QYYQSLVELQ QRVTHASPPS EASQAKTQQD MQSSLAARYA TQSNHSGIAT  240
SQKKPTRLPG PSRVPAAGSS SKVQGASNLN RRSQSFNSID KNKPPNYANG NEKDSSKGPQ  300
SSSGVNGNVQ PPSTAGQPPA SAIPSPSASK PWRSKSMNVK HSATSTMLTV KQSSTATSPT  360
PSSDRLKPPV SEGVKTAPSG QKSMLEKFKL VNARTALRPP QPPSSGPSDG GKDDDAFSES  420
GEMEGFNSGL NSGGSTNSSP KVSPKLAPPK AGSKNLSNKK SLLQPKEKEE KNRDKNKVCT  480
EKPVKEEKDQ VTEMAPKKTS KIASLIPKGS KTTAAKKESL IPSSSGIPKP GSKVPTVKQT  540
ISPGSTASKE SEKFRTTKGS PSQSLSKPIT MEKASASSCP APLEGREAGQ ASPSGSCTMT  600
VAQSSGQSTG NGAVQLPQQQ QHSHPNTATV APFIYRAHSE NEGTALPSAD SCTSPTKMDL  660
SYSKTAKQCL EEISGEDPET RRMRTVKNIA DLRQNLEETM SSLRGTQISH STLETTFDST  720
VTTEVNGRTI PNLTSRPTPM TWRLGQACPR LQAGDAPSLG AGYPRSGTSR FIHTDPSRFM  780
YTTPLRRAAV SRLGNMSQID MSEKASSDLD MSSEVDVGGY MSDGDILGKS LRTDDINSGY  840
MTDGGLNLYT RSLNRIPDTA TSRDIIQRGV HDVTVDADSW DDSSSVSSGL SDTLDNISTD  900
DLNTTSSVSS YSNITVPSRK NTQLRTDSEK RSTTDETWDS PEELKKPEED FDSHGDAGGK  960
WKTVSSGLPE DPEKAGQKAS LSVSQTGSWR RGMSAQGGAP SRQKAGTSAL KTPGKTDDAK  1020
ASEKGKAPLK GSSLQRSPSD AGKSSGDEGK KPPSGIGRST ATSSFGFKKP SGVGSSAMIT  1080
SSGATITSGS ATLGKIPKSA AIGGKSNAGR KTSLDGSQNQ DDVVLHVSSK TTLQYRSLPR  1140
PSKSSTSGIP GRGGHRSSTS SIDSNVSSKS AGATTSKLRE PTKIGSGRSS PVTVNQTDKE  1200
KEKVAVSDSE SVSLSGSPKS SPTSASACGA QGLRQPGSKY PDIASPTFRR LFGAKAGGKS  1260
ASAPNTEGVK SSSVMPSPST TLARQGSLES PSSGTGSMGS AGGLSGSSSP LFNKPSDLTT  1320
DVISLSHSLA SSPASVHSFT SGGLVWAANM SSSSAGSKDT PSYQSMTSLH TSSESIDLPL  1380
SHHGSLSGLT TGTHEVQSLL MRTGSVRSTL SESMQLDRNT LPKKGLRYTP SSRQANQEEG  1440
KEWLRSHSTG GLQDTGNQSP LVSPSAMSSS AAGKYHFSNL VSPTNLSQFN LPGPSMMRSN  1500
SIPAQDSSFD LYDDSQLCGS ATSLEERPRA ISHSGSFRDS MEEVHGSSLS LVSSTSSLYS  1560
TAEEKAHSEQ IHKLRRELVA SQEKVATLTS QLSANAHLVA AFEKSLGNMT GRLQSLTMTA  1620
EQKESELIEL RETIEMLKAQ NSAAQAAIQG ALNGPDHPPK DLRIRRQHSS ESVSSINSAT  1680
SHSSIGSGND ADSKKKKKKN WVNSRGSELR SSFKQAFGKK KSTKPPSSHS DIEELTDSSL  1740
PASPKLPHNA GDCGSASMKP SQSASASPLV WPPKKRQNGP VIYKHRSRIC ECTEAEAEII  1800
```

```
LQLKSELREK ELKLTDIRLE ALSSAHHLDQ IREAMNRMQN EIEILKAEND RLKAETGNTA  1860
KPTRPPSESS SSTSSSSSRQ SLGLSLNNLN ITEAVSSDIL LDDAGDATGH KDGRSVKIIV  1920
SISKGYGRAK DQKSQAYLIG SIGVSGKTKW DVLDGVIRRL FKEYVFRIDT STSLGLSSDC  1980
IASYCIGDLI RSHNLEVPEL LPCGYLVGDN NIITVNLKGV EENSLDSFVF DTLIPKPITQ  2040
RYFNLLMEHH RIILSGPSGT GKTYLANKLA EYVITKSGRK KTEDAIATFN VDHKSSKELQ  2100
QYLANLAEQC SADNNGVELP VVIILDNLHH VGSLSDIFNG FLNCKYNKCP YIIGTMNQGV  2160
SSSPNLELHH NFRWVLCANH TEPVKGFLGR YLRRKLIEIE IERNIRNNDL VKIIDWIPKT  2220
WHHLNSFLET HSSSDVTIGP RLFLPCPMDV EGSRVWFMDL WNYSLVPYIL EAVREGLQMY  2280
GKRTPWEDPS KWVLDTYPWS SATLPQESPA LLQLRPEDVG YESCTSTKEA TTSKHIPQTD  2340
TEGDPLMNML MKLQEAANYS STQSCDSEST SHHEDILDSS LESTL                 2385

SEQ ID NO: 53          moltype = AA  length = 576
FEATURE                Location/Qualifiers
source                 1..576
                       mol_type = protein
                       organism = Homo sapiens
SEQUENCE: 53
MAQGVLWILL GLLLWSDPGT ASLPLLMDSV IQALAELEQK VPAAKTRHTA SAWLMSAPNS  60
GPHNRLYHFL LGAWSLNATE LDPCPLSPEL LGLTKEVARH DVREGKEYGV VLAPDGSTVA  120
VEPLLAGLEA GLQGRRVINL PLDSMAAPWE TGDTFPDVVA IAPDVRATSS PGLRDGSPDV  180
TTADIGANTP DATKGCPDVQ ASLPDAKAKS PPTMVDSLLA VTLAGNLGLT FLRGSQTQSH  240
PDLGTEGCWD QLSAPRTFTL LDPKASLLTM AFLNGALDGV ILGDYLSRTP EPRPSLSHLL  300
SQYYGAGVAR DPGFRSNFRR QNGAALTSAS ILAQQVWGTL VLLQRLEPVH LQLQCMSQEQ  360
LAQVAANATK EFTEAFLGCP AIHPRCRWGA APYRGRPKLL QLPLGFLYVH HTYVPAPPCT  420
DFTRCAANMR SMQRYHQDTQ GWGDIGYSFV VGSDGYVYEG RGWHWVGAHT LGHNSRGFGV  480
AIVGNYTAAL PTEAALRTVR DTLPSCAVRA GLLRPDYALL GHRQLVRTDC PGDALFDLLR  540
TWPHFTATVK PRPARSVSKR SRREPPPRTL PATDLQ                           576

SEQ ID NO: 54          moltype = AA  length = 913
FEATURE                Location/Qualifiers
source                 1..913
                       mol_type = protein
                       organism = Homo sapiens
SEQUENCE: 54
MGWGSRCCCP GRLDLLCVLA LLGGCLLPVC RTRVYTNHWA VKIAGGFPEA NRIASKYGFI  60
NIGQIGALKD YYHFYHSRTI KRSVISSRGT HSFISMEPKV EWIQQQVVKK RTKRDYDFSR  120
AQSTYFNDPK WPSMWYMHCS DNTHPCQSDM NIEGAWKRGY TGKNIVVTIL DDGIERTHPD  180
LMQNYDALAS CDVNGNDLDP MPRYDASNEN KHGTRCAGEV AAAANNSHCT VGIAFNAKIG  240
GVRMLDGDVT DMVEAKSVSF NPQHVHIYSA SWGPDDDGKT VDGPAPLTRQ AFENGVRMGR  300
RGLGSVFVWA SGNGGRSKDH CSCDGYTNSI YTISISSTAE SGKKPWYLEE CSSTLATTYS  360
SGESYDKKII TTDLRQRCTD NHTGTSASAP MAAGIIALAL EANPFLTWRD VQHVIVRTSR  420
AGHLNANDWK TNAAGFKVSH LYGFGLMDAE AMVMEAEKWT TVPRQHVCVE STDRQIKTIR  480
PNSAVRSIYK ASGCSDNPNR HVNYLEHVVV RITITHPRRG DLAIYLTSPS GTRSQLLANR  540
LFDHSMEGFK NWEFMTIHCW GERAAGDWVL EVYDTPSQLR NFKTPGKLKE WSLVLYGTSV  600
QPYSPTNEFP KVERFRYSRV EDPTDDYGTE DYAGPCDPEC SEVGCDGPGP DHCNDCLHYY  660
YKLKNNTRIC VSSCPPGHYH ADKKRCRKCA PNCESCFGSH GDQCMSCKYG YFLNEETNSC  720
VTHCPDGSYQ DTKKNLCRKC SENCKTCTEF HNCTECRDGL SLQGSRCSVS CEDGRYFNGQ  780
DCQPCHRFCA TCAGAGADGC INCTEGYFME DGRCVQSCSI SYYFDHSSEN GYKSCKKCDI  840
SCLTCNGPGF KNCTSCPSGY LLDLGMCQMG AICKDATEES WAEGGFCMLV KKNNLCQRKV  900
LQQLCCKTCT FQG                                                    913

SEQ ID NO: 55          moltype = AA  length = 908
FEATURE                Location/Qualifiers
source                 1..908
                       mol_type = protein
                       organism = Homo sapiens
SEQUENCE: 55
MKSSVAQIKP SSGHDRRENL NSYQRNSSPE DRYEEQERSP RDRDYFDYSR SDYEHSRRGR  60
SYDSSMESRN RDREKRRERE RDTDRKRSRK SPSPGRRNPE TSVTQSSSAQ DEPATKKKKD  120
ELDPLLTRTG GAYIPPAKLR MMQEQITDKN SLAYQRMSWE ALKKSINGLI NKVNISNISI  180
IIQELLQENI VRGRGLLSRS VLQAQSASPI FTHVYAALVA IINSKFPQIG ELILKRLILN  240
FRKGYRRNDK QLCLTASKFV AHLINQNVAH EVLCLEMLTL LLERPTDDSV EVAIGFLKEC  300
GLKLTQVSPR GINAIFERLR NILHESEIDK RVQYMIEVMF AVRKDGFKDH PIILEGLDLV  360
EEDDQFTHML PLEDDYNPED VLNVFKMDPN FMENEEKYKA IKKEILDEGD TDSNTDQDAG  420
SSEEDEEEEE EEGEEDEEGQ KVTIHDKTEI NLVSFRRTIY LAIQSSLDFE ECAHKLLKME  480
FPESQTKELC NMILDCCAQQ RTYEKFFGLL AGRFCMLKKE YMESFEGIFK EQYDTIHRLE  540
TNKLRNVAKM FAHLLYTDSL PWSVLECIKL SEETTTSSSR IFVKIFFQEL CEYMGLPKLN  600
ARLKDETLQP FFEGLLPRDN PRNTRFAINF FTSIGLGGLT DELREHLKNT PKVIVAQKPD  660
VEQNKSSPSS SSSASSSES DSSDSDSDSS DSSSESSSEE SDSSSISSHS SASANDVRKK  720
GHGKTRSKEV DKLIRNQQTN DRKQKERRQE HGHQETRTER ERRSEKHRDQ NSSGSNWRDP  780
ITKYTSDKDV PSERNNYSRV ANDRDQEMHI DLENKHGDPK KKRGERRNSF SENEKHTHRI  840
KDSENFRRKD RSKSKEMNRK HSGSRSDEDR YQNGAERRWE KSSRYSEQSR ESKKNQDRRR  900
EKSPAKQK                                                          908

SEQ ID NO: 56          moltype = AA  length = 105
FEATURE                Location/Qualifiers
source                 1..105
                       mol_type = protein
                       organism = Homo sapiens
```

```
SEQUENCE: 56
MAKISSPTET ERCIESLIAV FQKYAGKDGY NYTLSKTEFL SFMNTELAAF TKNQKDPGVL  60
DRMMKKLDTN SDGQLDFSEF LNLIGGLAMA CHDSFLKAVP SQKRT                 105

SEQ ID NO: 57          moltype = AA  length = 101
FEATURE                Location/Qualifiers
source                 1..101
                       mol_type = protein
                       organism = Homo sapiens
SEQUENCE: 57
MSNTQAERSI IGMIDMFHKY TRRDDKIEKP SLLTMMKENF PNFLSACDKK GTNYLADVFE  60
KKDKNEDKKI DFSEFLSLLG DIATDYHKQS HGAAPCSGGS Q                     101

SEQ ID NO: 58          moltype = AA  length = 117
FEATURE                Location/Qualifiers
source                 1..117
                       mol_type = protein
                       organism = Homo sapiens
SEQUENCE: 58
MSLVSCLSED LKVLFFRWGK SVGIMLTELE KALNSIIDVY HKYSLIKGNF HAVYRDDLKK  60
LLETECPQYI RKKGADVWFK ELDINTDGAV NFQEFLILVI KMGVAAHKKS HEESHKE     117

SEQ ID NO: 59          moltype = AA  length = 114
FEATURE                Location/Qualifiers
source                 1..114
                       mol_type = protein
                       organism = Homo sapiens
SEQUENCE: 59
MTCKMSQLER NIETIINTFH QYSVKLGHPD TLNQGEFKEL VRKDLQNFLK KENKNEKVIE  60
HIMEDLDTNA DKQLSFEEFI MLMARLTWAS HEKMHEGDEG PGHHHKPGLG EGTP        114

SEQ ID NO: 60          moltype = AA  length = 2426
FEATURE                Location/Qualifiers
source                 1..2426
                       mol_type = protein
                       organism = Homo sapiens
SEQUENCE: 60
MATNIEQIFR SFVVSKFREI QQELSSGRNE GQLNGETNTP IEGNQAGDAA ASARSLPNEE  60
IVQKIEEVLS GVLDTELRYK PDLKEGSRKS RCVSVQTDPT DEIPTKKSKK HKKHKNKKKK  120
KKKEKEKKYK RQPEESESKT KSHDDGNIDL ESDSFLKFDS EPSAVALELP TRAFGPSETN  180
ESPAVVLEPP VVSMEVSEPH ILETLKPATK TAELSVVSTS VISEQSEQSV AVMPEPSMTK  240
ILDSFAAAPV PTTTLVLKSS EPVVTMSVEY QMKSVLKSVE STSPEPSKIM LVEPPVAKVL  300
EPSETLVVSS ETPTEVYPEP STSTTMDFPE SSAIEALRLP EQPVDVPSEI ADSSMTRPQE  360
LPELPKTTAL ELQESSVASA MELPGPPATS MPELQGPPVT PVLELPGPSA TPVPELPGPL  420
STPVPELPGP PATAVPELPG PSVTPVPQLS QELPGLPAPS MGLEPPQEVP EPPVMAQELP  480
GLPLVTAAVE LPEQPAVTVA MELTEQPVTT TELEQPVGMT TVEHPGHPEV TTATGLLGQP  540
EATMVLELPG QPVATTALEL PGQPSVTGVP ELPGLPSATR ALELSGQPVA TGALELPGPL  600
MAAGALEFSG QSGAAGALEL LGQPLATGVL ELPGQPGAPE LPGQPVATVA LEISVQSVVT  660
TSELSTMTVS QSLEVPSTTA LESYNTVAQE LPTTLVGETS VTVGVDPLMA PESHILASNT  720
METHILASNT MDSQMLASNT MDSQMLASNT MDSQMLASST MDSQMLATSS MDSQMLATSS  780
MDSQMLATST MDSQMLATSS MDSQMLATSS MDSQMLATSS MDSQMLATSS MDSQMLATST  840
MDSQMLATST MDSQMLATSS MDSQMLASGT MDSQMLASGT MDAQMLASGT MDAQMLASST  900
QDSAMLGSKS PDPYRLAQDP YRLAQDPYRL GHDPYRLGHD AYRLGQDPYR LGHDPYRLTP  960
DPYRMSPRPY RIAPRSYRIA PRPYRLAPRP LMLASRRSMM MSYAAERSMM SSYERSMMSY  1020
ERSMMSPMAE RSMMSAYERS MMSAYERSMM SPMAERSMMS AYERSMMSAY ERSMMSPMAD  1080
RSMMSMGADR SMMSSYSAAD RSMMSSYSAA DRSMMSSYTA DRSMMSMAAD SYTDSYTDTY  1140
TEAYMVPPLP PEEPPTMPPL PPEEPPMTPP LPPEEPPEGP ALPTEQSALT AENTWPTEVP  1200
SLPSEESVSQ PEPPVSQSEI SEPSAVPTDY SVSASDPSVL VSEAAVTVPE PPPEPESSIT  1260
LTPVESAVVA EEHEVVPERP VTCMVSETPA MSAEPTVLAS EPPVMSETAE TFDSMRASGH  1320
VASEVSTSLL VPAVTTPVLA ESILEPPAMA APESSAMAVL ESSAVTVLES STVTVLESST  1380
VTVLEPSVVT VPEPPVVAEP DYVTIPVPVV SALEPSVPVL EPAVSVLQPS MIVSEPSVSV  1440
QESTVTVSEP AVTVSEQTQV IPTEVAIEST PMILESSIMS SHVMKGINLS SGDQNLAPEI  1500
GMQEIALHSG EEPHAEEHLK GDFYESEHGI NIDLNINNHL IAKEMEHNTV CAAGTSPVGE  1560
IGEEKILPTS ETKQRTVLDT YPGVSEADAG ETLSSTGPFA LEPDATGTSK GIEFTTASTL  1620
SLVNKYDVDL SLTTQDTEHD MVISTSPSGG SEADIEGPLP AKDIHLDLPS NNNLVSKDTE  1680
EPLPVKESDQ TLAALLSPKE SSGGEKEVPP PPKETLPDSG FSANIEDINE ADLVRPLLPK  1740
DMERLTSLRA GIEGPLLASD VGRDRSAASP VVSSMPERAS ESSSEEKDDY EIFVKVKDTH  1800
EKSKKNKNRD KGEKEKKRDS SLRSRSKRSK SSEHKSRKRT SESRSRARKR SSKSKSHRSQ  1860
TRSRSRSRRR RRSSRSRSKS RGRRSVSKEK RKRSPKHRSK SRERKRKRSS SRDNRKTVRA  1920
RSRTPSRRSR SHTPSRRRRS RSVGRRRSFS ISPSRRSRTP SRRSRTPSRR SRTPSRRSRT  1980
PSRRSRTPSR RSRTPSRRRR SRSVVRRRSF SISPVRLRRS RTPLRRRFSR SPIRRKRSRS  2040
SERGRSPKRL TDLDKAQLLE IAKANAAAMC AKAGVPLPPN LKPAPPPTIE EKVAKKSGGA  2100
TIEELTEKCK QIAQSKEDDD VIVNKPHVSD EEEEEPPFYH HPFKLSEPKP IFFNLNIAAA  2160
KPTPPKSQVT LTKEFPVSSG SQHRKKEADS VYGEWVPVEK NGEENKDDDN VFSSNLPSEP  2220
VDISTAMSER ALAQKRLSEN AFDLEAMSML NRAQERIDAW AQLNSIPGQF TGSTGVQVLT  2280
QEQLANTGAQ AWIKKDQFLR AAPVTGGMGA VLMRKMGWRE GEGLGKNKEG NKEPILVDFK  2340
TDRKGLVAVG ERAQKRSGNF SAAMKDLSGK HPVSALMEIC NKRRWQPPEF LLVHDSGPDH  2400
RKHFLFRVLR NGALTRPNCM FFLNRY                                      2426
```

```
SEQ ID NO: 61          moltype = AA  length = 370
FEATURE                Location/Qualifiers
source                 1..370
                       mol_type = protein
                       organism = Homo sapiens
SEQUENCE: 61
MVGKLKQNLL LACLVISSVT VFYLGQHAME CHHRIEERSQ PVKLESTRTT VRTGLDLKAN  60
KTFAYHKDMP LIFIGGVPRS GTTLMRAMLD AHPDIRCGEE TRVIPRILAL KQMWSRSSKE  120
KIRLDEAGVT DEVLDSAMQA FLLEIIVKHG EPAPYLCNKD PFALKSLTYL SRLFPNAKFL  180
LMVRDGRASV HSMISRKVTI AGFDLNSYRD CLTKWNRAIE TMYNQCMEVG YKKCMLVHYE  240
QLVLHPERWM RTLLKFLQIP WNHSVLHHEE MIGKAGGVSL SKVERSTDQV IKPVNVGALS  300
KWVGKIPPDV LQDMAVIAPM LAKLGYDPYA NPPNYGKPDP KIIENTRRVY KGEFQLPDFL  360
KEKPQTEQVE                                                        370

SEQ ID NO: 62          moltype = AA  length = 917
FEATURE                Location/Qualifiers
source                 1..917
                       mol_type = protein
                       organism = Homo sapiens
SEQUENCE: 62
MAETLSGLGD SGAAGAAALS SASSETGTRR LSDLRVIDLR AELRKRNVDS SGNKSVLMER  60
LKKAIEDEGG NPDEIEITSE GNKKTSKRSS KGRKPEEEGV EDNGLEENSG DGQEDVETSL  120
ENLQDIDIMD ISVLDEAEID NGSVADCVED DDADNLQESL SDSRELVEGE MKELPEQLQE  180
HAIEDKETIN NLDTSSSDFT ILQEIEEPSL EPENEKILDI LGETCKSEPV KEESSELEQP  240
FAQDTSSVGP DRKLAEEEDL FDSAHPEEGD LDLASESTAH AQSSKADSLL AVVKREPAEQ  300
PGDGERTDCE PVGLEPAVEQ SSAASELAEA SSEELAEAPT EAPSPEARDS KEDGRKFDFD  360
ACNEVPPAPK ESSTSEGADQ KMSSPEDDSD TKRLSKEEKG RSSCGRNFWV SGLSSTTRAT  420
DLKNLFSKYG KVVGAKVVTN ARSPGARCYG FVTMSTAEEA TKCINHLHKT ELHGKMISVE  480
KAKNEPVGKK TSDKRDSDGK KEKSSNSDRS TNLKRDDKCD RKDDAKKGDD GSGEKSKDQD  540
DQKPGPSERS RATKSGSRGT ERTVVMDKSK GVPVISVKTS GSKERASKSQ DRKSASREKR  600
SVVSFDKVKE PRKSRDSESH SRVRERSERE QRMQAQWERE ERERLEIARE RLAFQRQRLE  660
RERMERERLE RERMHVEHER RREQERIHRE REELRRQQEL RYEQERRPAV RRPYDLDRRD  720
DAYWPEAKRA ALDERYHSDF NRQDRFHDFD HRDRGRYPDH SVDRREGSRS MMGEREGQHY  780
PERHGGPERH GRDSRDGWGG YGSDKRMSEG RGLPPPPRGR RDWGDHGRRE DDRSWQGTAD  840
GGMMDRDHKR WQGGERSMSG HSGPGHMMNR GGMSGRGSFA PGGASRGHPI PHGGMQGGFG  900
GQSRGSRPSD ARFTRRY                                                917

SEQ ID NO: 63          moltype = AA  length = 835
FEATURE                Location/Qualifiers
source                 1..835
                       mol_type = protein
                       organism = Homo sapiens
SEQUENCE: 63
MGNYKSRPTQ TCTDEWKKKV SESYVITIER LEDDLQIKEK ELTELRNIFG SDEAFSKVNL  60
NYRTENGLSL LHLCCICGGK KSHIRTLMLK GLRPSRLTRN GFTALHLAVY KDNAELITSL  120
LHSGADIQQV GYGGLTALHI ATIAGHLEAA DVLLQHGANV NIQDAVFFTP LHIAAYYGHE  180
QVTRLLLKFG ADVNVSGEVG DRPLHLASAK GFLNIAKLLM EEGSKADVNA QDNEDHVPLH  240
FCSRFGHHDI VKYLLQSDLE VQPHVVNIYG DTPLHLACYN GKFEVAKEII QISGTESLTK  300
ENIFSETAFH SACTYGKSID LVKFLLDQNV ININHQGRDG HTGLHSACYH GHIRLVQFLL  360
DNGADMNLVA CDPSRSSGEK DEQTCLMWAY EKGHDAIVTL LKHYKRPQDE LPCNEYSQPG  420
GDGSYVSVPS PLGKIKSMTK EKADILLLRA GLPSHFHLQL SEIEFHEIIG SGSFGKVYKG  480
RCRNKIVAIK RYRANTYCSK SDVDMFCREV SILCQLNHPC VIQFVGACLN DPSQFAIVTQ  540
YISGGSLFSL LHEQKRILDL QSKLIIAVDV AKGMEYLHNL TQPIIHRDLN SHNILLYEDG  600
HAVVADFGES RFLQSLDEDN MTKQPGNLRW MAPEVFTQCT RYTIKADVFS YALCLWEILT  660
GEIPFAHLKP AAAAADMAYH HIRPPIGYSI PKPISSLLIR GWNACPEGRP EFSEVVMKLE  720
ECLCNIELMS PASSNSSGSL SPSSSSDCLV NRGGPGRSHV AALRSRFELE YALNARSYAA  780
LSQSAGQYSS QGLSLEEMKR SLQYTPIDKY GYVSDPMSSM HFHSCRNSSS FEDSS      835

SEQ ID NO: 64          moltype = AA  length = 425
FEATURE                Location/Qualifiers
source                 1..425
                       mol_type = protein
                       organism = Homo sapiens
SEQUENCE: 64
MDSLVTANTK FCFDLFQEIG KDDRHKNIFF SPLSLSAALG MVRLGARSDS AHQIDEVLHF  60
NEFSQNESKE PDPCLKSNKQ KVLADSSLEG QKKTTEPLDQ QAGSLNNESG LVSCYFGQLL  120
SKLDRIKTDY TLSIANRLYG EQEFPICQEY LDGVIQFYHT TIESVDFQKN PEKSRQEINF  180
WVECQSQGKI KELFSKDAIN AETVLVLVNA VYFKAKWETY FDHENTVDAP FCLNANENKS  240
VKMMTQKGLY RIGFIEEVKA QILEMRYTKG KLSMFVLLPS HSKDNLKGLE ELERKITYEK  300
MVAWSSSENM SEESVVLSFP RFTLEDSYDL NSILQDMGIT DIFDETRADL TGISPSPNLY  360
LSKIIHKTFV EVDENGTQAA AATGAVVSER SLRSWVEFNA NHPFLFFIRH NKTQTILFYG  420
RVCSP                                                             425

SEQ ID NO: 65          moltype = AA  length = 390
FEATURE                Location/Qualifiers
source                 1..390
                       mol_type = protein
                       organism = Homo sapiens
SEQUENCE: 65
```

```
MNSLSEANTK FMFDLFQQFR KSKENNIFYS PISITSALGM VLLGAKDNTA QQIKKVLHFD  60
QVTENTTGKA ATYHVDRSGN VHHQFQKLLT EFNKSTDAYE LKIANKLFGE KTYLFLQEYL  120
DAIKKFYQTS VESVDFANAP EESRKKINSW VESQTNEKIK NLIPEGNIGS NTTLVLVNAI  180
YFKGQWEKKF NKEDTKEEKF WPNKNTYKSI QMMRQYTSFH FASLEDVQAK VLEIPYKGKD  240
LSMIVLLPNE IDGLQKLEEK LTAEKLMEWT SLQNMRETRV DLHLPRFKVE ESYDLKDTLR  300
TMGMVDIFNG DADLSGMTGS RGLVLSGVLH KAFVEVTEEG AEAAAATAVV GFGSSPTSTN  360
EEFHCNHPFL FFIRQNKTNS ILFYGRFSSP                                  390

SEQ ID NO: 66          moltype = AA  length = 390
FEATURE                Location/Qualifiers
source                 1..390
                       mol_type = protein
                       organism = Homo sapiens
SEQUENCE: 66
MNSLSEANTK FMFDLFQQFR KSKENNIFYS PISITSALGM VLLGAKDNTA QQISKVLHFD  60
QVTENTTEKA ATYHVDRSGN VHHQFQKLLT EFNKSTDAYE LKIANKLFGE KTYQFLQEYL  120
DAIKKFYQTS VESTDFANAP EESRKKINSW VESQTNEKIK NLFPDGTIGN DTTLVLVNAI  180
YFKGQWENKF KKENTKEEKF WPNKNTYKSV QMMRQYNSFN FALLEDVQAK VLEIPYKGKD  240
LSMIVLLPNE IDGLQKLEEK LTAEKLMEWT SLQNMRETCV DLHLPRFKME ESYDLKDTLR  300
TMGMVNIFNG DADLSGMTWS HGLSVSKVLH KAFVEVTEEG VEAAAATAVV VVELSSPSTN  360
EEFCCNHPFL FFIRQNKTNS ILFYGRFSSP                                  390

SEQ ID NO: 67          moltype = AA  length = 1085
FEATURE                Location/Qualifiers
source                 1..1085
                       mol_type = protein
                       organism = Homo sapiens
SEQUENCE: 67
MSTPSRFKKD KEIIAEYESQ VKEIRAQLVE QQKCLEQQTE MRVQLLQDLQ DFFRKKAEIE  60
TEYSRNLEKL AERFMAKTRS TKDHQQYKKD QNLLSPVNCW YLLLNQVRRE SKDHATLSDI  120
YLNNVIMRFM QISEDSTRMF KKSKEIAFQL HEDLMKVLNE LYTVMKTYHM YHAESISAES  180
KLKEAEKQEE KQIGRSGDPV FHIRLEERHQ RRSSVKKIEK MKEKRQAKYS ENKLKSIKAR  240
NEYLLTLEAT NASVFKYYIH DLSDLIDCCD LGYHASLNRA LRTYLSAEYN LETSRHEGLD  300
IIENAVDNLE PRSDKQRFME MYPAAFCPPM KFEFQSHMGD EVCQVSAQQP VQAELMLRYQ  360
QLQSRLATLK IENEEVKKTT EATLQTIQDM VTIEDYDVSE CFQHSRSTES VKSTVSETYL  420
SKPSIAKRRA NQQETEQFYF MKLREYLEGS NLITKLQAKH DLLQRTLGEG HRAEYMTTRP  480
PNVPPKPQKH RKSRPRSQYN TKLFNGDLET FVKDSGQVIP LIVESCIRFI NLYGLQHQGI  540
FRVSGSQVEV NDIKNSFERG ENPLADDQSN HDINSVAGVL KLYFRGLENP LFPKERFNDL  600
ISCIRIDNLY ERALHIRKLL LTLPRSVLIV MRYLFAFLNH LSQYSDENMM DPYNLAICFG  660
PTLMPVPEIQ DQVSCQAHVN EIIKTIIIHH ETIFPDAKEL DGPVYEKCMA GDDYCDSPYS  720
EHGTLEEVDQ DAGTEPHTSE DECEPIEAIA KFDYVGRSAR ELSFKKGASL LLYHRASEDW  780
WEGRHNGIDG LVPHQYIVVQ DMDDTFSDTL SQKADSEASS GPVTEDKSSS KDMNSPTDRH  840
PDGYLARQRK RGEPPPPVRR PGRTSDGHCP LHPPHALSNS SVDLGSPSLA SHPRGLLQNR  900
GLNNDSPERR RRPGHGSLTN ISRHDSLKKI DSPPIRRSTS SGQYTGFNDH KPLDPETIAQ  960
DIEETMNTAL NELRELERQS TAKHAPDVVL DTLEQVKNSP TPATSTESLS PLHNVALRSS  1020
EPQIRRSTSS SSDTMSTFKP MVAPRMGVQL KPPALRPKPA VLPKTNPTIG PAPPPQGPTD  1080
KSCTM                                                             1085

SEQ ID NO: 68          moltype = AA  length = 122
FEATURE                Location/Qualifiers
source                 1..122
                       mol_type = protein
                       organism = Homo sapiens
SEQUENCE: 68
MKLLTGLVFC SLVLGVSSRS FFSFLGEAFD GARDMWRAYS DMREANYIGS DKYFHARGNY  60
DAAKRGPGGA WAAEVISDAR ENIQRFFGHG AEDSLADQAA NEWGRSGKDP NHFRPAGLPE  120
KY                                                                122

SEQ ID NO: 69          moltype = AA  length = 130
FEATURE                Location/Qualifiers
source                 1..130
                       mol_type = protein
                       organism = Homo sapiens
SEQUENCE: 69
MRLFTGIVFC SLVMGVTSES WRSFFKEALQ GVGDMGRAYW DIMISNHQNS NRYLYARGNY  60
DAAQRGPGGV WAAKLISRSR VYLQGLIDCY LFGNSSTVLE DSKSNEKAEE WGRSGKDPDR  120
FRPDGLPKKY                                                        130

SEQ ID NO: 70          moltype = AA  length = 223
FEATURE                Location/Qualifiers
source                 1..223
                       mol_type = protein
                       organism = Homo sapiens
SEQUENCE: 70
MNKPLLWISV LTSLLEAFAH TDLSGKVFVF PRESVTDHVN LITPLEKPLQ NFTLCFRAYS  60
DLSRAYSLFS YNTQGRDNEL LVYKERVGEY SLYIGRHKVT SKVIEKFPAP VHICVSWESS  120
SGIAEFWING TPLVKKGLRQ GYFVEAQPKI VLGQEQDSYG GKFDRSQSFV GEIGDLYMWD  180
SVLPPENILS AYQGTPLPAN ILDWQALNYE IRGYVIIKPL VWV                   223
```

```
SEQ ID NO: 71          moltype = AA  length = 72
FEATURE                Location/Qualifiers
source                 1..72
                       mol_type = protein
                       organism = Homo sapiens
SEQUENCE: 71
MSYQQQQCKQ PCQPPPVCPT PKCPEPCPPP KCPEPCPPPK CPQPCPPQQC QQKCPPVTPS  60
PPCQPKCPPK SK                                                      72

SEQ ID NO: 72          moltype = AA  length = 855
FEATURE                Location/Qualifiers
source                 1..855
                       mol_type = protein
                       organism = Homo sapiens
SEQUENCE: 72
MVVMARLSRP ERPDLVFEEE DLPYEEEIMR NQFSVKCWLR YIEFKQGAPK PRLNQLYERA  60
LKLLPCSYKL WYRYLKARRA QVKHRCVTDP AYEDVNNCHE RAFVFMHKMP RLWLDYCQFL  120
MDQGRVTHTR RTFDRALRAL PITQHSRIWP LYLRFLRSHP LPETAVRGYR RFLKLSPESA  180
EEYIEYLKSS DRLDEAAQRL ATVVNDERFV SKAGKSNYQL WHELCDLISQ NPDKVQSLNV  240
DAIIRGGLTR FTDQLGKLWC SLADYYIRSG HFEKARDVYE EAIRTVMTVR DFTQVFDSYA  300
QFEESMIAAK METASELGRE EEDDVDLELR LARFEQLISR RPLLLNSVLL RQNPHHVHEW  360
HKRVALHQGR PREIINTYTE AVQTVDPFKA TGKPHTLWVA FAKFYEDNGQ LDDARVILEK  420
ATKVNFKQVD DLASVWCQCG ELELRHENYD EALRLLRKAT ALPARRAEYF DGSEPVQNRV  480
YKSLKVWSML ADLEESLGTF QSTKAVYDRI LDLRIATPQI VINYAMFLEE HKYFEESFKA  540
YERGISLFKW PNVSDIWSTY LTKFIARYGG RKLERARDLF EQALDGCPPK YAKTLYLLYA  600
QLEEEWGLAR HAMAVYERAT RAVEPAQQYD MFNIYIKRAA EIYGVTHTRG IYQKAIEVLS  660
DEHAREMCLR FADMECKLGE IDRARAIYSF CSQICDPRTT GAFWQTWKDF EVRHGNEDTI  720
KEMLRIRRSV QATYNTQVNF MASQMLKVSG SATGTVSDLA PGQSGMDDMK LLEQRAEQLA  780
AEAERDQPLR AQSKILFVRS DASREELAEL AQQVNPEEIQ LGEDEDEDEM DLEPNEVRLE  840
QQSVPAAVFG SLKED                                                   855

SEQ ID NO: 73          moltype = AA  length = 2785
FEATURE                Location/Qualifiers
source                 1..2785
                       mol_type = protein
                       organism = Homo sapiens
SEQUENCE: 73
MKTKPVSHKT ENTYRFLTFA ERLGNVNIDI IHRIDRTASY EEEVETYFFE GLLKWRELNL  60
TEHFGKFYKE VIDKCQSFNQ LVYHQNEIVQ SLKTHLQVKN SFAYQPLLDL VVQLARDLQM  120
DFYPHFPEFF LTITSILETQ DTELLEWAFT SLSYLYKYLW RLMVKDMSSI YSMYSTLLAH  180
KKLHIRNFAA ESFTFLMRKV SDKNALFNLM FLDLDKHPEK VEGVGQLLFE MCKGVRNMFH  240
SCTGQAVKLI LRKLGPVTET ETQLPWMLIG ETLKNMVKST VSYISKEHFG TFFECLQESL  300
LDLHTKVTKT NCCESSEQIK RLLETYLILV KHGSGTKIPT PADVCKVLSQ TLQVASLSTS  360
CWETLLDVIS ALILGENVSL PETLIKETIE KIFESRFEKR LIFSFSEVMF AMKQFEQLFL  420
PSFLSYIVNC FLIDDAVVKD EALAILAKLI LNKAAPPTAG SMAIEKYPLV FSPQMVGFYI  480
KQKKTRSKGR NEQFPVLDHL LSIIKLPPNK DTTYLSQSWA ALVVLPHIRP LEKEKVIPLV  540
TGFIEALFMT VDKGSFGKGN LFVLCQAVNT LLSLEESSEL LHLVPVERVK NLVLTFPLEP  600
SVLLLTDLYY QRLALCGCKG PLSQEALMEL FPKLQANIST GVSKIRLLTI RILNHFDVQL  660
PESMEDDGLS ERQSVFAILR QAELVPATVN DYREKLLHLR KLRHDVVQTA VPDGPLQEVP  720
LRYLLGMLYI NFSALWDPVI ELISSHAHEM ENKQFWKVYY EHLEKAATHA EKELQNDMTD  780
EKSVGDESWE QTQEGDVGAL YHEQLALKTD CQERLDHTNF RFLLWRALTK FPERVEPRSR  840
ELSPLFLRFI NNEYYPADLQ VAPTQDLRRK GKGMVAEEIE EEPAAGDDEE LEEEAVPQDE  900
SSQKKKTRRA AAKQLIAHLQ VFSKFSNPRA LYLESKLYEL YLQLLLHQDQ MVQKITLDCI  960
MTYKHPHVLP YRENLQRLLE DRSFKEEIVH FSISEDNAVV KTAHRADLFP ILMRILYGRM  1020
KNKTGSKTQG KSASGTRMAI VLRFLAGTQP EEIQIFLDLL FEPVRHFKNG ECHSAVIQAV  1080
EDLDLSKVLP LGRQHGILNS LEIVLKNISH LISAYLPKIL QILLCMTATV SHILDQREKI  1140
QLRFINPLKN LRRLGIKMVT DIFLDWESYQ FRTEEIDAVF HGAVWPQISR LGSESQYSPT  1200
PLLKLISIWS RNARYFPLLA KQKPGHPECD ILTNVFAILS AKNLSDATAS IVMDIVDDLL  1260
NLPDFEPTET VLNLLVTGCV YPGIAENIGE SITIGGRLIL PHVPAILQYL SKTTISAEKV  1320
KKKKNRAQVS KELGILSKIS KFMKDKEQSS VLITLLLPFL HRGNIAEDTE VDILVTVQNL  1380
LKHCVDPTSF LKPIAKLFSV IKNKLSRKLL CTVFETLSDF ESGLKYITDV VKLNAFDQRH  1440
LDDINFDVRF ETFQTITSYI KEMQIVDVNY LIPVMHNCFY NLELGDMSLS DNASMCLMSI  1500
IKKLAALNVT EKDYREIIHR SLLEKLRKGL KSQTESIQQD YTTILSCLIQ TFPNQLEFKD  1560
LVQLTHYHDP EMDFFENMKH IQIHRRARAL KKLAKQLMEG KVVLSSKSLQ NYIMPYAMTP  1620
IFDEKMLKHE NITTAATEII GAICKHLSWS AYMYYLKHFI HVLQTGQINQ KLGVSLLVIV  1680
LEAFHFDHKT LEEQMGKIEN EENAIEAIEL PEPEAMELER VDEEEKEYTC KSLSDNGQPG  1740
TPDPADSGGT SAKESECITK PVSFLPQNKE EIERTIKNIQ GTITGDILPR LHKCLASTTK  1800
REEEHKLVKS KVVNDEEVVR VPLAFAMVKL MQSLPQEVME ANLPSILLKV CALLKNRAQE  1860
IRDIARSTLA KIIEDLGVHF LLYVLKELQT TLVRGYQVHV LTFTVHMLLQ GLTNKLQVGD  1920
LDSCLDIMIE IFNHELFGAV AEEKEVKQIL SKVMEARRSK SYDSYEILGK FVGKDQVTKL  1980
ILPLKEILQN TTSLKLARKV HETLRRITVG LIVNQEMTAE SILLLSYGLI SENLPLLTEK  2040
EKNPVAPAPD PRLPPQSCLL LPPTPVRGGQ KAVVSRKTNM HIFIESGLRL LHLSLKTSKI  2100
KSSGECVLEM LDPFVSLLID CLGSMDVKVI TGALQCLIWV LRFPLPSIET KAEQLTKHLF  2160
LLLKDYAKLG AARGQNFHLV VNCFKCVTIL VKKVKSYQIT EKQLQVLLAY AEEDIYDTSR  2220
QATAFGLLKA ILSRKLLVPE IDEVMRKVSK LAVSAQSEPA RVQCRQVFLK YILDYPLGDK  2280
LRPNLEFMLA QLNYEHETGR ESTLEMIAYL FDTFPQGLLH ENCGMFFIPL CLMTINDDSA  2340
TCKKMASMTI KSLLGKISLE KKDWLFDMVT TWFGAKKRLN RQLAALICGL FVESEGVDFE  2400
KRLGTVLPVI EKEIDPENFK DIMEETEEKA ADRLLFSFLT LITKLIKECN IIQFTKPAET  2460
LSKIWSHVHS HLRHPHNWVW LTAAQIFGLL FASCQPEELI QKWNTKKTKK HLPEPVAIKF  2520
```

```
LASDLDQKMK SISLASCHQL HSKFLDQSLG EQVVKNLLFA AKVLYLLELY CEDKQSKIKE  2580
DLEEQEALED GVACADEKAE SDGEEKEEVK EELGRPATLL WLIQKLSRIA KLEAAYSPRN  2640
PLKRTCIFKF LGAVAMDLGI DKVKPYLPMI IAPLFRELNS TYSEQDPLLK NLSQEIIELL  2700
KKLVGLESFS LAFASVQKQA NEKRALRKKR KALEFVTNPD IAAKKKMKKH KNKSEAKKRK  2760
IEFLRPGYKA KRQKSHSLKD LAMVE                                        2785

SEQ ID NO: 74          moltype = AA  length = 926
FEATURE                Location/Qualifiers
source                 1..926
                       mol_type = protein
                       organism = Homo sapiens
SEQUENCE: 74
MKKTRSTTLR RAWPSSDFSD RASDRMRSRS EKDYRLHKRF PAAFAPQASR GYMTSGDVSP  60
ISMSPISQSQ FIPLGEILCL AISAMNSARK PVTQEALMEH LTTCFPGVPT PSQEILRHTL  120
NTLVRERKIY PTPDGYFIVT PQTYFITPSL IRTNSKWYHL DERIPDRSQC TSPQPGTITP  180
SASGCVRERT LPRNHCDSCH CCREDVHSTH APTLQRKSAK DCKDPYCPPS LCQVPPTEKS  240
KSTVNFSYKT ETLSKPKDSE KQSKKFGLKL FRLSFKKDKT KQLANFSAQF PPEEWPLRDE  300
DTPATIPREV EMEIIRRINP DLTVENVMRH TALMKKLEEE KAQRSKAGSS AHHSGRSKKS  360
RTHRKSHGKS RSHSKTRVSK GDPSDGSHLD IPAEREYDFC DPLTRVPREG CFIIEHKGDN  420
FIMHSNTNVL ESHFPMTPEW DVSGELAKRR TEMPFPEPSR GSSHSKVHRS HSHTQDRRSR  480
NERSNKAKER SRSMDNSKGP LGASSLGTPE DLAEGCSQDD QTPSQSYIDD STLRPAQTVS  540
LQRAHISSTS YKEVCIPEIV SGSKEPSSAC SLLEPGKPPE SLPSYGELNS CPTKTATDDY  600
FQCNTSSETV LTAPSPLGKN KEDHDTLTLA EGVKKLSPSD RQVPHSSREP VGHKEESPKG  660
PGGGPAASGG VAEGIANGRL VQHHGAEPSS LDKRKEIFSK DTLFKPLHST LSVNSYHKSS  720
LSLLKSHPKT PADTLPGRCE KLEPSLGTSA AQAMPASQRQ QESGGNQEAS FDYYNVSDDD  780
DSEEGANKNT EEEKNREDVG TMQWLLEREK ERDLQRKFEK NLTLLAPKET DSSSNQRATH  840
SARLDSMDSS SITVDSGFNS PRTRESLASN TSSIVESNRR QNPALSPAHG GAGPAFNFRA  900
SAEPPTNEAE KLQKPSNCLQ ASVTSV                                       926

SEQ ID NO: 75          moltype = AA  length = 2999
FEATURE                Location/Qualifiers
source                 1..2999
                       mol_type = protein
                       organism = Homo sapiens
SEQUENCE: 75
MGNENSTSDN QQEDSVLHNV ILWPPNPEPT QRTLSAQTPR SAQPPGNSQN IKRKQQDTPG  60
SPDHRDASSI GSVGLGGFCT ASESSASLDP CLVSPEVTEP RKDPQGARGP EGSLLPSPPP  120
SQEREHPSSS MPFAECPPEG CLASPAAAPE DGPQTQSPRR EPAPNAPGDI AAAFPAERDS  180
STPYQEIAAV PSAGRERQPK EEGQKSSFSF SSGIDQSPGM SPVPLREPMK APLCGEGDQP  240
GGFESQEKEA AGGFPPAESR QGVASVQVTP EAPAAAQQGT ESSAVLEKSP LKPMAPIPQD  300
PAPRASDRER GQGEAPPQYL TDDLEFLRAC HLPRSNSGAA PEAEVNAASQ ESCQQPVGAY  360
LPHAELPWGL PSPALVPEAG GSGKEALDTI DVQGHPQTGM RGTKPNQVVC VAAGGQPEGG  420
LPVSPEPSLL TPTEEAHPAS SLASFPAAQI PIAVEEPGSS SRESVSKAGM PVSADAAKEV  480
VDAGLVGLER QVSDLGSKGE HPEGDPGEVP APSPQERGEH LNTEQSHEVQ PGVPPPPLPK  540
EQSHEVQPGA PPPPLPKAPS ESARGPPGPT DGAKVHEDST SPAVAKEGSR SPGDSPGGKE  600
EAPEPPDGGD PGNLQGEDSQ AFSSKRDPEV GKDELSKPSS DAESRDHPSS HSAQPPRKGG  660
AGHTDGPHSQ TAEADASGLP HKLGEEDPVL PPVPDGAGEP TVPEGAIWEG SGLQPKCPDT  720
LQSREGLGRM ESFLTLESEK SDFPPTPVAE VAPKAQEGES TLEIRKMGSC DGEGLLTSPD  780
QPRGPACDAS RQEFHAGVPH PPQGENLAAD LGLTALILDQ DQQGIPSCPG EGWIRGAASE  840
WPLLSSEKHL QPSQAQPETS IFDVLKEQAQ PPENGKETSP SHPGFKDQGA DSSQIHVPVE  900
PQEDNNLPTH GGQEQALGSE LQSQLPKGTL SDTPTSSPTD MVWESSLTEE SELSAPTRQK  960
LPALGEKRPE GACGDGQSSR VSPPAADVLK DFSLAGNFSR KETCCTGQGP NKSQQALADA  1020
LEEGSQHEEA CQRHPGASEA ADGCSPLWGL SKREMASGNT GEAPPCQPDS VALLDAVPCL  1080
PALAPASPGV TPTQDAPETE ACDETQEGRQ QPVPAPQQKM ECWATSDAES PKLLASFPSA  1140
GEQGGEAGAA ETGGSAGAGD PGKQQAPEKP GEATLSCGLL QTEHCLTSGE EASTSALRES  1200
CQAEHPMASC QDALLPAREL GGIPRSTMDF STHQAVPDPK ELLLSGPPEV AAPDTPYLHV  1260
DSAAQRGAED SGVKAVSSAD PRAPGESPCP VGEPPLALEN AASLKLFAGS LAPLLQPGAA  1320
GGEIPAVQAS SGSPKARTTE GPVDSMPCLD RMPLLAKGKQ ATGEEKAATA PGAGAKASGE  1380
GMAGDAAGET EGSMERMGEP SQDPKQGTSG GVDTSSEQIA TLTGFPDFRE HIAKIFEKPV  1440
LGALATPGEK AGAGRSAVGK DLTRPLGPEK LLDGPPGVDV TLLPAPPARL QVEKKQQLAG  1500
EAEISHLALQ DPASDKLLGP AGLTWERNLP GAGVGKEMAG VPPTLREDER PEGPGAAWPG  1560
LEGQAYSQLE RSRQELASGL PSPAATQELP VERAAAFQVA PHSHGEEAVA QDRIPSGKQH  1620
QETSACDSPH GEDGPGDFAH TGVPGHVPRS TCAPSPQREV LTVPEANSEP WTLDTLGGER  1680
RPGVTAGILE MRNALGNQST PAPPTGEVAD TPLEPGKVAG AAGEAEGDIT LSTAETQACA  1740
SGDLPEAGTT RTFSVVAGDL VLPGSCQDPA CSDKAPGMEG TAALHGDSPA RPQQAKEQPG  1800
PERPIPAGDG KVCVSSPPEP DETHDPKLQH LAPEELHTDR ESPRPGPSML PSVPKKDAPR  1860
VMDKVTSDET RGAEGTESSP VADDIIQPAA PADLESPTLA ASSYHGDVVG QVSTDLIAQS  1920
ISPAAAHAGL PPSAAEHIVS PSAPAGDRVE ASTPSCPDPA KDLSRSSDSE EAFETPESTT  1980
PVKAPPAPPP PPEVIPEPE VSTQPPPEEP GCGSETVPVP DGPRSDSVEG SPFRPPSHSF  2040
SAVFDEDKPI ASSGTYNLDF DNIELVDTFQ TLEPRASDAK NQEGKVNTRR KSTDSVPISK  2100
STLSRSLSLQ ASDFDGASSS GNPEAVALAP DAYSTGSSSA SSTLKRTKKP RPPSLKKKQT  2160
TKKPTETPPV KETQQEPDEE SLVPSGENLA SETKTESAKT EGPSPALLEE TPLEPAVGPK  2220
AACPLDSESA EGVVPPASGG GRVQNSPPVG RKTLPLTTAP EAGEVTPSDS GGQEDSPAKG  2280
LSVRLEFDYS EDKSSWDNQQ ENPPPTKKIG KKPVAKMPLR RPKMKKTPEK LDNTPASPPR  2340
SPAEPNDIPI AKGTYTFDID KWDDPNFNPF SSTSKMQESP KLPQQSYNFD PDTCDESVDP  2400
FKTSSKTPSS PSKSPASFEI PASAMEANGV DGDGLNKPAK KKKTPLKTDT FRVKKSPKRS  2460
PLSDPPSQDP TPAATPETPP VISAVVHATD EEKLAVTNQK WTCMTVDLEA DKQDYPQPSD  2520
LSTFVNETKF SSPTEGKQLC SQLDPHSASE NPAPREPKAR RETSQPELDY RNSYEIEYME  2580
KIGSSLPQDD DAPKKQALYL MFDTSQESPV KSSPVRMSES PTPCSGSSFE ETEALVNTAA  2640
```

```
KNQHPVPRGL APNQESHLQV PEKSSQKELE AMGLGTPSEA IEITAPEGSF ASADALLSRL  2700
AHPVSLCGAL DYLEPDLAEK NPPLFAQKLQ EELEFAIMRI EALKLARQIA LASRSHQDAK  2760
REAAHPTDVS ISKTALYSRI GTAEVEKPAG LLFQQPDLDS ALQIARAEII TKEREVSEWK  2820
DKYEESRREV MEMRKIVAEY EKTIAQMIED EQREKSVSHQ TVQQLVLEKE QALADLNSVE  2880
KSLADLFRRY EKMKEVLEGF RKNEEVLKRC AQEYLSRVKK EEQRYQALKV HAEEKLDRAN  2940
AEIAQVRGKA QQEQAAHQAS LRKEQLRVDA LERTLEQKNK EIEELTKICD ELIAKMGKS   2999

SEQ ID NO: 76          moltype = AA  length = 914
FEATURE                Location/Qualifiers
source                 1..914
                       mol_type = protein
                       organism = Homo sapiens
SEQUENCE: 76
MANINLKEIT LIVGVVTACY WNSLFCGFVF DDVSAILDNK DLHPSTPLKT LFQNDFWGTP  60
MSEERSHKSY RPLTVLTFRL NYLLSELKPM SYHLLNMIFH AVVSVIFLKV CKLFLDNKSS  120
VIASLLFAVH PIHTEAVTGV VGRAELLSSI FFLAAFLSYT RSKGPDNSII WTPIALTVFL  180
VAVATLCKEQ GITVVGICCV YEVFIAQGYT LPLLCTTAGQ FLRGKGSIPF SMLQTLVKLI  240
VLMFSTLLLV VIRVQVIQSQ LPVFTRFDNP AAVSPTPTRQ LTFNYLLPVN AWLLLNPSEL  300
CCDWTMGTIP LIESLLDIRN LATFTFFCFL GMLGVFSIRY SGDSSKTVLM ALCLMALPFI  360
PASNLFFPVG FVVAERVLYV PSMGFCILVA HGWQKISTKS VFKKLSWICL SMVILTHSLK  420
TFHRNWDWES EYTLFMSALK VNKNNAKLWN NVGHALENEK NFERALKYFL QATHVQPDDI  480
GAHMNVGRTY KNLNRTKEAE ESYMMAKSLM PQIIPGKKYA ARIAPNHLNV YINLANLIRA  540
NESRLEEADQ LYRQAISMRP DFKQAYISRG ELLLKMNKPL KAKEAYLKAL ELDRNNADLW  600
YNLAIVHIEL KEPNEALKNF NRALELNPKH KLALFNSAIV MQESGEVKLR PEARKRLLSY  660
INEEPLDANG YFNLGMLAMD DKKDNEAEIW MKKAIKLQAD FRSALFNLAL LYSQTAKELK  720
ALPILEELLR YYPDHIKGLI LKGDILMNQK KDILGAKKCF ERILEMDPSN VQGKHNLCVV  780
YFEEKDLLKA ERCLLETLAL APHEEYIQRH LNIVRDKISS SSFIEPIFPT SKISSVEGKK  840
IPTESVKEIR GESRQTQIVK TSDNKSQSKS NKQLGKNGDE ETPHKTTKDI KEIEKKRVAA  900
LKRLEEIERI LNGE                                                    914

SEQ ID NO: 77          moltype = AA  length = 344
FEATURE                Location/Qualifiers
source                 1..344
                       mol_type = protein
                       organism = Homo sapiens
SEQUENCE: 77
MASGVGAAFE ELPHDGTCDE CEPDEAPGAE EVCRECGFCY CRRHAEAHRQ KFLSHHLAEY  60
VHGSQAWTPP ADGEGAGKEE AEVKVEQERE IESEAGEESE SEEESESEEE SETEEESEDE  120
SDEESEEDSE EEMEDEQESE AEEDNQEEGE SEAEGETEAE SEFDPEIEME AERVAKRKCP  180
DHGLDLSTYC QEDRQLICVL CPVIGAHQGH QLSTLDEAFE ELRSKDSGGL KAAMIELVER  240
LKFKSSDPKV TRDQMKMFIQ QEFKKVQKVI ADEEQKALHL VDIQEAMATA HVTEILADIQ  300
SHMDRLMTQM AQAKEQLDTS NESAEPKAEG DEEGPSGASE EEDT                   344

SEQ ID NO: 78          moltype = AA  length = 128
FEATURE                Location/Qualifiers
source                 1..128
                       mol_type = protein
                       organism = Homo sapiens
SEQUENCE: 78
MQIFVKTLTG KTITLEVEPS DTIENVKAKI QDKEGIPPDQ QRLIFAGKQL EDGRTLSDYN  60
IQKESTLHLV LRLRGGIIEP SLRQLAQKYN CDKMICRKCY ARLHPRAVNC RKKKCGHTNN  120
LRPKKKVK                                                           128

SEQ ID NO: 79          moltype = AA  length = 2813
FEATURE                Location/Qualifiers
source                 1..2813
                       mol_type = protein
                       organism = Homo sapiens
SEQUENCE: 79
MIPARFAGVL LALALILPGT LCAEGTRGRS STARCSLFGS DFVNTFDGSM YSFAGYCSYL  60
LAGGCQKRSF SIIGDFQNGK RVSLSVYLGE FFDIHLFVNG TVTQGDQRVS MPYASKGLYL  120
ETEAGYYKLS GEAYGFVARI DGSGNFQVLL SDRYFNKTCG LCGNFNIFAE DDFMTQEGTL  180
TSDPYDFANS WALSSGEQWC ERASPPSSSC NISSGEMQKG LWEQCQLLKS TSVFARCHPL  240
VDPEPFVALC EKTLCECAGG LECACPALLE YARTCAQEGM VLYGWTDHSA CSPVCPAGME  300
YRQCVSPCAR TCQSLHINEM CQERCVDGCS CPEGQLLDEG LCVESTECPC VHSGKRYPPG  360
TSLSRDCNTC ICRNSQWICS NEECPGECLV TGQSHFKSFD NRYFTFSGIC QYLLARDCQD  420
HSFSIVIETV QCADDRDAVC TRSVTVRLPG LHNSLVKLKH GAGVAMDGQD VQLPLLKGDL  480
RIQHTVTASV RLSYGEDLQM DWDGRGRLLV KLSPVYAGKT CGLCGNYNGN QGDDFLTPSG  540
LAEPRVEDFG NAWKLHGDCQ DLQKQHSDPC ALNPRMTRFS EEACAVLTSP TFEACHRAVS  600
PLPYLRNCRY DVCSCSDGRE CLCGALASYA AACAGRGVRV AWREPGRCEL NCPKGQVYLQ  660
CGTPCNLTCR SLSYPDEECN EACLEGCFCP PGLYMDERGD CVPKAQCPCY YDGEIFQPED  720
IFSDHHTMCY CEDGFMHCTM SGVPGSLLPD AVLSSPLSHR SKRSLSCRPP MVKLVCPADN  780
LRAEGLECTK TCQNYDLECM SMGCVSGCLC PPGMVRHENR CVALERCPCF HQGKEYAPGE  840
TVKIGCNTCV CRDRKWNCTD HVCDATCSTI GMAHYLTFDG LKYLFPGECQ YVLVQDYCGS  900
NPGTFRILVG NKGCSHPSVK CKKRVTILVE GGEIELFDGE VNVKRPMKDE THFEVVESGR  960
YIILLLGKAL SVVWDRHLSI SVVLKQTYQE KVCGLCGNFD GIQNNDLTSS NLQVEEDPVD  1020
FGNSWKVSSQ CADTRKVPLD SSPATCHNNI MKQTMVDSSC RILTSDVFQD CNKLVDPEPY  1080
LDVCIYDTCS CESIGDCACF CDTIAAYAHV CAQHGKVVTW RTATLCPQSC EERNLRENGY  1140
ECEWRYNSCA PACQVTCQHP EPLACPVQCV EGCHAHCPPG KILDELLQTC VDPEDCPVCE  1200
```

```
VAGRRFASGK KVTLNPSDPE HCQICHCDVV NLTCEACQEP GGLVVPPTDA PVSPTTLYVE  1260
DISEPPLHDF YCSRLLDLVF LLDGSSRLSE AEFEVLKAFV VDMMERLRIS QKWVRVAVVE  1320
YHDGSHAYIG LKDRKRPSEL RRIASQVKYA GSQVASTSEV LKYTLFQIFS KIDRPEASRI  1380
TLLLMASQEP QRMSRNFVRY VQGLKKKKVI VIPVGIGPHA NLKQIRLIEK QAPENKAFVL  1440
SSVDELEQQR DEIVSYLCDL APEAPPPTLP PDMAQVTVGP GLLGVSTLGP KRNSMVLDVA  1500
FVLEGSDKIG EADFNRSKEF MEEVIQRMDV GQDSIHVTVL QYSYMVTVEY PFSEAQSKGD  1560
ILQRVREIRY QGGNRTNTGL ALRYLSDHSF LVSQGDREQA PNLVYMVTGN PASDEIKRLP  1620
GDIQVVPIGV GPNANVQELE RIGWPNAPIL IQDFETLPRE APDLVLQRCC SGEGLQIPTL  1680
SPAPDCSQPL DVILLLDGSS SFPASYFDEM KSFAKAFISK ANIGPRLTQV SVLQYGSITT  1740
IDVPWNVVPE KAHLLSLVDV MQREGGPSQI GDALGFAVRY LTSEMHGARP GASKAVVILV  1800
TDVSVDSVDA AADAARSNRV TVFPIGIGDR YDAAQLRILA GPAGDSNVVK LQRIEDLPTM  1860
VTLGNSFLHK LCSGFVRICM DEDGNEKRPG DVWTLPDQCH TVTCQPDGQT LLKSHRVNCD  1920
RGLRPSCPNS QSPVKVEETC GCRWTCPCVC TGSSTRHIVT FDGQNFKLTG SCSYVLFQNK  1980
EQDLEVILHN GACSPGARQG CMKSIEVKHS ALSVELHSDM EVTVNGRLVS VPYVGGNMEV  2040
NVYGAIMHEV RFNHLGHIFT FTPQNNEFQL QLSPKTFASK TYGLCGICDE NGANDFMLRD  2100
GTVTTDWKTL VQEWTVQRPG QTCQPILEEQ CLVPDSSHCQ VLLLPLFAEC HKVLAPATFY  2160
AICQQDSCHQ EQVCEVIASY AHLCRTNGVC VDWRTPDFCA MSCPPSLVYN HCEHGCPRHC  2220
DGNVSSCGDH PSEGCFCPPD KVMLEGSCVP EEACTQCIGE DGVQHQFLEA WVPDHQPCQI  2280
CTCLSGRKVN CTTQPCPTAK APTCGLCEVA RLRQNADQCC PEYECVCDPV SCDLPPVPHC  2340
ERGLQPTLTN PGECRPNFTC ACRKEECKRV SPPSCPPHRL PTLRKTQCCD EYECACNCVN  2400
STVSCPLGYL ASTATNDCGC TTTTCLPDKV CVHRSTIYPV GQFWEEGCDV CTCTDMEDAV  2460
MGLRVAQCSQ KPCEDSCRSG FTYVLHEGEC CGRCLPSACE VVTGSPRGDS QSSWKSVGSQ  2520
WASPENPCLI NECVRVKEEV FIQQRNVSCP QLEVPVCPSG FQLSCKTSAC CPSCRCERME  2580
ACMLNGTVIG PGKTVMIDVC TTCRCMVQVG VISGFKLECR KTTCNPCPLG YKEENNTGEC  2640
CGRCLPTACT IQLRGGQIMT LKRDETLQDG CDTHFCKVNE RGEYFWEKRV TGCPPFDEHK  2700
CLAEGGKIMK IPGTCCDTCE EPECNDITAR LQYVKVGSCK SEVEVDIHYC QGKCASKAMY  2760
SIDINDVQDQ CSCCSPTRTE PMQVALHCTN GSVVYHEVLN AMECKCSPRK CSK         2813

SEQ ID NO: 80           moltype = AA  length = 2912
FEATURE                 Location/Qualifiers
source                  1..2912
                        mol_type = protein
                        organism = Homo sapiens
SEQUENCE: 80
MSSPRLIPLW KDLKLLLNDT INKSKQPSED PKNCLIVLSD RSQVLFKESR YPQNMPCVCY  60
YFSDAHFFAS LSWVTSNTKE IQAVAWMKSK TEDMVEKRTF SMTERLPPIQ SMVHAGSFHI  120
LVVYCGDLIL RLFGDHFRAF KPLGKVPCRF NISCLCYDPE MKMLLSGILG AVVTWVIELG  180
GTGLQIAHMV SMPGDELVQD IVLNGPSGSL LALCETVVRV LMHQGKGQLG EVKRFTSTSS  240
GSSITCCFTC FDQGFLYAGN QAGEIQVWSL QQGHPLHSFQ AHQSGVICIR SRPEAHTLLT  300
AGSDSLIKEW NLTSGSLLRR LELGEELYRL QFIDSITFFC QTAHSFSLHR LPCFYSLFNV  360
CGSAPQQLRR VCCGNNWFRI LCTTEDGLLR FVSPVTGDLL VITWPFSILD QAVDWAYDPG  420
KEELFVATGS SEVLVFDTTR CPCPAKYLLG TSPNSQDFVQ CLAYGHFNLG RGLEGLIFSG  480
HQSGVIRVLS QHSCARLEKF MHFGAVLALS TLSGGIFGGQ GNSLLCSYGM DDYVHLSEAV  540
LDGVKVQLRP LASILSSCHL THLILLPKSV GAITETNCLR LWKFHDFLSS GSQNGLKFIE  600
TLPLHLCAIT SFDVCLSLSL FVTGSADGSV RIWDFHGRLI GILDSSLHFG PVCFANDRGD  660
LLVTFNQSLY LVSCLKLLPP ALLTRLSFMS ISDEVLEVPK PFIPSFFFSF ETMFVPKYIY  720
PGQAQQKLVG LEKLVNNRAI AFDHSVPHVI EEDEEGSPVL LRSSMHYSLQ DMEDWMQVSK  780
RYQCHYVLPP QLQLTSWDGL NPYQILRYYF GHGREWLFAP DCYIPNSVIR ARLWPEGTPI  840
YLQCNLHAPQ RELEWDRSQE FFFWHSRVRA ISNTEYPKNK EEDEHFLEMR LSKDVTYSVL  900
TDGANRSWLG RKMSEITINS MIETMLNIMV HASLLKYQCC VGALGQIFAS YQVSPALRSE  960
TARRLLNDTT NSNPLIRELA WEGLKRLGMI THLFAMPLAQ GLMDKDERVR IKTLSLMAEI  1020
GIHSRTSLLQ LTQKQETFRE MQQQMIGEEP LDHLLGMRAT DLQILSTQVE QRLNENLTLS  1080
HRDEKPAFSL DVSMPSELKS SLKPPTVSEE SEVAIKPSKG QRRGQAGVKK HSQKWLRGLK  1140
KTKERDSKQM STEPGLLEDE SGTEAAPIEM EEASVYSQWS SSTSVIKLSK DVDSQEKDIS  1200
KDHIALTLKR LQKIRDKRDK KATAQKLKKK HKKKGKEAKV INEETTPPVM EQPVTKKVKI  1260
QGRGASGISG RRSTAGDGSS WRDDLCRLMA LRISGSQTKM SENLNAELVT FAQEMLVDRH  1320
PSWELFQEIC PLLKKESKVL LEDLDWDVVP PEKKPIFIQE GAIREDMIQG VTQEVIRHKE  1380
VMPREEEQAQ KKARDMLGLE ETQVILKKGK KVIFLEPGNV TMGKEISKKE EKKTFQKSPK  1440
QGRKAVQKER KVGKIKREMT KEERDMSEEV EEMATLEEKV VKQEGKLVMI ERTPSWQDWK  1500
KAWDEWKQVH GETRKSWKAW KEEWEKRLLQ EEEKLHQAGE KLSPEEEMLQ EDKKLKWEEW  1560
KQVWENMLSS KSKEQQYKDE EEVTLEEEVS REGEEKEQQV TEEQRHIQEE HKWARIHRKR  1620
ARAEKKRAQE ERKLAQEEEK LAQEERQLAQ EERKLAQAYV KITQDDREMA QAEGKFAQKE  1680
ETLAQRGEKL SQEAEKLAQK RKKLAKKWEK VAREEEKLAK KGGKLAEVKN ILAQKVEELP  1740
QREQNLDWQE KELAQELEEL EWDMEELSWK EEELNQEEGK LVEEKKKLAE EEEALAWQRE  1800
KLSEEETKLA QEEELLIQEK EKLAQHKEKM PEEEERLGRK REQLIEKKMK LAQKRERWIN  1860
SMEELTKNKM ILYQKKNLAQ EKKNLAQEKE KLAQRKENLL YNKERLTHSK KQLVQVKNKL  1920
GMFNKILAQV EEKLTQEKET VIKKKEKLAE TEKKLVQVED SLAKKQEKLA QEKMKLALEK  1980
AMVQGKKRLR GELDIAKEEK ALNLEMKRLA EEKMRLVEGK ETLSKGETPE TSRQRKMTQV  2040
EQELFERKLS LEEKILLHED RILAMEESEI AKGKLEFTRG QRIFVQGQRK LAKASRKLIK  2100
KRESLSKEPA KLNKILKALQ KLTRDERKLT QEEIKMTKMK RALFVKERRL SIEQSKLDIK  2160
EWDFSEKRSE LTKDEKKLAR KQRKLANKMR RMINKEEKMT EEESKLARKH SEVILDDEEE  2220
GGIEEEEVIP FLKRRWRKRK EAKRGDKPKE KFSSQVDEVE SEEHFSEEME SLLDELEKQE  2280
SLSSEEEEER EEEEERIEEE EREEEEERKE EEEGEEKQVE KEEEEKKKKK KEKKKKEEVQE 2340
KEEVFEEKEE IMSEEETESL SDEEEEEESC SLEEEVDREK EILKKEKQFK LQEQRRKSLR  2400
GRERVLSILR GVPHGKGRAI RLGVLKSPLK KLMSTALEMK EKTPVPVPEK QISWEDKKAT  2460
VVEIPRKFLG TMDKEREVMG KYEPIPPHVL GTVLESQAQD LKTPFMSHIL RRTVEAEELQ  2520
HKPLGAWWKW FLQHPPLMGQ TEVQLPLSQI PAKEQHADVS LSDVEWIRHV LERMEAGEQL  2580
SRDGFHRLCQ LLKDLASKGN LEWLHLAKHE AIVYRHRQAL ESQDTRISSR QSMSPKYLKV  2640
IPPIKAKEKE SWPKPLAVPT QKSPLATKRI PDPRAKNWHL LGEPYRSERA QQISIAHKEM  2700
```

-continued

```
EMQYFYPATR DIFPSAHASV EKQTLALMFQ KDFWDFKDKR RFPKLPKLEK KTQPISKKKE  2760
ELPLWETFVA LYHVLRMLQQ RYPKDSTAWM EQFYQLMDLY QLKSPRIQKL LQELLMREEP  2820
QPQEIIYEEA LKATELVPGE RLFCCLFCGS SHTPRSPQEF QGAVPLPWQN CVRTILPVGI  2880
ARYGILELAW KSLPEADLHL TKALTHTVAP TL                               2912

SEQ ID NO: 81          moltype = AA  length = 606
FEATURE                Location/Qualifiers
source                 1..606
                       mol_type = protein
                       organism = Homo sapiens
SEQUENCE: 81
MSHTASSCQE LVENCAVHVA GMAQEDSRRG QVPSSFYHGA NQELDLSTKV YKRESGSPYS  60
VLVDTKMSKP HLHETEEQPY FRETRAVSDV HAVKEDRENS DDTEEEEEEV SYKREQIIVE  120
VNLNNQTLNV SKGEKGVSSQ SKETPVLKTS SEEEEEESEE EATDDSNDYG ENEKQKKKEK  180
IVEKVSVTQR RTRRAASVAA ATTSPTPRTT RGRRKSVEPP KRKKRATKEP KAPVQKAKCE  240
EKETLTCEKC PRVFNTRWYL EKHMNVTHRR MQICDKCGKK FVLESELSLH QQTDCEKNIQ  300
CVSCNKSFKK LWSLHEHIKI VHGYAEKKFS CEICEKKFYT MAHVRKHMVA HTKDMPFTCE  360
TCGKSFKRSM SLKVHSLQHS GEKPFRCENC DERFQYKYQL RSHMSIHIGH KQFMCQWCGK  420
DFNMKQYFDE HMKTHTGEKP FICEICGKSF TSRPNMKRHR RTHTGEKPYP CDVCGQRFRF  480
SNMLKAHKEK CFRVTSPVNV PPAVQIPLTT SPATPVPSVV NTATTPTPPI NMNPVSTLPP  540
RPIPHPFSHL HIHPHPHHPH HLPIPPVPHL PPPPALFKSE PLNHRGQSED NFLRHLAEKN  600
SSAQHH                                                            606
```

What is claimed is:

1. A method of assessing whether a therapy or treatment regimen for a neurological injury or brain injury is effective in a subject, the method comprising:

(A) quantitatively measuring the levels of the one or more protein biomarkers, or fragments thereof, in a biological sample obtained from a subject at a first time point prior to initiation of a therapy or treatment regimen for a neurological or brain injury, wherein the one or more protein biomarkers or fragments thereof comprise Astrotactin 2 (ASTN2);

(B) quantitatively measuring the levels of the same, one or more protein biomarkers, or fragments thereof, in step (A), in a biological sample obtained from the subject at a second time point, after initiation of the therapy or treatment regimen; and (C) (i) ceasing treatment for neurological injury or brain injury when the measured levels of the one or more protein biomarkers, or fragments thereof, are decreased or trending to normal levels, in the biological sample obtained at the second time point, as compared with measured levels of the one or more protein biomarkers, or fragments thereof, at the first time point; or (ii) continuing treatment for neurological injury or brain injury when the measured levels of the one or more protein biomarkers, or fragments thereof, are increased or trending to abnormal levels, in the biological sample obtained at the second time point, as compared with measured levels of the one or more protein biomarkers, or fragments thereof, at the first time point.

2. The method of claim 1, wherein the one or more protein biomarkers, or fragments thereof, further comprise von Willebrand Factor (vWF).

3. The method of claim 2, wherein ASTN2, comprises an amino acid sequence of SEQ ID NO. 12.

4. The method of claim 1, wherein the one or more protein biomarkers further comprise one or more protein biomarkers, or fragments thereof, selected from: Brain-Derived Neurotrophic Factor (BDNF); Glial Fibrillary Acidic Protein (GFAP); Intracellular Adhesion Molecule 5 (ICAM5); Synuclein Beta (SNCB); Metallothionein 3 (MT3); Neurogranin (NRGN); Neuron Specific Enolase (NSE); and Aldolase C (ALDOC).

5. The method of claim 4, further comprising quantitatively measuring the levels of one of more subsets of other proteins selected from proteins 1-81 listed in Table 1, or fragments thereof, wherein the one or more subsets of other proteins, or fragments thereof, comprise at least one or more proteins from at least one of the following groups of proteins:

(i) a synapse protein;

(ii) at least one protein biomarker found in astrocytes; or (iii) a protein with a role in a brain repair process selected from one or more inflammation proteins; or (iv) combinations of (i), (ii), and (iii).

6. The method according to claim 1, wherein the neurological injury or brain injury is:

(A) an alteration in cellular or molecular integrity, activity, level, robustness, state, or other alteration of the brain, that is traceable to an event; or (B) a condition that results in central nervous system damage, irrespective of its pathophysiological basis; or (C) a traumatic brain injury or a concussion.

7. The method according to claim 1, wherein the biological sample is a fluid sample selected from the group consisting of a blood sample, a serum sample, a plasma sample, CSF sample, a saliva sample, a urine sample, a sputum sample, a secretion sample, and a tear sample.

8. The method according to claim 1, wherein the levels of the one or more protein biomarkers, or fragments thereof, are quantitatively measured in a protein detection assay by:

(A) (i) separately contacting the samples from the first and second timepoints with one or more binding agents that specifically bind the one or more of the protein biomarkers, or fragments thereof, and (ii) detecting binding of the one or more binding agents to one or more of the protein biomarkers present in the samples; or (B) using mass spectrometry to separately detect the presence of the one or more protein biomarkers, or fragments thereof, the samples from the first and second timepoints.

9. The method according to claim 1, wherein the levels of the one or more of the protein biomarkers, or fragments thereof, are decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100%, at the second timepoint as compared to the first timepoint.

10. A method of detecting one or more protein biomarkers or fragments thereof, in a biofluid sample obtained from a subject having, or suspected of having a neurological injury or brain injury, the method comprising the steps of:

A) obtaining the biofluid sample from the patient; and

B) detecting Astrotactin 2 (ASTN2) in the biofluid sample by an assay or mass spectrometry.

* * * * *